United States Patent
Honda et al.

(10) Patent No.: US 11,970,611 B2
(45) Date of Patent: Apr. 30, 2024

(54) MEMBER FOR WEARABLE DEVICE

(71) Applicant: DAIKIN INDUSTRIES, LTD., Osaka (JP)

(72) Inventors: Yoshiaki Honda, Osaka (JP); Teruyuki Fukuda, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 1019 days.

(21) Appl. No.: 16/757,653

(22) PCT Filed: Oct. 30, 2018

(86) PCT No.: PCT/JP2018/040329
§ 371 (c)(1),
(2) Date: Apr. 20, 2020

(87) PCT Pub. No.: WO2019/088099
PCT Pub. Date: May 9, 2019

(65) Prior Publication Data
US 2020/0325331 A1 Oct. 15, 2020

(30) Foreign Application Priority Data
Oct. 31, 2017 (JP) .................. 2017-211224

(51) Int. Cl.
*C08L 71/00* (2006.01)
*A44C 5/00* (2006.01)
(Continued)

(52) U.S. Cl.
CPC ............ *C08L 71/00* (2013.01); *A44C 5/0007* (2013.01); *A44C 5/14* (2013.01); *B32B 27/08* (2013.01);
(Continued)

(58) Field of Classification Search
CPC ......... C08L 71/00; A44C 5/0007; A44C 5/14; B32B 27/08; B32B 27/306; B32B 3/02;
(Continued)

(56) References Cited

U.S. PATENT DOCUMENTS 6,091,546 A * 7/2000 Spitzer ............... G02B 27/0172
351/158
2002/0137842 A1 9/2002 Sato et al.
(Continued)

FOREIGN PATENT DOCUMENTS

| CN | 1643005 A | 7/2005 |
| CN | 106663638 A | 5/2017 |

(Continued)

OTHER PUBLICATIONS

Jplatpat Machine English translation of JP 2016-132719A (Year: 2016).*
(Continued)

*Primary Examiner* — Alicia J Weydemeyer
*Assistant Examiner* — Laura B Figg
(74) *Attorney, Agent, or Firm* — Sughrue Mion, PLLC

(57) ABSTRACT

The present invention provides a member for a wearable device, the member including a resin base material, an electronic component, and a protecting layer which protects the electronic component, wherein the protecting layer is a layer formed from a curable composition including a perfluoropolyether group-containing compound.

8 Claims, 7 Drawing Sheets

(51) Int. Cl.
*A44C 5/14* (2006.01)
*A61B 5/024* (2006.01)
*B32B 3/02* (2006.01)
*B32B 27/08* (2006.01)
*B32B 27/30* (2006.01)
*C08G 65/00* (2006.01)
*C08G 65/336* (2006.01)
*C09D 171/00* (2006.01)
*G02C 5/00* (2006.01)
*G02C 11/00* (2006.01)

(52) U.S. Cl.
CPC .......... *B32B 27/306* (2013.01); *C08G 65/007* (2013.01); *C08G 65/336* (2013.01); *C09D 171/00* (2013.01); *G02C 5/008* (2013.01); *G02C 11/10* (2013.01); *A61B 5/02438* (2013.01); *B32B 3/02* (2013.01); *B32B 2433/00* (2013.01); *B32B 2457/00* (2013.01); *B32B 2551/00* (2013.01)

(58) Field of Classification Search
CPC ........... B32B 2433/00; B32B 2457/00; B32B 2551/00; C08G 65/007; C08G 65/336; C09D 171/00; G02C 5/008; G02C 11/10; A61B 5/02438
See application file for complete search history.

(56) References Cited

U.S. PATENT DOCUMENTS

| | | | |
|---|---|---|---|
| 2006/0052558 | A1 | 3/2006 | Morikawa et al. |
| 2006/0270791 | A1† | 11/2006 | Kishita |
| 2007/0293644 | A1 | 12/2007 | Morikawa et al. |
| 2009/0284149 | A1* | 11/2009 | Koshikawa .......... C08G 65/336 313/512 |
| 2014/0107263 | A1† | 4/2014 | Shiono |
| 2015/0118502 | A1 | 4/2015 | Mitsuhashi et al. |
| 2016/0040039 | A1† | 2/2016 | Yamane |
| 2016/0353567 | A1* | 12/2016 | Ichiryu ................. H05K 1/185 |
| 2017/0233602 | A1 | 8/2017 | Itami et al. |
| 2017/0325336 | A1 | 11/2017 | Shibata et al. |
| 2018/0030280 | A1 | 2/2018 | Mitsuhashi et al. |
| 2018/0288882 | A1 | 10/2018 | Shibata et al. |
| 2020/0253059 | A1 | 8/2020 | Shibata et al. |
| 2021/0017394 | A1 | 1/2021 | Mitsuhashi et al. |

FOREIGN PATENT DOCUMENTS

| | | | |
|---|---|---|---|
| CN | 107109197 A | | 8/2017 |
| EP | 3 184 289 A1 | | 6/2017 |
| EP | 3 792 997 A1 | | 3/2021 |
| JP | 1997-263640 A | † | 10/1997 |
| JP | H09-263640 A | | 10/1997 |
| JP | 2002-110184 A | | 4/2002 |
| JP | 2007-002228 A | | 1/2007 |
| JP | 2008-214566 A | † | 9/2008 |
| JP | 2009-149782 A | † | 7/2009 |
| JP | 2009-277887 A | | 11/2009 |
| JP | 2014-77070 A | | 5/2014 |
| JP | 2016-037541 A | | 3/2016 |
| JP | 2016-132719 A | | 7/2016 |
| JP | 2016132719 A | * | 7/2016 |
| JP | 2016-183319 A | | 10/2016 |
| JP | 2016-219782 A | | 12/2016 |
| JP | 2017-006230 A | | 1/2017 |

OTHER PUBLICATIONS

International Preliminary Report on Patentability dated May, 5 2020 with translation of the Written Opinion from the International Bureau in International Application No. PCT/JP2018/040329.
Communication dated Jul. 19, 2021 by the European Patent Office in counterpart application No. 18872984.2.
International Search Report for PCT/JP2018/040329 dated Feb. 5, 2019 [PCT/ISA210].

\* cited by examiner
† cited by third party

MEMBER FOR WEARABLE DEVICE

CROSS REFERENCE TO RELATED APPLICATIONS

This application is a National Stage of International Application No. PCT/JP2018/040329 filed Oct. 30, 2018, claiming priority based on Japanese Patent Application No. 2017-211224 filed Oct. 31, 2017, the contents of all of which are incorporated herein by reference in their entirety.

TECHNICAL FIELD

The present invention relates to a member for a wearable device, and a wearable device comprising the member for a wearable device.

BACKGROUND ART

Wearable devices have recently attracted increased attention. Wearable devices mean electronics which can be utilized with being worn on the body, and, for example, a watch-type wearable device as described in Patent Literature 1 is known. Wearable devices can have various functions such as a function which detects a body movement and a function which controls other electronics.

CITATION LIST

Patent Literature

Patent Literature 1: JP 2017-6230 A

SUMMARY OF INVENTION

Technical Problem

Such a wearable device is demanded to have increased functions. Such a wearable device has various electronic components incorporated thereinto, due to increased functions. Such a sensor, if brought into contact with various external contaminants such as moisture, sweat, an oil content, and a chemical substance, can be deteriorated in functions.

Therefore, an object of the present invention is to provide a member for a wearable device, comprising an electronic component, in which the electronic component is protected against any external contaminant.

Solution to Problem

The present inventors have made intensive studies in order to solve the above problems, and as a result, have found that an electronic component can be protected against various contaminants by protection with a perfluoropolyether group-containing compound, thereby leading to completion of the present invention.

A first aspect of the present invention provides a member for a wearable device, the member including a resin base material, an electronic component, and a protecting layer which protects the electronic component, wherein the protecting layer is a layer formed from a curable composition including a perfluoropolyether group-containing compound.

A second aspect of the present invention provides a wearable device comprising the member for a wearable device of the present invention.

Effects of Invention

The present invention provides a member for a wearable device, the member including an electronic component, in which the electronic component is protected by a perfluoropolyether group-containing compound, and thus the electronic component can be inhibited from being deteriorated.

DESCRIPTION OF EMBODIMENTS

Figure 1:
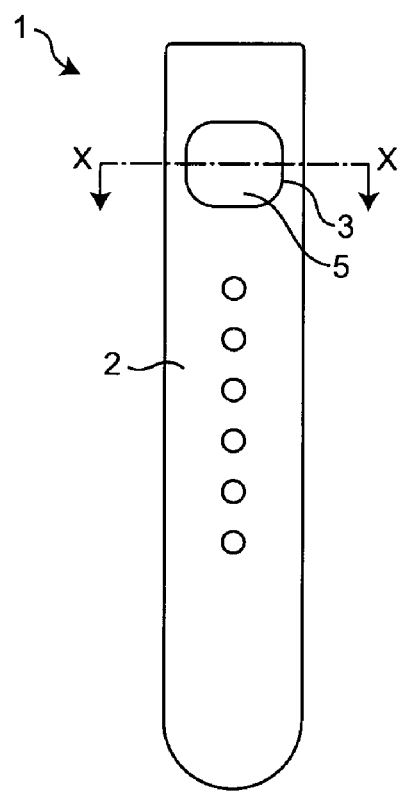
FIG. 1 is a plan view of a watch band member 1 in one embodiment of the present invention.

The member for a wearable device of the present invention includes a resin base material, an electronic component, and a protecting layer which protects the electronic component.

The resin constituting the resin base material is not limited, and may be, for example, a non-fluororesin (or also referred to as "general-purpose resin") or a fluororesin.

The non-fluororesin is not limited, and examples thereof include a polyolefin-based resin such as polyethylene, polypropylene, an ethylene-propylene copolymer or an ethylene-vinyl acetate copolymer (EVA), a cycloolefin resin, modified polyolefin, a polyvinyl chloride-based resin such as polyvinyl chloride, polyvinylidene chloride, polystyrene, polyamide, polyimide, polyamideimide, polycarbonate, poly-(4-methylpentene-1), an ionomer, an acrylic resin such as polymethyl methacrylate (PMMA), an acryl-styrene copolymer (AS resin), a butadiene-styrene copolymer, an ethylene-vinyl alcohol copolymer (EVOH), polyester such as polyethylene terephthalate (PET), polybutylene terephthalate (PBT) or polycyclohexane terephthalate (PCT), polyether, polyetherketone (PEK), polyetheretherketone (PEEK), polyetherimide, polyacetal (POM), polyphenylene oxide, modified polyphenylene oxide, polyarylate, aromatic polyester (liquid crystal polymer), a styrene-based resin, a polyurethane-based resin, a chlorinated polyethylene-based resin, an epoxy resin, a phenol resin, a urea resin, a melamine resin, unsaturated polyester, a silicone resin, polydimethylsilicone (PDMS), polyurethane, or a copolymer, a blend or a polymer alloy thereof.

Examples of the fluororesin include an ethylene-tetrafluoroethylene copolymer (ETFE), a vinylidene fluoride-hexafluoropropylene-tetrafluoroethylene copolymer (FKM), polytetrafluoroethylene, a tetrafluoroethylene-hexafluoropropylene copolymer (FEP), a perfluoroalkoxy copolymer (PFA), an ethylene-chlorotrifluoroethylene copolymer (ECTFE), polyvinyl fluoride (PVF), polyvinylidene fluoride (PVDF), polychlorotrifluoroethylene (PCTFE), a vinylidene fluoride-hexafluoropropylene copolymer (VdF-HFP), a vinylidene fluoride-tetrafluoroethylene-hexafluoropropylene copolymer (VdF-TFE-HFP), other fluorine-based resin, or a fluoroelastomer, and may be a blend resin or a polymer alloy thereof.

In one embodiment, the resin may be a fluoroelastomer.

Examples of the fluoroelastomer include a non-perfluoro-fluoroelastomer and a perfluoro-fluoroelastomer.

Examples of the non-perfluoro-fluoroelastomer include a vinylidene fluoride (VDF)-based fluoroelastomer, a tetrafluoroethylene (TFE)/propylene (Pr)-based fluoroelastomer, a tetrafluoroethylene (TFE)/propylene/vinylidene fluoride (VDF)-based fluoroelastomer, an ethylene/hexafluoropropylene (HFP)-based fluoroelastomer, an ethylene/hexafluoropropylene (HFP)/vinylidene fluoride (VDF)-based fluoroelastomer, an ethylene/hexafluoropropylene (HFP)/tetrafluoroethylene (TFE)-based fluoroelastomer, a fluorosilicone-based fluoroelastomer, and a fluorophosphazene-based fluoroelastomer, and such a resin can be used singly or in any combinations thereof as long as the effect of the present invention is not impaired. In particular, a vinylidene fluoride-based fluoroelastomer and a tetrafluoroethylene/propylene-based fluoroelastomer are preferable.

The vinylidene fluoride-based fluoroelastomer refers to a fluorine-containing elastic copolymer including 45 to 85 mol % of vinylidene fluoride and 55 to 15 mol % of at least another monomer copolymerizable with vinylidene fluoride.

The fluoroelastomer preferably refers to a fluorine-containing elastic copolymer including 50 to 80 mol % of vinylidene fluoride and 50 to 20 mol % of at least another monomer copolymerizable with vinylidene fluoride.

Examples of such at least another monomer copolymerizable with vinylidene fluoride include fluorine-containing monomers such as tetrafluoroethylene (TFE), chlorotrifluoroethylene (CTFE), trifluoroethylene, hexafluoropropylene (HFP), trifluoropropylene, tetrafluoropropylene, pentafluoropropylene, trifluorobutene, tetrafluoroisobutene, perfluoro(alkylvinylether) (PAVE) and vinyl fluoride, and non-fluorine monomers such as ethylene, propylene and alkylvinylether. Such each monomer can be used singly or in any combinations thereof. In particular, tetrafluoroethylene, hexafluoropropylene, and perfluoro(alkylvinylether) are preferable.

Examples of such perfluoro(alkylvinylether) in this case include perfluoro(methyl vinyl ether) and perfluoro(propyl vinyl ether), and such each resin can be used singly or in any combinations thereof as long as the effect of the present invention is not impaired.

Specific examples of the vinylidene fluoride-based fluoroelastomer include VDF-HFP-based rubber, VDF-HFP-TFE-based rubber, VDF-CTFE-based rubber, and VDF-CTFE-TFE-based rubber.

The tetrafluoroethylene/propylene-based fluoroelastomer refers to a fluorine-containing elastic copolymer including 45 to 70 mol % of tetrafluoroethylene, 55 to 30 mol % of propylene, and 0 to 5 mol % of a monomer imparting a crosslinking site.

Examples of the monomer imparting a crosslinking site include any iodine-containing monomer such as perfluoro (6,6-dihydro-6-iodo-3-oxa-1-hexene) and perfluoro(5-iodo-3-oxa-1-pentene) described in JP H05-63482 B or JP H07-316234 A, any bromine-containing monomer described in JP H04-505341 A, and any nitrile group-containing monomer, carboxyl group-containing monomer and alkoxycarbonyl group-containing monomer described in JP H04-505345 A or JP H05-500070 A.

Examples of the perfluoro-fluoroelastomer include perfluororubber including TFE, such as a fluorine-containing elastic copolymer including TFE/perfluoro(alkylvinylether) (PAVE)/monomer imparting a crosslinking site. The compositional feature thereof is preferably 45 to 90/10 to 50/0 to 5 (mol %), more preferably 45 to 80/20 to 50/0 to 5, further preferably 53 to 70/30 to 45/0 to 2. If the compositional feature does not fall within the range, properties of a rubber elastomer tend to be impaired and close to properties of a resin.

Examples of such PAVE here include perfluoro(methyl vinyl ether) (PMVE) and perfluoro(propyl vinyl ether) (PPVE), and such a resin can be used singly or in any combinations thereof as long as the effect of the present invention is not impaired.

Examples of the monomer imparting a crosslinking site include an iodine-containing monomer represented by the following formula:

wherein X represents H, F or $CH_3$, $R_f$ represents a fluoroalkylene group, a perfluoroalkylene group, a fluoropolyoxyalkylene group or a perfluoropolyoxyalkylene group, and R represents H or $CH_3$, and a monomer represented by the following formula:

wherein m is an integer of 0 to 5, n is an integer of 1 to 3, Y represents a nitrile group, a carboxyl group, an alkoxycarbonyl group or a bromine atom, and such a resin can be used singly or in any combinations thereof as long as the effect of the present invention is not impaired. Such iodine atom, nitrile group, carboxyl group, alkoxycarbonyl group and bromine atom each serve as a crosslinking point.

Specific examples of such a perfluoro-fluoroelastomer include any fluoroelastomer described in WO 97/24381, JP S61-57324 B, JP H04-81608 B or JP H05-13961 B.

The resin constituting the resin base material may be used singly or in combinations of two or more kinds thereof.

The shape of the resin base material is not limited, and may be any shape depending on the application or the like. For example, the shape may be a watch band shape in the case of a watch-type wearable device, the shape may be an eyeglass frame shape in the case of an eyeglass-type wearable device, and the shape may be a wristband shape in the case of a wristband-type wearable device.

Examples of the electronic component is not limited, and include a battery, various sensors such as a pressure sensor, an acceleration sensor, a heartbeat sensor, an altitude sensor, a water pressure sensor and a magnetic sensor, a communication module, or a wireless charging unit.

The electronic component may be adopted singly or in combinations of two or more kinds thereof.

For example, the electronic component may be present in the resin base material or on the surface of the base material.

In one embodiment, the electronic component is embedded in the resin base material.

In one embodiment, the electronic component is disposed in a concave portion provided in the resin base material.

In one embodiment, the electronic component is disposed on the surface of the resin base material.

The protecting layer is formed from a curable composition including a perfluoropolyether group-containing compound (hereinafter, also referred to as "PFPE-containing compound").

The thickness of the protecting layer is not limited, and may be, for example, 10 μm or more and 1.0 mm or less, preferably 20 μm or more and 500 μm or less, more preferably 30 μm or more and 200 μm or less.

A section where the protecting layer is to be formed is not limited as long as such a section is any section where the electronic component can be protected.

In one embodiment, the electronic component is directly covered with the protecting layer.

In one embodiment, the electronic component is present in the resin base material, and a section of the resin base material, the section corresponding to a section where the electronic component is present, is covered with the protecting layer.

In one embodiment, for example, the electronic component may be exposed from the protecting layer. In particular, for example, no protecting layer may be present in a section necessary for exhibiting any function of the electronic component. Examples of the section necessary for exhibiting the function include an electrode section of a battery, a detection section of a sensor, and a terminal section of other electronic component.

Hereinafter, the PFPE-containing compound will be described.

The "2-10 valent organic group", as used herein, means a 2-10 valent group containing carbon. The 2-10 valent organic group is not limited, and examples thereof include a 2-10 valent group where 1 to 9 hydrogen atoms are further removed from a hydrocarbon group. The divalent organic group is not limited, and examples thereof include a divalent group where one hydrogen atom is further removed from a hydrocarbon group.

The "hydrocarbon group", as used herein, means a group which contains carbon and hydrogen and which is obtained by removing one hydrogen atom from a molecule. The hydrocarbon group is not limited, and examples thereof include a hydrocarbon group having 1 to 20 carbon atoms, optionally substituted with one or more substituents, such as an aliphatic hydrocarbon group and an aromatic hydrocarbon group. For example, the "aliphatic hydrocarbon group" may be any linear, branched or cyclic group, and may be any saturated or unsaturated group. For example, the hydrocarbon group may contain one or more ring structures. The hydrocarbon group may have one or more N, O, S, Si, amide, sulfonyl, siloxane, carbonyl, carbonyloxy, and the like at an end thereof or in a molecular chain thereof.

Examples of the substituent of the "hydrocarbon group", as used herein, is not limited, and include a halogen atom; and one or more groups selected from a $C_{1-6}$ alkyl group, a $C_{2-6}$ alkenyl group, a $C_{2-6}$ alkynyl group, a $C_{3-10}$ cycloalkyl group, a $C_{3-10}$ unsaturated cycloalkyl group, a 5 to 10-membered heterocyclyl group, a 5 to 10-membered unsaturated heterocyclyl group, a $C_{6-10}$ aryl group and a 5 to 10-membered heteroaryl group each optionally substituted with one or more halogen atoms.

The alkyl group and the phenyl group may be herein unsubstituted or substituted, unless particularly noted. Examples of the substituent of such groups is not limited, and include one or more groups selected from a halogen atom, a $C_{1-6}$ alkyl group, a $C_{2-6}$ alkenyl group and a $C_{2-6}$ alkynyl group.

The PFPE-containing compound is not limited, and is typically a perfluoropolyether group-containing silane compound (hereinafter, also referred to as "PFPE-containing silane compound") or a perfluoropolyether group-containing compound having a carbon-carbon double bond at a molecular end (hereinafter, also referred to as "PFPE-containing unsaturated compound"). The PFPE-containing compound may be adopted singly or in combinations of two or more kinds thereof.

The PFPE-containing silane compound has a Si atom bonded to at least one group selected from the group consisting of a hydroxyl group and a hydrolyzable group, at each of both molecular ends.

In one embodiment, the PFPE-containing silane compound is at least one compound represented by formula (A), (B), (C) or (D).

[Formula 1]

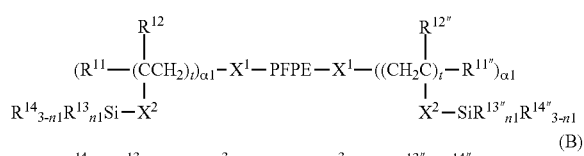

Formula (A)

[Formula 2]

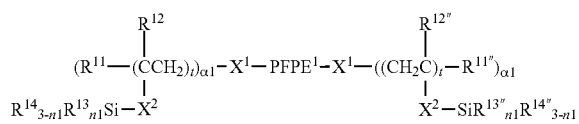

In the formulae, PFPE, at each occurrence, is each independently a group represented by:

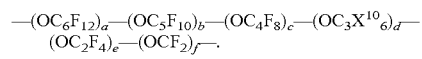

In the formulae, a, b, c, d, e and f are each independently an integer of 0 or more and 200 or less, and the sum of a, b, c, d, e and f is at least 1. Preferably, the sum of a, b, c, d, e and f is 5 or more, more preferably 10 or more. Preferably, the sum of a, b, c, d, e and f is 200 or less, more preferably 200 or less, for example, 10 or more and 200 or less, more specifically 10 or more and 100 or less. The occurrence order of the respective repeating units in parentheses with a, b, c, d, e or f is not limited in the formula. $X^{10}$, at each occurrence, each independently represents a hydrogen atom, a fluorine atom or a chlorine atom, preferably a hydrogen atom or a fluorine atom, more preferably a fluorine atom.

Here, a and b are each independently preferably 0 or more and 30 or less, and, for example, may be 0.

In one embodiment, a, b, c and d are each independently preferably an integer of 0 or more and 30 or less, more preferably an integer of 20 or less, particularly preferably an integer of 10 or less, further preferably an integer of 5 or less, or, for example, may be 0.

In one embodiment, the sum of a, b, c and d is preferably 30 or less, more preferably 20 or less, further preferably 10 or less, particularly preferably 5 or less.

In one embodiment, the sum of e and f is preferably 30 or more, more preferably 40 or more, further preferably 50 or more.

Such repeating units may, for example, be linear or branched, and are preferably linear. For example, —(OC$_6$F$_{12}$)— may be —(OCF$_2$CF$_2$CF$_2$CF$_2$CF$_2$CF$_2$)—, —(OCF(CF$_3$)CF$_2$CF$_2$CF$_2$CF$_2$)—, —(OCF$_2$CF(CF$_3$)CF$_2$CF$_2$CF$_2$)—, —O$_0$CF$_2$CF$_2$CF(CF$_3$)CF$_2$CF$_2$)—, —(OCF$_2$CF$_2$CF$_2$CF(CF$_3$)CF$_2$)—, —(OCF$_2$CF$_2$CF$_2$CF$_2$CF(CF$_3$))—, or the like, and is preferably —(OCF$_2$CF$_2$CF$_2$CF$_2$CF$_2$CF$_2$)—. For example, —(OC$_5$F$_{10}$)— may be —(OCF$_2$CF$_2$CF$_2$CF$_2$CF$_2$)—, —(OCF(CF$_3$)CF$_2$CF$_2$CF$_2$)—, —(OCF$_2$CF(CF$_3$)CF$_2$CF$_2$)—, —(OCF$_2$CF$_2$CF(CF$_3$)CF$_2$)—. —(OCF$_2$CF$_2$CF$_2$CF(CF$_3$))—, or the like, and is preferably —(OCF$_2$CF$_2$CF$_2$CF$_2$CF$_2$)—. —(OC$_4$F$_8$)— may be any of —(OCF$_2$CF$_2$CF$_2$CF$_2$)—, —(OCF(CF$_3$)CF$_2$CF$_2$)—, —(OCF$_2$CF(CF$_3$)CF$_2$)—, —(OCF$_2$CF$_2$CF(CF$_3$))—, —(OC(CF$_3$)$_2$CF$_2$)—, —(OCF$_2$C(CF$_3$)$_2$)—, —(OCF(CF$_3$)CF(CF$_3$))—, —(OCF(C$_2$F$_5$)CF$_2$)— and —(OCF$_2$CF(C$_2$F$_5$))—, and is preferably —(OCF$_2$CF$_2$CF$_2$CF$_2$)—. —(OC$_3$F$_6$)— (namely, in the formulae, X$^{10}$ represents a fluorine atom) may be any of —(OCF$_2$CF$_2$CF$_2$)—, —(OCF(CF$_3$)CF$_2$)— and —(OCF$_2$CF(CF$_3$))—, and is preferably —(OCF$_2$CF$_2$CF$_2$)—. —(OC$_2$F$_4$)— may be any of —(OCF$_2$CF$_2$)— and —(OCF(CF$_3$))—, and is preferably —(OCF$_2$CF$_2$)—.

In one embodiment, PFPE is —(OC$_2$F$_6$)$_d$—, wherein d is an integer of 1 or more and 200 or less, preferably 5 or more and 200 or less, more preferably 10 or more and 200 or less. Preferably, PFPE is —(OCF$_2$CF$_2$CF$_2$)$_d$—, wherein d is an integer of 1 or more and 200 or less, preferably 5 or more and 200 or less, more preferably 10 or more and 200 or less, or —(OCF(CF$_2$)CF$_2$)$_d$—, wherein d is an integer of 1 or more and 200 or less, preferably 5 or more and 200 or less, more preferably 10 or more and 200 or less. More preferably, PFPE is —(OCF$_2$CF$_2$CF$_2$)$_d$—, wherein d is an integer of 1 or more and 200 or less, preferably 5 or more and 200 or less, more preferably 10 or more and 200 or less.

In another embodiment, PFPE is —(OC$_4$F$_8$)$_e$—(OC$_2$F$_6$)$_d$—(OC$_2$F$_4$)$_e$—(OCF$_2$)$_f$—, wherein c and d are each independently an integer of 0 or more and 30 or less, e and f are each independently 1 or more and 200 or less, preferably 5 or more and 200 or less, more preferably an integer of 10 or more and 200 or less, the sum of c, d, e and f is at least 5 or more, preferably 10 or more, and the occurrence order of the respective repeating units in parentheses with the subscript c, d, e or f is not limited in the formulae. Preferably, PFPE is —(OCF$_2$CF$_2$CF$_2$CF$_2$)$_c$—(OCF$_2$CF$_2$CF$_2$)$_d$—(OCF$_2$CF$_2$)$_e$—(OCF$_2$)$_f$—.

In one embodiment, PFPE may be —(OC$_2$F$_4$)$_e$—(OCF$_2$)$_f$—, wherein e and f are each independently an integer of 1 or more and 200 or less, preferably 5 or more and 200 or less, more preferably 10 or more and 200 or less, and the occurrence order of the respective repeating units in parentheses with the subscript e or f is not limited in the formulae. The curable composition used in the present invention, which includes the PFPE-containing silane compound, can contribute to formation of a cured product which can keep rubber properties even at a low temperature.

In still another embodiment, PFPE is a group represented by —(R$^6$—R$^7$)$_j$—. In the formulae, R$^6$ represents OCF$_2$ or OC$_2$F$_4$, preferably OC$_2$F$_4$. In the formula, R$^7$ represents a group selected from OC$_2$F$_4$, OC$_3$F$_6$, OC$_4$F$_8$, OC$_5$F$_{10}$ and OC$_6$F$_{12}$, or a combination of two or three groups independently selected from the above groups. Preferably, R$^7$ represents a group selected from OC$_2$F$_4$, OC$_3$F$_6$ and OC$_4$F$_8$, a group selected from OC$_3$F$_6$, OC$_4$F$_8$, OC$_5$F$_{10}$ and OC$_6$F$_{12}$, or a combination of two or three groups independently selected from the above groups. Such a combination of two or three groups independently selected from OC$_2$F$_4$, OC$_3$F$_6$ and OC$_4$F$_8$ is not limited, and examples thereof include —OC$_2$F$_4$OC$_3$F$_6$—, —OC$_2$F$_4$OC$_4$F$_8$—, —OC$_3$F$_6$OC$_2$F$_4$—, —C$_3$F$_6$OC$_3$F$_6$—, —OC$_3$F$_6$OC$_4$F$_8$—, —OC$_4$F$_8$OC$_4$F$_8$—, —OC$_4$F$_8$OC$_3$F$_6$—, —OC$_4$F$_8$OC$_2$F$_4$—, —OC$_2$F$_4$OC$_2$F$_4$OC$_3$F$_6$—, —OC$_2$F$_4$OC$_2$F$_4$OC$_4$F$_8$—, —OC$_2$F$_4$OC$_3$F$_6$OC$_2$F$_4$—, —OC$_2$F$_4$OC$_3$F$_6$OC$_3$F$_6$—, —OC$_2$F$_4$OC$_4$F$_8$OC$_2$F$_4$—, —OC$_3$F$_6$OC$_2$F$_4$OC$_2$F$_4$—, —OC$_3$F$_6$OC$_2$F$_4$OC$_3$F$_6$—, —OC$_3$F$_6$OC$_3$F$_6$OC$_2$F$_4$—, and —OC$_4$F$_8$OC$_2$F$_4$OC$_2$F$_4$—. Here, j is an integer of 2 or more, preferably 3 or more, more preferably 5 or more, and an integer of 100 or less, preferably 50 or less. In the formulae, OC$_2$F$_4$, OC$_3$F$_6$, OC$_4$F$_8$, OC$_5$F$_{10}$ and OC$_6$F$_{12}$ may be linear or branched, and is preferably linear. In this embodiment, PFPE is preferably —(OC$_2$F$_4$—OC$_3$F$_6$)— or —(OC$_2$F$_4$—OC$_4$F$_8$)$_j$—.

The ratio of e to f in PFPE (hereinafter, referred to as "e/f ratio") is 0.1 or more and 10 or less, preferably 0.2 or more and 5 or less, more preferably 0.2 or more and 2 or less, further preferably 0.2 or more and 1.5 or less. The e/f ratio, which falls within the range, can more enhance water-repellency, oil-repellency and chemical resistance (for example, durability to brine, aqueous acidic or basic solution, acetone, oleic acid or hexane) of a cured product obtained from the compound. A lower e/f ratio more enhances water-repellency, oil-repellency and chemical resistance of the cured product. On the other hand, an e/f ratio of 0.1 or more can more enhance stability of the compound. A higher e/f ratio more enhances stability of the compound.

In one embodiment, the e/f ratio is less than 1.0. The e/f ratio is preferably 0.10 or more, more preferably 0.20 or more, further preferably 0.40 or more. The e/f ratio is preferably 0.90 or less, more preferably 0.85 or less, further preferably 0.80 or less. In the present embodiment, the e/f ratio is preferably 0.10 or more and 1.0 or less, 0.20 or more and 0.90 or less, further preferably 0.40 or more and 0.85 or less, particularly preferably 0.40 or more and 0.80 or less.

In one embodiment, the e/f ratio is 1.0 or more. The e/f ratio is preferably 1.1 or more, more preferably 1.2 or more. The e/f ratio is preferably 10.0 or less, more preferably 5.0 or less, further preferably 2.0 or less, particularly preferably 1.5 or less. In the present embodiment, the e/f ratio is preferably 1.0 or more and 10.0 or less, more preferably 1.0 or more and 5.0 or less, further preferably 1.0 or more and 2.0 or less, particularly preferably 1.0 or more and 1.5 or less.

The number average molecular weight of the -PFPE- portion in the PFPE-containing silane compound is not limited, and is, for example, 500 to 30,000, preferably 1,500 to 30,000, more preferably 2,000 to 10,000. The number average molecular weight is defined as a value obtained by $^{19}$F-NMR measurement.

The number average molecular weight of the -PFPE- portion may be in the range from 2000 to 200000, and is preferably in the range from 3000 to 100000. The number average molecular weight is defined as a value obtained by $^{19}$F-NMR measurement.

In one embodiment, the number average molecular weight of the -PFPE- portion may be in the range from 1,000 to 3,000, and is preferably in the range from 2000 to 3000. The compound can have such a number average molecular weight of the -PFPE- portion to thereby allow the curable composition to be low in viscosity and be improved in handleability.

In one embodiment, the number average molecular weight of the -PFPE- portion may be in the range from 5,000 to 10,000, and is preferably in the range from 6000 to 9000. The compound may have such a number average molecular weight of the -PFPE- portion to thereby allow the curable composition to be improved in physical properties such as stretching properties after curing.

In the formulae, $R^{13}$, at each occurrence, each independently represents a hydroxyl group or a hydrolyzable group. The hydrolyzable group is as defined above.

In the formulae, $R^{14}$, at each occurrence, each independently represents a hydrogen atom or an alkyl group having 1 to 22 carbon atoms, preferably an alkyl group having 1 to 4 carbon atoms.

In the formulae, $R^{11}$, at each occurrence, each independently represents a hydrogen atom or a halogen atom. The halogen atom is preferably an iodine atom, a chlorine atom or a fluorine atom, more preferably a fluorine atom.

In the formulae, $R^{12}$, at each occurrence, each independently represents a hydrogen atom or a lower alkyl group. The lower alkyl group is preferably an alkyl group having 1 to 20 carbon atoms, more preferably an alkyl group having 1 to 6 carbon atoms, and examples thereof include a methyl group, an ethyl group and a propyl group.

In the formulae, $R^{11''}$, $R^{12''}$, $R^{13''}$ and $R^{14''}$ have the same meanings as $R^{11}$, $R^{12}$, $R^{13}$ and $R^{14}$, respectively.

In formula (A), the Si atom bonded to at least one group selected from the group consisting of a hydroxyl group and a hydrolyzable group indicates a Si atom included in ($-SiR^{13}{}_{n1}R^{14}{}_{3-n1}$) or ($-SiR^{13''}{}_{n1}R^{14''}{}_{3-n1}$) where n1 is an integer of 1 to 3.

In the formulae, n1 with respect to each ($-SiR^{13}{}_{n1}R^{14}{}_{3-n1}$) unit or each ($-SiR^{13''}{}_{n1}R^{14''}{}_{3-n1}$) unit is independently an integer of 0 to 3, preferably 1 to 3, more preferably 3. In the formulae, at least two n1 are each an integer of 1 to 3, namely, there is not any case where all n1 are simultaneously 0. In the formulae, at least one $R^{13}$ and at least one $R^{14''}$ are present. In formula (A), at least one $-SiR^{13}{}_{n1}R^{14}{}_{3-n1}$ structure (namely, $-SiR^{13}$ portion) where n1 is 1 or more and at least one $-SiR^{13''}{}_{n1}R^{14''}{}_{3-n1}$ structure (namely, $-SiR^{14''}$ portion) where n1 is 1 or more are present.

Preferably, the Si atom bonded to at least one group selected from the group consisting of a hydroxyl group and a hydrolyzable group is present at both ends of a molecular backbone in formula (A). That is, at least one $-SiR^{13}{}_{n1}R^{14}{}_{3-n1}$ structure (namely, $-SiR^{13}$ portion) where n1 is 1 or more and at least one $-SiR^{13''}{}_{n1}R^{14''}{}_{3-n1}$ structure (namely, $-SiR^{13''}$ portion) where n1 is 1 or more are present in formula (A).

In the formulae, $X^1$ each independently represents a single bond or a 2-10 valent organic group. $X^1$ is understood to be a linker which links a perfluoropolyether portion (namely, -PFPE- portion) mainly providing water-repellency, surface lubricity, and the like, and a silane portion (namely, group in parentheses with α1) providing a binding ability to the base material, in any compound represented by formula (A). Accordingly, $X^1$ may be a single bond or any organic group as long as such any compound represented by formula (A) can be stably present. Herein, a left portion and a right portion of the group designated as $X^1$ are bonded to the group represented by PFPE and the group in parentheses with α1, respectively.

In another embodiment, $X^1$ may be $X^e$. $X^e$ represents a single bond or a 2-10 valent organic group, preferably represents a single bond or a 2-10 valent organic group having at least one selected from the group consisting of $-C_6H_4-$ (namely, -phenylene-, hereinafter, representing a phenylene group), $-CO-$ (carbonyl group), $-NR^4-$ and $-SO_2-$. Each $R^4$ independently represents a hydrogen atom, a phenyl group, or a $C_{1-6}$ alkyl group (preferably a methyl group), preferably represents a hydrogen atom or a methyl group. Such $-C_6H_4-$, $-CO-$, $-NR^4-$ or $-SO_2-$ is preferably contained in a molecular backbone of the PFPE-containing silane compound.

$X^e$ more preferably represents a single bond or a 2-10 valent organic group having at least one selected from the group consisting of $-C_6H_4-$, $-CONR^4-$, $-CONR^4-C_6H_4-$, $-CO-$, $-CO-C_6H_4-$, $-SO_2NR^4-$, $-SO_2NR^4-C_6H_4-$, $-SO_2-$, and $-SO_2-C_6H_4-$. Such $-C_6H_4-$, $-CONR^4-$, $-CONR^4-C_6H_4-$, $-CO-$, $-CO-C_6H_4-$, $-SO_2NR^4-$, $-SO_2NR^4-C_6H_4-$, $-SO_2-$, or $-SO_2-C_6H_4-$ is preferably contained in a molecular backbone of the PFPE-containing silane compound.

In the formulae, α1 is an integer of 1 to 9, and may be varied depending on the valence of $X^1$. In formula (A), α1 corresponds to a value obtained by subtracting 1 from the valence of $X^1$. In the case where $X^1$ is a single bond, α1 is 1.

$X^1$ is preferably a 2-7 valent, more preferably 2-4 valent, further preferably divalent organic group.

In one embodiment, $X^1$ is a 2-4 valent organic group, and α1 is 1 to 3.

In another embodiment, $X^1$ is a divalent organic group, and α1 is 1. In such a case, formula (A) is represented by the following formula (A').

[Formula 3]

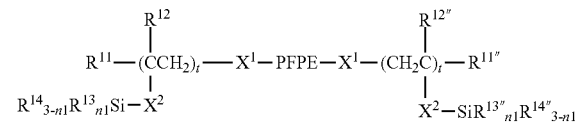

(A')

Examples of $X^1$ are not limited, and include a divalent group represented by the following formula:

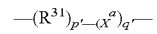

wherein:
$R^{31}$ represents a single bond, $-(CH_2)_{s'}-$, or an o-, m- or p-phenylene group, preferably represents $-(CH_2)_{s'}-$,
s' is an integer of 1 to 20, preferably an integer of 1 to 6, more preferably an integer of 1 to 3, still more preferably 1 or 2,
$X^a$ represents, $-(X^b)_1-$,
$X^b$, at each occurrence, each independently represents a group selected from the group consisting of $-O-$, $-S-$, o-, m- or p-phenylene group, $-C(O)O-$, $-Si(R^{33})_2-$, $-(Si(R^{33})_2O)_{m'}-Si(R^{33})_2-$, $-CONR^{34}-$, $-O-CONR^{34}-$, $-NR^{34}-$ and $-(CH_2)_{m'}-$,
$R^{33}$, at each occurrence, each independently represents a phenyl group, a $C_{1-6}$ alkyl group or a $C_{1-6}$ alkoxy group, preferably represents a phenyl group or a $C_{1-6}$ alkyl group, more preferably represents a methyl group, $R^{34}$, at each occurrence, each independently represents a hydrogen atom, a phenyl group, or a $C_{1-6}$ alkyl group (preferably a methyl group), m', at each occurrence, is each independently an integer of 1 to 100, preferably an integer of 1 to 20, n', at each occurrence, is each independently an integer of 1 to 20, preferably an integer of 1 to 6, more preferably an integer of 1 to 3, l' is an integer of 1 to 10, preferably an integer of 1 to 5, more preferably an integer of 1 to 3, p' is 0 or 1, and q' is 0 or 1, provided that at least one of p' and q' is 1, and the occurrence order of the respective repeating units in parentheses with p' or q' is not limited. Here, $R^{31}$ and $X^a$ (typically, any hydrogen atom in $R^{31}$ and $X^a$) are each optionally substituted with one or more substituents selected from a fluorine atom, a $C_{1-3}$ alkyl group and a $C_{1-3}$ fluoroalkyl group.

In one embodiment, l' is 1.

Preferably, $X^1$ is —$(R^{31})_{p'}$—$(X^a)_{q'}$—$R^{32}$—. $R^{32}$ represents a single bond, —$(CH_2)_{t'}$—, or an o-, m- or p-phenylene group, preferably —$(CH_2)_{t'}$—. Here, t' is an integer of 1 to 20, preferably an integer of 2 to 6, more preferably an integer of 2 to 3. Here, $R^{32}$ (typically, any hydrogen atom in $R^{32}$) is optionally substituted with one or more substituents selected from a fluorine atom, a $C_{1-3}$ alkyl group and a $C_{1-3}$ fluoroalkyl group.

Preferably, $X^1$ may be a single bond, a $C_{1-20}$ alkylene group,

—$R^{31}$—$X^c$—$R^{32}$—, or

—$X^d$—$R^{32}$— wherein $R^{31}$ and $R^{32}$ are as defined above. Herein, such an alkylene group is a group having a —$(C_\delta H_{2\delta})$— structure, and is optionally substituted or unsubstituted and is optionally linear or branched.

Further preferably, $X^1$ is

—$X^f$—, a —$X^f$—$C_{1-20}$ alkylene group,

—$X^f$—$(CH_2)_{s'}$—$X^c$—,

—$X^f$—$(CH_2)_{s'}$—$X^c$—$(CH_2)_{t'}$—,

—$X^f$—$X^d$—, or

—$X^f$—$X^d$—$(CH_2)_{t'}$— wherein s' and t' are as defined above.

In the formulae, $X^f$ is an alkylene group having 1 to 6 carbon atoms, preferably 1 to 4 carbon atoms, more preferably 1 to 2 carbon atoms, for example, a methylene group. Any hydrogen atom in $X^f$ is optionally substituted with one or more substituents selected from a fluorine atom, a $C_{1-3}$ alkyl group and a $C_{1-3}$ fluoroalkyl group, and is preferably substituted. $X^f$ may be linear or branched, and is preferably linear.

More preferably, $X^1$ is a single bond, a $C_{1-20}$ alkylene group,

—$(CH_2)_{s'}$—$X^c$—, $(CH_2)_{s'}$—$X^c$—$(CH_2)_{t'}$—

—$X^d$—, or

—$X^d$—$(CH_2)_{t'}$— wherein s' and t' are as defined above.

In the formulae, $X^c$ represents

—O—,

—S—,

—C(O)O—,

—$CONR^{34}$—,

—O—$CONR^{34}$—,

—$Si(R^{33})_2$—,

—$(Si(R^{33})_2O)_{m'}$—$Si(R^{33})_2$—,

—O—$(CH_2)_{u'}$—$(Si(R^{33})_2O)_{m'}$—$Si(R^{33})_2$—,

—O—$(CH_2)_{u'}$—$Si(R^{33})_2$—O—$Si(R^{33})_2$—$CH_2CH_2$—$Si(R^{33})_2$—O—$Si(R^{33})_2$—,

—O—$(CH_2)_{u'}$—$Si(OCH_3)_2OSi(OCH_3)_2$—,

—$CONR^{34}$—$(CH_2)_{u'}$—$(Si(R^{33})_2O)_{m'}$—$Si(R^{33})_2$—,

—$CONR^{34}$—$(CH_2)_{u'}$—$N(R^{34})$—, or

—$CONR^{34}$-(o-, m- or p-phenylene)-$Si(R^{33})_2$— wherein $R^{33}$, $R^{34}$ and m' are as defined above, and u' is an integer of 1 to 20, preferably an integer of 2 to 6, more preferably an integer of 2 to 3. $X^c$ is preferably —O—.

In the formulae, $X^d$ represents

—S—,

—C(O)O—,

—$CONR^{34}$—,

—$CONR^{34}$—$(CH_2)_{u'}$—$(Si(R^{33})_2O)_{m'}$—$Si(R^{33})_2$—,

—$CONR^{34}$—$(CH_2)_{u'}$—$N(R^{34})$—, or

—$CONR^{34}$-(o-, m- or p-phenylene)-$Si(R^{33})_2$— wherein each symbol is as defined above.

Particularly preferably, $X^1$ is a group represented by

—$X^f$—, a —$X^f$—$C_{1-20}$ alkylene group,

—$X^f$—$(CH_2)_{s'}$—$X^c$—,

—$X^f$—$(CH_2)_{s'}$—$X^c$—$(CH_2)_{t'}$—

—$X^f$—$X^d$—, or

—$X^f$—$X^d$—$(CH_2)_{t'}$— wherein $X^f$, s' and t' are as defined above;

$X^c$ represents —O—, or —$CONR^{34}$—, $X^d$ represents —$CONR^{34}$—, and each $R^{34}$, at each occurrence, independently represents a hydrogen atom, a phenyl group, or a $C_{1-6}$ alkyl group (preferably a methyl group).

In one embodiment, $X^1$ is a group represented by

—$X^f$—$(CH_2)_{s'}$—$X^c$—,

—$X^f$—$(CH_2)_{s'}$—$X^c$—$(CH_2)_{t'}$—

—$X^f$—$X^d$—, or

—$X^f$—$X^d$—$(CH_2)_{t'}$— wherein $X^f$, s' and t' are as defined above;

$X^c$ represents —$CONR^{34}$—, $X^d$ represents —$CONR^{34}$—, and $R^{34}$, at each occurrence, each independently represents a hydrogen atom, a phenyl group or a $C_{1-6}$ alkyl group (preferably a methyl group).

In one embodiment, $X^1$ may be, a single bond, a $C_{1-20}$ alkylene group,

—$(CH_2)_{s'}$—$X^c$—$(CH_2)_{t'}$—, or

—$X^d$—$(CH_2)_{t'}$— wherein each symbol is as defined above.

Preferably, $X^1$ is a single bond, a $C_{1-20}$ alkylene group,

—$(CH_2)_{s'}$—O—$(CH_2)_{t'}$—, $(CH_2)_{s'}$—$(Si(R^{33})_2O)_{m'}$—$Si(R^{33})_2$—$(CH_2)_{t'}$—,

—$(CH_2)_{s'}$—O—$(CH_2)_{u'}$—$(Si(R^{33})_2O)_{m'}$—$Si(R^{33})_2$—$(CH_2)_{t'}$—, or

—$(CH_2)_{s'}$—O—$(CH_2)_{t'}$—$Si(R^{33})_2$—$(CH_2)_{u'}$—$Si(R^{33})_2$—$(CH_vH_{2v})$— wherein $R^{33}$, m', s', t' and u' are as defined above, and v is an integer of 1 to 20, preferably an integer of 2 to 6, more preferably an integer of 2 to 3.

In the formulae, —($C_vH_{2v}$)— is optionally linear or branched, and may be, for example, —$CH_2$—, —$CH_2CH_2$—, —$CH_2CH_2CH_2$—, —$CH(CH_3)$— or —$CH(CH_3)CH_2$—.

The $X^1$ group is optionally substituted with one or more substituents selected from a fluorine atom, a $C_{1-3}$ alkyl group and a $C_{1-3}$ fluoroalkyl group (preferably $C_{1-3}$perfluoroalkyl group).

In one embodiment, the $X^1$ group may be other than a —O—$C_{1-6}$ alkylene group.

In another embodiment, examples of the $X^1$ group include the following groups:

[Formula 4]

$$-D-\underset{R^{41}}{\overset{R^{41}}{Si}}-O-\underset{R^{41}}{\overset{R^{41}}{Si}}-E-$$

$$-D-\underset{R^{41}}{\overset{R^{41}}{Si}}-O-\underset{R^{41}}{\overset{R^{41}}{Si}}-O-\underset{R^{41}}{\overset{R^{41}}{Si}}-E-$$

$$-D-\underset{R^{41}}{\overset{R^{41}}{Si}}-O-\underset{R^{41}}{\overset{R^{41}}{Si}}-O-\underset{R^{41}}{\overset{R^{41}}{Si}}-O-\underset{R^{41}}{\overset{R^{41}}{Si}}-E-$$

$$-D-\underset{R^{41}}{\overset{R^{41}}{Si}}-O-\underset{R^{41}}{\overset{R^{41}}{Si}}-O-\underset{R^{41}}{\overset{R^{41}}{Si}}-O-\underset{R^{41}}{\overset{R^{41}}{Si}}-O-\underset{R^{41}}{\overset{R^{41}}{Si}}-E-$$

[Formula 5]

$$-D-\underset{R^{41}}{\overset{R^{41}}{Si}}-CH_2CH_2-\underset{R^{41}}{\overset{R^{41}}{Si}}-E-$$

$$-D-\underset{R^{41}}{\overset{R^{41}}{Si}}-\text{(phenylene)}-\underset{R^{41}}{\overset{R^{41}}{Si}}-E-$$

$$-D-\underset{R^{41}}{\overset{R^{41}}{Si}}-\text{(cyclohexylene-CH}_2CH_2\text{)}-\underset{R^{41}}{\overset{R^{41}}{Si}}-E-$$

wherein $R^{41}$ each independently represents a hydrogen atom, a phenyl group, an alkyl group having 1 to 6 carbon atoms, or a $C_{1-6}$ alkoxy group, preferably a methyl group;

D is a group selected from
—$CH_2O(CH_2)_2$—,
—$CH_2O(CH_2)_3$—,
—$CF_2O(CH_2)_3$—,
—$(CH_2)_2$—,
—$(CH_2)_3$—,
—$(CH_2)_4$—,
—CONH—$(CH_2)_3$—,
—CON($CH_3$)—$(CH_2)_3$—,
—CON(Ph)-$(CH_2)_3$—, wherein Ph means phenyl; and

[Formula 6]

$$-\overset{O}{\underset{}{C}}-\underset{R^{42}}{N}-\text{(phenylene with }Si(R^{42})_2-CH_2CH_2-\text{)}$$

wherein $R^{42}$ each independently represents a hydrogen atom, a $C_{1-6}$ alkyl group or a $C_{1-6}$ alkoxy group, preferably a methyl group or a methoxy group, more preferably a methyl group;
E is —$(CH_2)_{ne}$— (ne is an integer of 2 to 6),
D is bonded to PFPE as a molecular backbone, and E is bonded to an opposite group to PFPE.

Specific examples of $X^1$ include:
a single bond,
—$CH_2OCH_2$—,
—$CH_2O(CH_2)_2$—,
—$CH_2O(CH_2)_3$—,
$CH_2O(CH_2)_6$—,
—$CF_2$—$CH_2$—O—$CH_2$—,
—$CF_2$—$CH_2$—O—$(CH_2)_2$—,
—$CF_2$—$CH_2$—O—$(CH_2)_3$—,
—$CF_2$—$CH_2$—O—$(CH_2)_6$—,
—$CH_2O(CH_2)_3Si(CH_3)_2OSi(CH_3)_2(CH_2)_2$—,
—$CH_2O(CH_2)_3Si(CH_3)_2OSi(CH_3)_2OSi(CH_3)_2(CH_2)_2$—,
—$CH_2O(CH_2)_3Si(CH_3)_2O(Si(CH_3)_2O)_2Si(CH_3)_2(CH_2)_2$—,
—$CH_2O(CH_2)_3Si(CH_3)_2O(Si(CH_3)_2O)_3Si(CH_3)_2(CH_2)_2$—,
—$CH_2O(CH_2)_3Si(CH_3)_2O(Si(CH_3)_2O)_{10}Si(CH_3)_2(CH_2)_2$—,
—$CH_2O(CH_2)_3Si(CH_3)_2O(Si(CH_3)_2O)_{20}Si(CH_3)_2(CH_2)_2$—,
—$CH_2OCF_2CHFOCF_2$—,
—$CH_2OCF_2CHFOCF_2CF_2$—,
—$CH_2OCF_2CHFOCF_2CF_2CF_2$—,
—$CH_2OCH_2CF_2CF_2OCF_2$—,
—$CH_2OCH_2CF_2CF_2OCF_2CF_2$—,
—$CH_2OCH_2CF_2CF_2OCF_2CF_2CF_2$—,
—$CH_2OCH_2CF_2CF_2OCF(CF_3)CF_2OCF_2$—,
—$CH_2OCH_2CF_2CF_2OCF(CF_3)CF_2OCF_2CF_2$—,
—$CH_2OCH_2CF_2CF_2OCF(CF_3)CF_2OCF_2CF_2CF_2$—,
—$CH_2OCH_2CHFCF_2OCF_2$—,
—$CH_2OCH_2CHFCF_2OCF_2CF_2$—,
—$CH_2OCH_2CHFCF_2OCF_2CF_2CF_2$—,
—$CH_2OCH_2CHFCF_2OCF(CF_3)CF_2OCF_2$—,
—$CH_2OCH_2CHFCF_2OCF(CF_3)CF_2OCF_2CF_2$—,
—$CH_2OCH_2CHFCF_2OCF(CF_3)CF_2OCF_2CF_2CF_2$—,
—$CH_2OCF_2CHFOCF_2CF_2CF_2$—C(O)NH—$CH_2$—,
—$CH_2OCH_2$ $(CH_2)_7CH_2Si(OCH_3)_2OSi(OCH_3)_2(CH_2)_2Si(OCH_3)_2OSi(OCH_3)_2(CH_2)_2$—,
—$CH_2OCH_2CH_2CH_2Si(OCH_3)_2OSi(OCH_3)_2(CH_2)_3$—,
—$CH_2OCH_2CH_2CH_2Si(OCH_2CH_3)_2OSi(OCH_2CH_3)_2(CH_2)_3$—,
—$CH_2OCH_2CH_2CH_2Si(OCH_3)_2OSi(OCH_3)_2(CH_2)_2$—,
—$CH_2OCH_2CH_2CH_2Si(OCH_2CH_3)_2OSi(OCH_2CH_3)_2(CH_2)_2$—,
—$(CH_2)_2$—$Si(CH_3)_2$—$(CH_2)_2$—,
—$CH_2$—,
—$(CH_2)_2$—,
—$(CH_2)_3$—,
—$(CH_2)_4$—,
—$(CH_2)_5$—, —(CH$_2$)$_6$—,
—CF$_2$—,
—(CF$_2$)$_2$—,
—CF$_2$—CH$_2$—,
—CF$_2$—(CH$_2$)$_2$—,
—CF$_2$—(CH$_2$)$_3$—,
—CF$_2$—(CH$_2$)$_4$—,
—CF$_2$—(CH$_2$)$_5$—,
—CF$_2$—(CH$_2$)$_6$—,
—CO—
—CONH—
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—S—(CH$_2$)$_3$—,
(CH$_2$)$_2$S(CH$_2$)$_3$—,
—CONH—(CH$_2$)$_3$Si(CH$_3$)$_2$OSi(CH$_3$)$_2$(CH$_2$)$_2$—,
—CONH—(CH$_2$)$_3$Si(CH$_3$)$_2$OSi(CH$_3$)$_2$OSi(CH$_3$)$_2$(CH$_2$)$_2$—,
—CONH—(CH$_2$)$_3$Si(CH$_3$)$_2$O(Si(CH$_3$)$_2$O)$_2$Si(CH$_3$)$_2$(CH$_2$)$_2$—,
—CONH—(CH$_2$)$_3$Si(CH$_3$)$_2$O(Si(CH$_3$)$_2$O)$_3$Si(CH$_3$)$_2$(CH$_2$)$_2$—,
—CONH—(CH$_2$)$_3$Si(CH$_3$)$_2$O(Si(CH$_3$)$_2$O)$_{10}$Si(CH$_3$)$_2$(CH$_2$)$_2$—, —CONH—(CH$_2$)$_3$Si(CH$_3$)$_2$O(Si(CH$_3$)$_2$O)$_2$OSi(CH$_3$)$_2$(CH$_2$)$_2$—,
—C(O) O—(CH$_2$)$_3$—,
—C(O) O—(CH$_2$)$_6$—,
—CH$_2$—O—(CH$_2$)$_3$—Si(CH$_3$)$_2$—(CH$_2$)$_2$—Si(CH$_3$)$_2$—(CH$_2$)$_2$—,
—CH$_2$—O—(CH$_2$)$_3$—Si(CH$_3$)$_2$—(CH$_2$)$_2$—Si(CH$_3$)$_2$—CH(CH$_3$)—,
—CH$_2$—O—(CH$_2$)$_3$—Si(CH$_3$)$_2$—(CH$_2$)$_2$—Si(CH$_3$)$_2$—(CH$_2$)$_3$—,
—CH$_2$—O—(CH$_2$)$_3$—Si(CH$_3$)$_2$—(CH$_2$)$_2$—Si(CH$_3$)$_2$—CH(CH$_3$)—CH$_2$—,
—OCH$_2$—,
—O(CH$_2$)$_3$—, and
—OCFHCF$_2$—

[Formula 7]

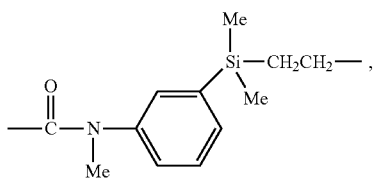

In particular, $X^1$ is preferably
—CH$_2$OCH$_2$—,
—CH$_2$O(CH$_2$)$_2$—,
—CH$_2$O(CH$_2$)$_3$—,
—CH$_2$O(CH$_2$)$_6$—,
—CF$_2$—CH$_2$—O—CH$_2$—,
—CF$_2$—CH$_2$—O—(CH$_2$)$_2$—,
—CF$_2$—CH$_2$—O—(CH$_2$)$_3$—,
—CF$_2$—CH$_2$—O—(CH$_2$)$_6$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CF$_2$CF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
—CH$_2$OCH$_2$CHFCF$_2$OCF$_2$—,
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$)CF$_2$OCF$_2$—,
—CH$_2$OCH$_2$CHFCF$_2$OCF(CF$_3$)CF$_2$OCF$_2$CF$_2$—,
—CH$_2$OCH$_2$CHFCF$_2$OCF(CF$_3$)CF$_2$OCF$_2$CF$_2$CF$_2$—,
—CH$_2$OCF$_2$CHFOCF$_2$CF$_2$CF$_2$—C(O)NH—CH$_2$—,
—CH$_2$—,
—(CH$_2$)$_2$—,
—(CH$_2$)$_3$—,
—(CH$_2$)$_4$—,
—(CH$_2$)$_5$—,
—(CH$_2$)$_6$—,
—CF$_2$—,
(CF$_2$)$_2$—,
—CF$_2$—CH$_2$—,
—CF$_2$—(CH$_2$)$_2$—,
—CF$_2$—(CH$_2$)$_3$—,
—CF$_2$—(CH$_2$)$_4$—,
—CF$_2$—(CH$_2$)$_5$—,
—CF$_2$—(CH$_2$)$_6$—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—, —CH$_2$O—CONH—(CH$_2$)$_3$—,
—CH$_2$O—CONH—(CH$_2$)$_6$—,
—OCH$_2$—,
—O(CH$_2$)$_3$—, or
—OCFHCF$_2$—.
In particular, X$^1$ is more preferably
—CH$_2$OCF$_2$CHFOCF$_2$CF$_2$CF$_2$—C(O)NH—CH$_2$—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—.

In a more preferable embodiment, X$^1$ represents X$^{e'}$. X$^{e'}$ is a single bond, an alkylene group having 1 to 6 carbon atoms, —R$^{51}$—C$_6$H$_4$—R$^{52}$—, —R$^{51}$—CONR$^4$—R$^{52}$—, —R$^{51}$—CONR$^4$—C$_6$H$_4$—R$^{52}$—, —R$^{51}$—CO—R$^{52}$—, —R$^{51}$—CO—C$_6$H$_4$—R$^{52}$—, —R$^{51}$—SO$_2$NR$^4$—R$^{52}$—, —R$^{51}$—SO$_2$NR$^4$—C$_6$H$_4$—R$^{52}$—, —R$^{51}$—SO$_2$—R$^{52}$—, or —R$^{51}$—SO$_2$—C$_6$H$_4$—R$^{52}$—. R$^{51}$ and R$^{52}$ each independently represent a single bond or an alkylene group having 1 to 6 carbon atoms, preferably a single bond or an alkylene group having 1 to 3 carbon atoms. R$^4$ is as defined above. The alkylene group is substituted or unsubstituted, preferably unsubstituted. Examples of the substituent of the alkylene group may include a halogen atom, preferably a fluorine atom. The alkylene group is linear or branched, preferably linear.

In a further preferable embodiment, X$^{e'}$ may be
a single bond,
—X$^f$—,
an alkylene group having 1 to 6 carbon atoms, preferably 1 to 3 carbon atoms
a —X$^f$—C$_{1-6}$ alkylene group, preferably a —X$^f$—C$_{1-3}$ alkylene group, more preferably
a —X$^f$—C$_{1-2}$ alkylene group,
—C$_6$H$_4$—R$^{52'}$—,
—CONR$^{4'}$—R$^{52'}$—,
—CONR$^{4'}$—C$_6$H$_4$—R$^{42'}$—,
—X$^f$—CONR$^{4'}$—R$^{52'}$—,
—X$^f$—CONR$^{4'}$—C$_6$H$_4$—R$^{52'}$—,
—CO—R$^{52'}$—,
—CO—C$_6$H$_4$—R$^{52'}$—,
—SO$_2$NR$_{4'}$—R$^{52'}$—,
—SO$_2$NR$^{4'}$—C$_6$H$_4$—R$^{52'}$—,
—SO$_2$—R$^{52'}$—,
—SO$_2$—C$_6$H$_4$—R$^{52'}$—,
—R$^{51'}$—C$_6$H$_4$—,
—R$^{51'}$—CONR$^{4'}$—,
—R$^{51'}$—CONR$^{4'}$—C$_6$H$_4$—,
—R$^{51'}$—CO—,
—R$^{51'}$—CO—C$_6$H$_4$—,
—R$^{51'}$—SO$_2$NR$^{4'}$—,
—R$^{51'}$—SO$_2$NR$^{4'}$—C$_6$H$_4$—,
—R$^{31'}$—SO$_2$—,
—R$^{51'}$—SO$_2$—C$_6$H$_4$—,
—C$_6$H$_4$—
—CONR$^{4'}$—,
—CONR$^{4'}$—C$_6$H$_4$—,
—X$^f$—CONR$^{4'}$—,
—X$^f$—CONR$^{4'}$—C$_6$H$_4$—,
—CO—,
—CO—C$_6$H$_4$—,
—SO$_2$NR$^{4'}$—,
—SO$_2$NR$^{4'}$—C$_6$H$_4$—
—SO$_2$—, or
—SO$_2$—C$_6$H$_4$—
wherein R$^{51'}$ and R$^{52'}$ each independently represent a linear alkylene group having 1 to 6 carbon atoms, preferably 1 to 3 carbon atoms, the alkylene group is substituted or unsubstituted, as described above, and examples of the substituent of the alkylene group may include a halogen atom, preferably a fluorine atom, and R$^{4'}$ is a hydrogen atom or a methyl group.

In particular, X$^{e'}$ may be preferably
—X$^f$—,
an alkylene group having 1 to 6 carbon atoms, preferably 1 to 3 carbon atoms, or
a —X$^f$—C$_{1-6}$ alkylene group, preferably a —X$^f$—C$_{1-3}$ alkylene group, more preferably
a —X$^f$—C$_{1-2}$ alkylene group,
—CONR$^{4'}$—R$^{52'}$—,
—CONR$^{4'}$—C$_6$H$_4$—R$^{52'}$—,
—X$^f$—CONR$^{4'}$—R$^{52'}$—,
—X$^f$—CONR$^{4'}$—C$_6$H$_4$—R$^{52'}$—,
—R$^{51'}$—CONR$^{4'}$—,
—R$^{51'}$—CONR$^{4'}$—C$_6$H$_4$—,
—CONR$^{4'}$—,
—CONR$^{4'}$—C$_6$H$_4$—,
—X$^f$—CONR$^{4'}$—,
—X$^f$—CONR$^{4'}$—C$_6$H$_4$—,
—R$^{51'}$—CONR$^{4'}$—, or
—R$^{51'}$—CONR$^{4'}$—C$_6$H$_4$—. In the formulae, X$^f$, R$^{4'}$, R$^{51'}$ and R$^{52'}$ each are as defined above.

In particular, X$^{e'}$ may be more preferably
—CONR$^{4'}$—R$^{52'}$—,
—CONR$^{4'}$—C$_6$H$_4$—R$^{52'}$—,
—X$^f$—CONR$^{4'}$—R$^{52'}$—,
—X$^f$—CONR$^{4'}$—C$_6$H$_4$—R$^{52'}$—,
—R$^{51'}$—CONR$^{4'}$—,
—R$^{51'}$—CONR$^{4'}$—C$_6$H$_4$—,
—CONR$^{4'}$—,
—CONR$^{4'}$—C$_6$H$_4$—,
—X$^f$—CONR$^{4'}$—, or
—X$^f$—CONR$^{4'}$—C$_6$H$_4$—.

In the present embodiment, specific examples of X$^{e'}$ include
a single bond,
a perfluoroalkylene group having 1 to 6 carbon atoms (for example, —CF$_2$—, —(CF$_2$)$_2$—,
an alkylene group having 1 to 6 carbon atoms,
—CF$_2$—C$_{1-6}$ alkylene group,
—CONH—,
—CONH—CH$_2$—,
—CONH—(CH$_2$)$_2$—,
—CONH—(CH$_2$)$_3$—,
—CF$_2$—CONH—,
—CF$_2$CONHCH$_2$—,
—CF$_2$CONH(CH$_2$)$_2$—,
—CF$_2$CONH(CH$_2$)$_3$—, —CON(CH$_3$)—,
—CON(CH$_3$)—CH$_2$—,
—CON(CH$_3$)—(CH$_2$)$_2$—,
—CON(CH$_3$)—(CH$_2$)$_3$—,
—CF$_2$—CON(CH$_3$)—,
—CF$_2$—CON(CH$_3$)CH$_2$—,
—CF$_2$—CON(CH$_3$)—(CH$_2$)$_2$—,
—CF$_2$—CON(CH$_3$)—(CH$_2$)$_3$—,
—CH$_2$—CONH—,
—CH$_2$—CONH—CH$_2$—,
—CH$_2$—CONH—(CH$_2$)$_2$—,
—CH$_2$—CONH—(CH$_2$)$_3$—,
—CF$_2$—CH$_2$—CONH—,
—CF$_2$—CH$_2$—CONH—CH$_2$—,
—CF$_2$—CH$_2$—CONH—(CH$_2$)$_2$—,
—CF$_2$—CH$_2$—CONH—(CH$_2$)$_3$—,
—CONH—C$_6$H$_4$—,
—CON(CH$_3$)—C$_6$H$_4$—,
—CH$_2$—CON(CH$_3$)—CH$_2$—,
—CH$_2$—CON(CH$_3$)—(CH$_2$)$_2$—,
—CH$_2$—CON(CH$_3$)—(CH$_2$)$_3$—,
—CON(CH$_3$)—C$_6$H$_4$—,
—CF$_2$—CONH—C$_6$H$_4$—,
—CF$_2$—CON(CH$_3$)—C$_6$H$_4$—,
—CF$_2$—CH$_2$—CON(CH$_3$)—CH$_2$—,
—CF$_2$—CH$_2$—CON(CH$_3$)—(CH$_2$)$_2$—,
—CF$_2$—CH$_2$—CON(CH$_3$)—(CH$_2$)$_3$—,
—CF$_2$—CON(CH$_3$)—C$_6$H$_4$—,
—CO—,
—CO—C$_6$H$_4$—,
—C$_6$H$_4$—,
—SO$_2$NH—,
—SO$_2$NH—CH$_2$—,
—SO$_2$NH—(CH$_2$)$_2$—,
—SO$_2$NH—(CH$_2$)$_3$—,
—SO$_2$NH—C$_6$H$_4$—,
—SO$_2$N(CH$_3$)—,
—SO$_2$N(CH$_3$)—CH$_2$—,
—SO$_2$N(CH$_3$)—(CH$_2$)$_2$—,
—SO$_2$N(CH$_3$)—(CH$_2$)$_3$—,
—SO$_2$N(CH$_3$)—C$_6$H$_4$—,
—SO$_2$—,
—SO$_2$—CH$_2$—,
—SO$_2$—(CH$_2$)$_2$—,
—SO$_2$—(CH$_2$)$_3$—, or
—SO$_2$—C$_6$H$_4$—.

In the above list, examples of preferable X$^{e'}$ include
an alkylene group having 1 to 6 carbon atoms,
a perfluoroalkylene group having 1 to 6 carbon atoms (for example, —CF$_2$— and —(CF$_2$)$_2$—)$_r$
a —CF$_2$—C$_{1-6}$ alkylene group,
—CONH—,
—CONH—CH$_2$—,
—CONH—(CH$_2$)$_2$—,
—CONH—(CH$_2$)$_3$—,
—CF$_2$CONH—,
—CF$_2$CONHCH$_2$—,
—CF$_2$CONH(CH$_2$)$_2$—,
—CF$_2$CONH(CH$_2$)$_3$—,
—CON(CH$_3$)—,
—CON(CH$_3$)—CH$_2$—,
—CON(CH$_3$)—(CH$_2$)$_2$—,
—CON(CH$_3$)—(CH$_2$)$_3$—,
—CF$_2$—CON(CH$_3$)—,
—CF$_2$—CON(CH$_3$)CH$_2$—,
—CF$_2$—CON(CH$_3$)—(CH$_2$)$_2$—,
—CF$_2$—CON(CH$_3$)—(CH$_2$)$_3$—,
—CH$_2$—CONH—,
—CH$_2$—CONH—CH$_2$—,
—CH$_2$—CONH—(CH$_2$)$_2$—,
—CH$_2$—CONH—(CH$_2$)$_3$—,
—CF$_2$—CH$_2$—CONH—,
—CF$_2$—CH$_2$—CONH—CH$_2$—,
—CF$_2$—CH$_2$—CONH—(CH$_2$)$_2$—,
—CF$_2$—CH$_2$—CONH—(CH$_2$)$_3$—,
—CONH—C$_6$H$_4$—,
—CON(CH$_3$)—C$_6$H$_4$—,
—CH$_2$—CON(CH$_3$)—CH$_2$—,
—CH$_2$—CON(CH$_3$)—(CH$_2$)$_2$—,
—CH$_2$—CON(CH$_3$)—(CH$_2$)$_3$—,
—CON(CH$_3$)—C$_6$H$_4$—
—CF$_2$—CONH—C$_6$H$_4$—,
—CF$_2$—CON(CH$_3$)—C$_6$H$_4$—,
—CF$_2$—CH$_2$—CON(CH$_3$)—CH$_2$—,
—CF$_2$—CH$_2$—CON(CH$_3$)—(CH$_2$)$_2$—,
—CF$_2$—CH$_2$—CON(CH$_3$)—(CH$_2$)$_3$—, and
—CF$_2$—CON(CH$_3$)—C$_6$H$_4$.

In the above list, examples of more preferable X$^{e'}$ include
—CONH—,
—CONH—CH$_2$—,
—CONH—(CH$_2$)$_2$—,
—CONH—(CH$_2$)$_3$—,
—CF$_2$CONH—,
—CF$_2$CONHCH$_2$—,
—CF$_2$CONH(CH$_2$)$_2$—,
—CF$_2$CONH(CH$_2$)$_3$—,
—CON(CH$_3$)—,
—CON(CH$_3$)—CH$_2$—,
—CON(CH$_3$)—(CH$_2$)$_2$—,
—CON(CH$_3$)—(CH$_2$)$_3$—,
—CF$_2$—CON(CH$_3$)—,
—CF$_2$—CON(CH$_3$)CH$_2$—,
—CF$_2$—CON(CH$_3$)—(CH$_2$)$_2$—,
—CF$_2$—CON(CH$_3$)—(CH$_2$)$_3$—,
—CH$_2$—CONH—,
—CH$_2$—CONH—CH$_2$—,
—CH$_2$—CONH—(CH$_2$)$_2$—,
—CH$_2$—CONH—(CH$_2$)$_3$—,
—CF$_2$—CH$_2$—CONH—,
—CF$_2$—CH$_2$—CONH—CH$_2$—,
—CF$_2$—CH$_2$—CONH—(CH$_2$)$_2$—,
—CF$_2$—CH$_2$—CONH—(CH$_2$)$_3$—,
—CONH—C$_6$H$_4$—,
—CON(CH$_3$)—C$_6$H$_4$—,
—CH$_2$—CON(CH$_3$)—CH$_2$—,
—CH$_2$—CON(CH$_3$)—(CH$_2$)$_2$—,
—CH$_2$—CON(CH$_3$)—(CH$_2$)$_3$—,
—CON(CH$_3$)—C$_6$H$_4$—
—CF$_2$—CONH—C$_6$H$_4$—,
—CF$_2$—CON(CH$_3$)—C$_6$H$_4$—,
—CF$_2$—CH$_2$—CON(CH$_3$)—CH$_2$—,
—CF$_2$—CH$_2$—CON(CH$_3$)—(CH$_2$)$_2$—,
—CF$_2$—CH$_2$—CON(CH$_3$)—(CH$_2$)$_3$—, or
—CF$_2$—CON(CH$_3$)—C$_6$H$_4$—, In one embodiment, X$^{e'}$ is a single bond. In the present embodiment, PFPE and a group having a binding ability to the base material (namely, group in parentheses with α1 in (A)) are directly bonded.

In still another embodiment, X$^1$ is a group represented by formula: —(R$^{16}$)$_x$—(CFR$^{17}$)$_y$—(CH$_2$)$_z$—. In the formula, x, y and z are each independently an integer of 0 to 10, the sum of x, y and z is 1 or more, and the occurrence order of the respective repeating units in parentheses is not limited in the formula.

In the formula, $R^{16}$, at each occurrence, each independently represents an oxygen atom, phenylene, carbazolylene, —$NR^{18}$—, wherein $R^{18}$ represents a hydrogen atom or an organic group, or a divalent organic group. Preferably, $R^{16}$ is an oxygen atom or a divalent polar group.

The "divalent polar group" is not limited, and examples thereof include —C(O)—, —C(=$NR^{19}$)—, and —C(O)$NR^{19}$—, wherein $R^{19}$ represents a hydrogen atom or a lower alkyl group. The "lower alkyl group" is, for example, an alkyl group having 1 to 6 carbon atoms, such as a methyl group, an ethyl group, or a n-propyl group, and such a group is optionally substituted with one or more fluorine atoms.

In the formula, $R^{17}$, at each occurrence, is each independently a hydrogen atom, a fluorine atom or a lower fluoroalkyl group, preferably a fluorine atom. The "lower fluoroalkyl group" is, for example, a fluoroalkyl group having 1 to 6 carbon atoms, preferably 1 to 3 carbon atoms, preferably a perfluoroalkyl group having 1 to 3 carbon atoms, more preferably a trifluoromethyl group or a pentafluoroethyl group, further preferably a trifluoromethyl group.

In this embodiment, $X^1$ is preferably a group represented by formula: —$(O)_x$—$(CF_2)_y$—$(CH_2)_z$—, wherein x, y and z are as defined above, and the occurrence order of the respective repeating units in parentheses is not limited in the formula.

Examples of the group represented by formula: —$(O)_x$—$(CF_2)_y$—$(CH_2)_z$— include any group represented by —$(O)_x$—$(CH_2)_{z''}$—O—$[(CH_2)_{z'''}$—O—$]_{z''''}$, and —$(O)_x$—$(CF_2)_{y''}$—$(CH_2)_{z''}$—O—$[(CH_2)_{z'''}$—O—$]_{z''''}$, wherein x' is 0 or 1, y'', z'' and z''' are each independently an integer of 1 to 10, and z'''' is 0 or 1. Herein, a left end of such a group is bonded to PFPE.

In another preferable embodiment, $X^1$ is —O—$CFR^{20}$—$(CF_2)_{e'}$—.

$R^{20}$ each independently represents a fluorine atom or a lower fluoroalkyl group. The lower fluoroalkyl group is, for example, a fluoroalkyl group having 1 to 3 carbon atoms, preferably a perfluoroalkyl group having 1 to 3 carbon atoms, more preferably a trifluoromethyl group or a pentafluoroethyl group, further preferably a trifluoromethyl group.

Each e' is independently 0 or 1.

In one specific example, $R^{20}$ is a fluorine atom and e' is 1.

In still another embodiment, examples of the $X^1$ group include the following groups:

[Formula 8]

wherein
$R^{41}$ each independently represents a hydrogen atom, an alkyl group having 1 to 6 carbon atoms, or a $C_{1-6}$ alkoxy group, preferably a methyl group;
any number of the Ts in each $X^1$ group is the following group bonded to PFPE as a molecular backbone:
—$CH_2O(CH_2)_2$—,
—$CH_2O(CH_2)_3$—,
—$CF_2O(CH_2)_3$—,
—$CH_2$—,
$(CH_2)_2$—,
$(CH_2)_3$—,
$(CH_2)_4$—,
—CONH—$(CH_2)_2$—,
—CON($CH_3$)—$(CH_2)_3$—,
—CON(Ph)-$(CH_2)_3$—, wherein Ph means phenyl, or

[Formula 9]

wherein $R^{42}$ each independently represents a hydrogen atom, a $C_{1-6}$ alkyl group or a $C_{1-6}$ alkoxy group, preferably a methyl group or a methoxy group, more preferably a methyl group, some other of the Ts is —(CH₂)ₙ″— (n″ is an integer of 2 to 6) bonded to an opposite group to PFPE as a molecular backbone, and the remaining T, if present, may be independently a methyl group, a phenyl group, a $C_{1-6}$ alkoxy group, or a radical scavenging group or an UV absorbing group. Also in the embodiment, a left portion and a right portion of the group designated as $X^1$ are bonded to the group represented by PFPE and the group in parentheses with α1, respectively.

The radical scavenging group is not limited as long as it may scavenge a radical generated by light irradiation, and examples thereof include a residue of benzophenones, benzotriazoles, benzoates, phenyl salicylates, crotonic acids, malonates, organoacrylates, hindered amines, hindered phenols, or triazines.

The UV absorbing group is not limited as long as it can absorb ultraviolet light, and examples thereof include a residue of benzotriazoles, hydroxybenzophenones, esters of substituted and unsubstituted benzoic acid or salicylic acid compounds, acrylates or alkoxy cinnamates, oxamides, oxanilides, benzoxazinones, and benzoxazoles.

In a preferable embodiment, examples of a preferable radical scavenging group or an UV absorbing group include

[Formula 10]

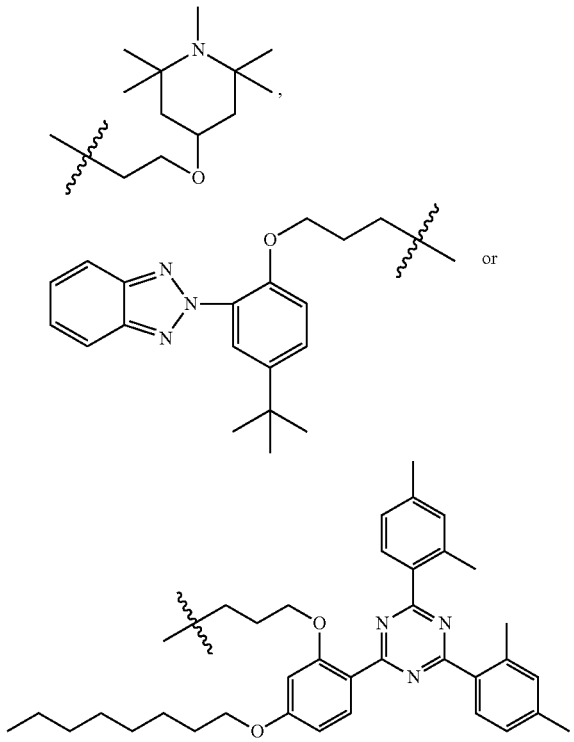

In this embodiment, $X^1$ (and, the following $X^3$, $X^5$ and $X^7$) may be a tri- to decavalent organic group.

In the formulae, $X^2$, at each occurrence, each independently represents a single bond or a divalent organic group. $X^2$ is preferably an alkylene group having 1 to 20 carbon atoms, more preferably —(CH₂)ᵤ—, wherein u is an integer of 0 to 2.

In the formulae, t is each independently an integer of 1 to 10. In a preferable embodiment, t is an integer of 1 to 6. In another preferable embodiment, t is an integer of 2 to 10, preferably an integer of 2 to 6.

A preferable compound represented by formula (A) is a compound represented by the following formula (A'):

[Formula 11]

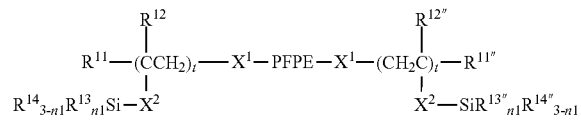

(A')

wherein:
PFPE, at each occurrence, is each independently a group represented by formula:

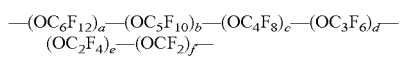

wherein a, b, c, d, e and f are each independently an integer of 0 or more and 200 or less, the sum of a, b, c, d, e and f is at least 1, and the occurrence order of the respective repeating units in parentheses with a, b, c, d, e or f is not limited in the formula;

$R^{13}$, at each occurrence, each independently represents a hydroxyl group or a hydrolyzable group;

$R^{14}$, at each occurrence, each independently represents a hydrogen atom or an alkyl group having 1 to 22 carbon atoms;

$R^{11}$, at each occurrence, each independently represents a hydrogen atom or a halogen atom;

$R^{12}$, at each occurrence, each independently represents a hydrogen atom or a lower alkyl group;

$R^{11″}$, $R^{12″}$, $R^{13″}$, $R^{14″}$ have the same meanings as $R^{11}$, $R^{12}$, $R^{13}$, $R^{14}$, respectively;

n1 is an integer of 1 to 3, preferably 3;

$X^1$, at each occurrence, is each independently —O—CFR²⁰—(CF₂)ₑ′—;

$R^{20}$, at each occurrence, is each independently a fluorine atom or a lower fluoroalkyl group;

e', at each occurrence, is each independently 0 or 1;

$X^2$ is —(CH₂)ᵤ—;

u, at each occurrence, is each independently an integer of 0 to 2; and t, at each occurrence, is each independently an integer of 2 to 10.

Such any compound represented by formula (A) can be obtained by, for example, introducing iodine into an end of a perfluoropolyether derivative corresponding to a -PFPE-portion, as a raw material, and reacting a vinyl monomer corresponding to —CH₂CR¹²(X²SiR¹³ₙ₁R¹⁴₃₋ₙ₁)—.

Formula (B):

[Formula 12]

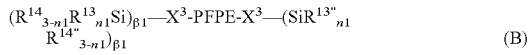

(B)

In formula (B), PFPE, $R^{13}$, $Rn^{13″}$, $R^{14}$, $R^{14″}$ and n1 have the same meanings as described with respect to the formula (A).

In formula (B), the Si atom bonded to at least one group selected from the group consisting of a hydroxyl group and a hydrolyzable group indicates a Si atom included in (SiR¹³ₙ₁R¹⁴₃₋ₙ₁) or (—SiR¹³″ₙ₁R¹⁴″₃₋ₙ₁) where n1 is an integer of 1 to 3.

In the formulae, n1 with respect to each ($-SiR^{13}_{n1}R^{14}_{3-n1}$) unit or each ($-SiR^{13"}_{n1}R^{14"}_{3-n1}$) unit is independently an integer of 0 to 3, preferably 1 to 3, more preferably 3. In the formulae, at least two n1 are each an integer of 1 to 3, namely, there is not any case where all n1 are simultaneously 0. That is, at least two $R^{13}$ or $R^{13"}$ are present in the formulae. That is, at least two structures selected from the group consisting of a $-SiR^{13}_{n1}R^{14}_{3-n1}$ structure (namely, $-SiR^{13}$ portion) where n1 is 1 or more and a $-SiR^{13"}_{n1}R^{14"}_{3-n1}$ structure (namely, $-SiR^{13"}$ portion) where n1 is 1 or more are present in formula (B).

More preferably, at least one Si bonded to the hydroxyl group or the hydrolyzable group is present at each of both ends of a molecular backbone of the PFPE-containing silane compound, in formula (B). That is, at least one $SiR^{13}$ portion is present, and at least one $SiR^{13"}$ portion is present.

In the formulae, $X^3$ each independently represents a single bond or a 2-10 valent organic group. $X^3$ is understood to be a linker which links a perfluoropolyether portion (namely, -PFPE- portion) mainly providing water-repellency, surface lubricity, and the like, and a silane portion (specifically, $-SiR^{13}_{n1}R^{14}_{3-n1}$ or $-SiR^{13"}_{n1}R^{14"}_{3-n1}$) providing a binding ability to the base material, in any compound represented by formula (B). Accordingly, $X^3$ may be a single bond or any organic group as long as such any compound represented by formula (B) can be stably present. Herein, a left portion and a right portion of the structure designated as $X^3$ are bonded to the group represented by PFPE and the group in parentheses with β1, respectively.

In another embodiment, $X^3$ represents $X^e$. $X^e$ is as defined above.

In the formulae, β1 is an integer of 1 to 9, and may be varied depending on the valence of $X^3$. In formula (B), β1 corresponds to a value obtained by subtracting 1 from the value of the valence of $X^3$. In the case where $X^3$ is a single bond, β1 is 1.

$X^3$ is preferably a 2-7 valent, more preferably 2-4 valent, further preferably divalent organic group.

In one embodiment, $X^3$ is a 2-4 valent organic group, and β1 is 1 to 3.

In another embodiment, $X^3$ is a divalent organic group, and β1 is 1. In such a case, formula (B) is represented by the following formula (B').

[Formula 13]

$$R^{14}_{3-n1}R^{13}_{n1}Si-X^3\text{-PFPE-}X^3-SiR^{13"}_{n1}R^{14"}_{3-n1} \quad (B')$$

Examples of $X^3$ are not limited, and include the same as described with respect to X'.

In particular, preferable specific examples of $X^3$ include a single bond,
—CH$_2$OCH$_2$—,
—CH$_2$O(CH$_2$)$_2$—,
—CH$_2$O(CH$_2$)$_3$—,
—CH$_2$O(CH$_2$)
—CF$_2$—CH$_2$—O—CH$_2$—,
—CF$_2$—CH$_2$—O—(CH$_2$)$_2$—,
—CF$_2$—CH$_2$—O—(CH$_2$)$_3$—,
—CF$_2$—CH$_2$—O—(CH$_2$)$_6$—,
—CH$_2$O(CH$_2$)$_3$Si(CH$_3$)$_2$OSi(CH$_3$)$_2$(CH$_2$)$_2$—,
—CH$_2$O(CH$_2$)$_3$Si(CH$_3$)$_2$OSi(CH$_3$)$_2$OSi(CH$_3$)$_2$(CH$_2$)$_2$—,
—CH$_2$O(CH$_2$)$_3$Si(CH$_3$)$_2$O(Si(CH$_3$)$_2$O)$_2$Si(CH$_3$)$_2$(CH$_2$)$_2$—,
—CH$_2$O(CH$_2$)$_3$Si(CH$_3$)$_2$O(Si(CH$_3$)$_2$O)$_3$Si(CH$_3$)$_2$(CH$_2$)$_2$—,
—CH$_2$O(CH$_2$)$_3$Si(CH$_3$)$_2$O(Si(CH$_3$)$_2$O)$_{10}$Si(CH$_3$)$_2$(CH$_2$)$_2$—,
—CH$_2$O(CH$_2$)$_3$Si(CH$_3$)$_2$O(Si(CH$_3$)$_2$O)$_{20}$Si(CH$_3$)$_2$(CH$_2$)$_2$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CF$_2$CF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
—CH$_2$OCH$_2$CHFCF$_2$OCF$_2$—,
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$)CF$_2$OCF$_2$—,
—CH$_2$OCH$_2$CHFCF$_2$OCF(CF$_3$)CF$_2$OCF$_2$CF$_2$—,
—CH$_2$OCH$_2$CHFCF$_2$OCF(CF$_3$)CF$_2$OCF$_2$CF$_2$CF$_2$—,
—CH$_2$OCF$_2$CHFOCF$_2$CF$_2$CF$_2$—C(O)NH—CH$_2$—,
—CH$_2$OCH$_2$ (CH$_2$)$_7$CH$_2$Si(OCH$_3$)$_2$OSi(OCH$_3$)$_2$(CH$_2$)$_2$Si(OCH$_3$)$_2$OSi(OCH$_3$)$_2$(CH$_2$)$_2$—,
—CH$_2$OCH$_2$CH$_2$CH$_2$Si(OCH$_3$)$_2$OSi(OCH$_3$)$_2$(CH$_2$)$_3$—,
—CH$_2$OCH$_2$CH$_2$CH$_2$Si(OCH$_2$CH$_3$)$_2$OSi(OCH$_2$CH$_3$)$_2$(CH$_2$)$_3$—,
—CH$_2$OCH$_2$CH$_2$CH$_2$Si(OCH$_3$)$_2$OSi(OCH$_3$)$_2$(CH$_2$)$_2$—,
—CH$_2$OCH$_2$CH$_2$CH$_2$Si(OCH$_2$CH$_3$)$_2$OSi(OCH$_2$CH$_3$)$_2$(CH$_2$)$_2$—,
—(CH$_2$)$_2$—Si(CH$_3$)$_2$—(CH$_2$)$_2$—,
—CH$_2$—,
—(CH$_2$)$_2$—,
—(CH$_2$)$_3$—,
—(CH$_2$)$_4$—,
—(CH$_2$)$_5$—,
—(CH$_2$)$_6$—,
—CF$_2$—,
—(CF$_2$)$_2$—,
—CF$_2$—CH$_2$—,
—CF$_2$—(CH$_2$)$_2$—,
—CF$_2$—(CH$_2$)$_3$—,
—CF$_2$—(CH$_2$)$_4$—,
—CF$_2$—(CH$_2$)$_5$—,
—CF$_2$—(CH$_2$)$_6$—,
—CO—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—S—(CH$_2$)$_3$—,
—(CH$_2$)$_2$S(CH$_2$)$_3$—,
—CONH—(CH$_2$)$_3$Si(CH$_3$)$_2$OSi(CH$_3$)$_2$(CH$_2$)$_2$—, —CONH—(CH₂)₃Si(CH₃)₂OSi(CH₃)₂OSi(CH₃)₂(CH₂)₂—,
—CONH—(CH₂)₃Si(CH₃)₂O(Si(CH₃)₂O)₂Si(CH₃)₂(CH₂)₂—,
—CONH—(CH₂)₃Si(CH₃)₂O(Si(CH₃)₂O)₃Si(CH₃)₂(CH₂)₂—,
—CONH—(CH₂)₃Si(CH₃)₂O(Si(CH₃)₂O)₁₀Si(CH₃)₂(CH₂)₂—,
—CONH—(CH₂)₃Si(CH₃)₂O(Si(CH₃)₂O)₂OSi(CH₃)₂(CH₂)₂—,
—C(O)O—(CH₂)₃—,
—C(O) O—(CH₂)₆—,
—CH₂—O—(CH₂)₃—Si(CH₃)₂—(CH₂)₂—Si(CH₃)₂—(CH₂)₂—,
—CH₂—O—(CH₂)₃—Si(CH₃)₂—(CH₂)₂—Si(CH₃)₂—CH(CH₃)—,
—CH₂—O—(CH₂)₃—Si(CH₃)₂—(CH₂)₂—Si(CH₃)₂—(CH₂)₃—,
—CH₂—O—(CH₂)₃—Si(CH₃)₂—(CH₂)₂—Si(CH₃)₂—CH(CH₃)—CH₂—,
—OCH₂—,
—O(CH₂)₃—, and
—OCFHCF₂—

[Formula 14]

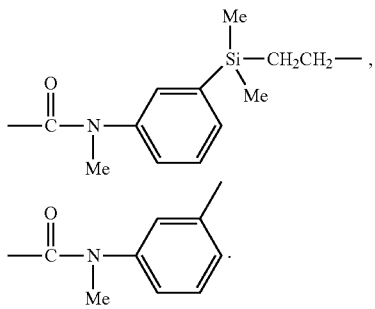

In particular, $X^3$ is preferably
—CH₂OCH₂—,
—CH₂O(CH₂)₂—,
—CH₂O(CH₂)₃—,
—CH₂O(CH₂)₆—,
—CF₂—CH₂—O—CH₂—,
—CF₂—CH₂—O—(CH₂)₂—,
—CF₂—CH₂—O—(CH₂)₃—,
—CF₂—CH₂—O—(CH₂)₆—,
—CH₂OCF₂CHFOCF₂—,
—CH₂OCF₂CHFOCF₂CF₂—,
—CH₂OCF₂CHFOCF₂CF₂CF₂—,
—CH₂OCH₂CF₂CF₂OCF₂—,
—CH₂OCH₂CF₂CF₂OCF₂CF₂—,
—CH₂OCH₂CF₂CF₂OCF₂CF₂CF₂—,
—CH₂OCH₂CF₂CF₂OCF(CF₃)CF₂OCF₂—,
—CH₂OCH₂CF₂CF₂OCF(CF₃)CF₂OCF₂CF₂—,
—CH₂OCH₂CF₂CF₂OCF(CF₃)CF₂OCF₂CF₂CF₂—,
—CH₂OCH₂CHFCF₂OCF₂—,
—CH₂OCH₂CHFCF₂OCF₂CF₂—,
—CH₂OCH₂CHFCF₂OCF₂CF₂CF₂—,
—CH₂OCH₂CHFCF₂OCF(CF₃)CF₂OCF₂—,
—CH₂OCH₂CHFCF₂OCF(CF₃)CF₂OCF₂CF₂—,
—CH₂OCH₂CHFCF₂OCF(CF₃)CF₂OCF₂CF₂CF₂—,
—CH₂OCF₂CHFOCF₂CF₂—C(O)NH—CH₂—,
—CF₂—CH₂OCF₂CHFOCF₂CF₂CF₂—C(O)NH—CH₂—,
—CH₂—,
—(CH₂)₂—,
—(CH₂)₃—,
—(CH₂)₄—,
—(CH₂)₅—,
—(CH₂)₆—,
—CF₂—,
—(CF₂)₂—,
—CF₂—CH₂—,
—CF₂—(CH₂)₂—,
—CF₂—(CH₂)₃—,
—CF₂—(CH₂)₄—,
—CF₂—(CH₂)₅—,
—CF₂—(CH₂)₆—,
—CONH—,
—CONH—CH₂—,
—CONH—(CH₂)₂—,
—CONH—(CH₂)₃—,
—CONH—(CH₂)₆—,
—CF₂CONH—,
—CF₂CONHCH₂—,
—CF₂CONH(CH₂)₂—,
—CF₂CONH(CH₂)₃—,
—CF₂CONH(CH₂)₆—,
—CON(CH₃)—(CH₂)₃—,
—CON(Ph)-(CH₂)₃—, wherein Ph means phenyl,
—CON(CH₃)—(CH₂)₆—,
—CON(Ph)-(CH₂)₆—, wherein Ph means phenyl,
—CF₂—CON(CH₃)—(CH₂)₃—,
—CF₂—CON(Ph)-(CH₂)₃—, wherein Ph means phenyl,
—CF₂—CON(CH₃)—(CH₂)₆—,
—CF₂—CON(Ph)-(CH₂)₆—, wherein Ph means phenyl,
—CONH—(CH₂)₂NH(CH₂)₃—,
—CONH—(CH₂)₆NH(CH₂)₃—,
—CH₂O—CONH—(CH₂)₃—,
—CH₂O—CONH—(CH₂)₆—,
—OCH₂—,
—O(CH₂)₃—,
—OCFHCF₂—.
In particular, $X^3$ is more preferably
—CH₂OCF₂CHFOCF₂CF₂CF₂—C(O)NH—CH₂—,
—CF₂—CH₂OCF₂CHFOCF₂CF₂CF₂—C(O)NH—CH₂—,
—CONH—,
—CONH—CH₂—,
—CONH—(CH₂)₂—,
—CONH—(CH₂)₃—,
—CONH—(CH₂)₆—,
—CF₂CONH—,
—CF₂CONHCH₂—,
—CF₂CONH(CH₂)₂—,
—CF₂CONH(CH₂)₃—,
—CF₂CONH(CH₂)₆—,
—CON(CH₃)—(CH₂)₃—,
—CON(Ph)-(CH₂)₃—, wherein Ph means phenyl,
—CON(CH₃)—(CH₂)₆—,
—CON(Ph)-(CH₂)₆—, wherein Ph means phenyl,
—CF₂—CON(CH₃)—(CH₂)₃—,
—CF₂—CON(Ph)-(CH₂)₃—, wherein Ph means phenyl,
—CF₂—CON(CH₃)—(CH₂)₆—,
—CF₂—CON(Ph)-(CH₂)₆—, wherein Ph means phenyl,
—CONH—(CH₂)₂NH(CH₂)₃—,
—CONH—(CH₂)₆NH(CH₂)₃—.
In another preferable embodiment, $X^3$ represents $X^{e'}$. $X^{e'}$ is as defined above.

In one embodiment, $X^{e'}$ is a single bond. In the present embodiment, PFPE and a group having a binding ability to the base material (namely, group in parentheses with β1 in (B)) are directly bonded.

In one embodiment, at least two Si each bonded to the hydroxyl group or the hydrolyzable group are present in formula (B). That is, at least two $SiR^{13}$ portions are present in formula (B).

A preferable compound represented by formula (B) is a compound represented by the following formula (B'):

[Formula 15]

$$R^{14}{}_{3\text{-}n1}R^{13}{}_{n1}Si\text{—}X^3\text{-PFPE-}X^3\text{—}SiR^{13''}{}_{n1}R^{14''}{}_{3\text{-}n1} \quad (B')$$

wherein:
PFPE, at each occurrence, is each independently a group represented by formula:

$$\text{—}(OC_6F_{12})_a\text{—}(OC_5F_{10})_b\text{—}(OC_4F_8)_c\text{—}(OC_3F_6)_d\text{—}(OC_2F_4)_e\text{—}(OCF_2)_f\text{—}.$$

wherein a, b, c, d, e and f are each independently an integer of 0 or more and 200 or less, the sum of a, b, c, d, e and f is at least 1, and the occurrence order of the respective repeating units in parentheses with a, b, c, d, e or f is not limited in the formula;
$R^{13}$, at each occurrence, each independently represents a hydroxyl group or a hydrolyzable group;
$R^{14}$, at each occurrence, each independently represents a hydrogen atom or an alkyl group having 1 to 22 carbon atoms;
$R^{13''}$ and $R^{14''}$ have the same meanings as $R^{13}$ and $R^{14}$, respectively;
n1 is an integer of 1 to 3, preferably 3; and
$X^3$ is $\text{—}CH_2O(CH_2)\text{—}CH_2O(CH_2)_3\text{—}$ or $\text{—}CH_2O(CH_2)_6\text{—}$.

Such any compound represented by formula (B) can be produced by a known method, for example, a method described in JP 2013-117012 A, or an improved method thereof.

Formula (C):

[Formula 16]

$$(R^c{}_{m1}R^b{}_{l1}R^a{}_{k1}Si)_{\gamma1}\text{—}X^5\text{-PFPE-}X^5\text{—}(SiR^{a''}{}_{k1}R^{b''}{}_{l1}R^{c''}{}_{m1})_{\gamma1} \quad (C)$$

In formula (C), PFPE is as defined above.

In the formula, $X^5$ each independently represents a single bond or a 2-10 valent organic group. $X^5$ is understood to be a linker which links a perfluoropolyether portion (namely, -PFPE- portion) mainly providing water-repellency, surface lubricity, and the like, and a silane portion (specifically, $\text{—}SiR^a{}_{k1}R^b{}_{l1}R^c{}_{m1}$ group or $\text{—}SiR^{a''}{}_{k1}R^{b''}{}_{l1}R^{c''}{}_{m1}$ group) providing a binding ability to the base material, in any compound represented by formula (C). Accordingly, $X^5$ may be a single bond or any organic group as long as such any compound represented by formula (C) can be stably present. Herein, a left portion and a right portion of the structure designated as $X^5$ are bonded to the group represented by PFPE and the group in parentheses with γ1, respectively.

In another embodiment, $X^5$ represents $X^e$. $X^e$ is as defined above.

In the formula, γ1 is an integer of 1 to 9, and γ1 may be varied depending on the valence of $X^5$. In formula (C), γ1 corresponds to a value obtained by subtracting 1 from the value of the valence of $X^5$.

$X^5$ is preferably a 2-7 valent, more preferably 2-4 valent, further preferably divalent organic group.

In one embodiment, $X^5$ is a 2-4 valent organic group, and γ1 is 1 to 3.

In another embodiment, $X^5$ is a divalent organic group, and γ1 is 1. In such a case, formula (C) is represented by the following formula (C').

[Formula 17]

$$R^c{}_{m1}R^b{}_{l1}R^a{}_{k1}Si\text{—}X^5\text{-PFPE-}X^5\text{—}SiR^{a''}{}_{k1}R^{b''}{}_{l1}R^{c''}{}_{m1} \quad (C')$$

Examples of $X^5$ are not limited, and include the same as described with respect to $X^1$.

In particular, preferable specific examples of $X^5$ include a single bond,
—$CH_2OCH_2$—,
—$CH_2O(CH_2)_2$—,
—$CH_2O(CH_2)_3$—,
—$CH_2O(CH_2)_6$—,
—$CF_2$—$CH_2$—O—$CH_2$—,
—$CF_2$—$CH_2$—O—$(CH_2)_2$—,
—$CF_2$—$CH_2$—O—$(CH_2)_3$—,
—$CF_2$—$CH_2$—O—$(CH_2)_6$—,
—$CH_2O(CH_2)_3Si(CH_3)_2OSi(CH_3)_2(CH_2)_2$—,
—$CH_2O(CH_2)_3Si(CH_3)_2OSi(CH_3)_2OSi(CH_3)_2(CH_2)_2$—,
—$CH_2O(CH_2)_3Si(CH_3)_2O(Si(CH_3)_2O)_2Si(CH_3)_2(CH_2)_2$—,
—$CH_2O(CH_2)_3Si(CH_3)_2O(Si(CH_3)_2O)_3Si(CH_3)_2(CH_2)_2$—,
—$CH_2O(CH_2)_3Si(CH_3)_2O(Si(CH_3)_2O)_{10}Si(CH_3)_2(CH_2)_2$—,
—$CH_2O(CH_2)_3Si(CH_3)_2O(Si(CH_3)_2O)_{20}Si(CH_3)_2(CH_2)_2$—,
—$CH_2OCF_2CHFOCF_2$—,
—$CH_2OCF_2CHFOCF_2CF_2$—,
—$CH_2OCF_2CHFOCF_2CF_2CF_2$—,
—$CH_2OCH_2CF_2CF_2OCF_2$—,
—$CH_2OCH_2CF_2CF_2OCF_2CF_2$—,
—$CH_2OCH_2CF_2CF_2OCF_2CF_2CF_2$—,
—$CH_2OCH_2CF_2CF_2OCF(CF_3)CF_2OCF_2$—,
—$CH_2OCH_2CF_2CF_2OCF(CF_3)CF_2OCF_2CF_2$—,
—$CH_2OCH_2CF_2CF_2OCF(CF_3)CF_2OCF_2CF_2CF_2$—,
—$CH_2OCH_2CHFCF_2OCF_2$—,
—$CH_2OCH_2CHFCF_2OCF_2CF_2$—,
—$CH_2OCH_2CHFCF_2OCF_2CF_2CF_2$—,
—$CH_2OCH_2CHFCF_2OCF(CF_3)CF_2OCF_2$—,
—$CH_2OCH_2CHFCF_2OCF(CF_3)CF_2OCF_2CF_2$—,
—$CH_2OCH_2CHFCF_2OCF(CF_3)CF_2OCF_2CF_2CF_2$—,
—$CH_2OCF_2CHFOCF_2CF_2CF_2$—C(O)NH—$CH_2$—,
—$CH_2OCH_2$ $(CH_2)_7CH_2Si(OCH_3)_2OSi(OCH_3)_2(CH_2)_2Si(OCH_3)_2OSi(OCH_3)_2(CH_2)_2$—,
—$CH_2OCH_2CH_2CH_2Si(OCH_3)_2OSi(OCH_3)_2(CH_2)_3$—,
—$CH_2OCH_2CH_2CH_2Si(OCH_2CH_3)_2OSi(OCH_2CH_3)_2(CH_2)_3$—,
—$CH_2OCH_2CH_2CH_2Si(OCH_3)_2OSi(OCH_3)_2(CH_2)_2$—,
—$CH_2OCH_2CH_2CH_2Si(OCH_2CH_3)_2OSi(OCH_2CH_3)_2(CH_2)_2$—,
—$(CH_2)_2$—$Si(CH_3)_2$—$(CH_2)_2$—,
—$CH_2$—,
—$(CH_2)_2$—,
—$(CH_2)_3$—,
—$(CH_2)_4$—,
—$(CH_2)_5$—,
—$(CH_2)_6$—,
—$CF_2$—,
—$(CF_2)_2$—,
—$CF_2$—$CH_2$—,
—$CF_2$—$(CH_2)_2$—,
—$CF_2$—$(CH_2)_3$—, —CF$_2$—(CH$_2$)$_4$—,
—CF$_2$—(CH$_2$)$_5$—,
—CF$_2$—(CH$_2$)$_6$—,
—CO—
—CONH—
—CONH—CH$_2$—,
—CONH—(CH$_2$)$_2$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CONH—(CH$_2$)$_3$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—S—(CH$_2$)$_3$—,
—(CH$_2$)$_2$S(CH$_2$)$_3$—,
—CONH—(CH$_2$)$_3$Si(CH$_3$)$_2$OSi(CH$_3$)$_2$(CH$_2$)$_2$—,
—CONH—(CH$_2$)$_3$Si(CH$_3$)$_2$OSi(CH$_3$)$_2$OSi(CH$_3$)$_2$(CH$_2$)$_2$—,
—CONH—(CH$_2$)$_3$Si(CH$_3$)$_2$O(Si(CH$_3$)$_2$O)$_2$Si(CH$_3$)$_2$(CH$_2$)$_2$—,
—CONH—(CH$_2$)$_3$Si(CH$_3$)$_2$O(Si(CH$_3$)$_2$O)$_3$Si(CH$_3$)$_2$(CH$_2$)$_2$—,
—CONH—(CH$_2$)$_3$Si(CH$_3$)$_2$O(Si(CH$_3$)$_2$O)$_{10}$Si(CH$_3$)$_2$(CH$_2$)$_2$—,
—CONH—(CH$_2$)$_3$Si(CH$_3$)$_2$O(Si(CH$_3$)$_2$O)$_2$OSi(CH$_3$)$_2$(CH$_2$)$_2$—,
—C(O) O—(CH$_2$)$_3$—,
—C(O) O—(CH$_2$)$_6$—,
—CH$_2$—O—(CH$_2$)$_3$—Si(CH$_3$)$_2$—(CH$_2$)$_2$—Si(CH$_3$)$_2$—(CH$_2$)$_2$—,
—CH$_2$—O—(CH$_2$)$_3$—Si(CH$_3$)$_2$—(CH$_2$)$_2$—Si(CH$_3$)$_2$—CH(CH$_3$)—,
—CH$_2$—O—(CH$_2$)$_3$—Si(CH$_3$)$_2$—(CH$_2$)$_2$—Si(CH$_3$)$_2$—(CH$_2$)$_3$—,
—CH$_2$—O—(CH$_2$)$_3$—Si(CH$_3$)$_2$—(CH$_2$)$_2$—Si(CH$_3$)$_2$—CH(CH$_3$)—CH$_2$—,
—OCH$_2$—,
—O(CH$_2$)$_3$—, and
—OCFHCF$_2$—

[Formula 18]

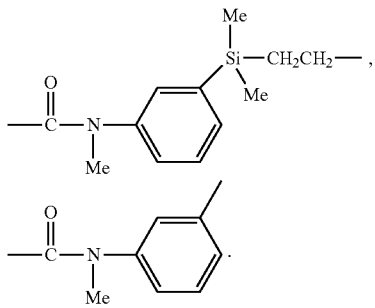

In particular, X$^5$ is preferably
—CH$_2$OCH$_2$—,
—CH$_2$O(CH$_2$)$_2$—,
—CH$_2$O(CH$_2$)$_3$—,
—CH$_2$O(CH$_2$)$_6$—,
—CF$_2$—CH$_2$—O—CH$_2$—,
—CF$_2$—CH$_2$—O—(CH$_2$)$_2$—,
—CF$_2$—CH$_2$—O—(CH$_2$)$_3$—,
—CF$_2$—CH$_2$—O—(CH$_2$)$_6$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CF$_2$CF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
—CH$_2$OCH$_2$CHFCF$_2$OCF$_2$—,
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$)CF$_2$OCF$_2$—,
—CH$_2$OCH$_2$CHFCF$_2$OCF(CF$_3$)CF$_2$OCF$_2$CF$_2$—,
—CH$_2$OCH$_2$CHFCF$_2$OCF(CF$_3$)CF$_2$OCF$_2$CF$_2$CF$_2$—,
—CH$_2$OCF$_2$CHFOCF$_2$CF$_2$CF$_2$—C(O)NH—CH$_2$—,
—CF$_2$—CH$_2$OCF$_2$CHFOCF$_2$CF$_2$CF$_2$—C(O)NH—CH$_2$—,
—CH$_2$—,
—(CH$_2$)$_2$—,
—(CH$_2$)$_3$—,
—(CH$_2$)$_4$—,
—(CH$_2$)$_5$—,
—(CH$_2$)$_6$—,
—CF$_2$—,
—(CF$_2$)$_2$—,
—CF$_2$—CH$_2$—,
—CF$_2$—(CH$_2$)$_2$—,
—CF$_2$—(CH$_2$)$_3$—,
—CF$_2$—(CH$_2$)$_4$—,
—CF$_2$—(CH$_2$)$_5$—,
—CF$_2$—(CH$_2$)$_6$—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—OCH$_2$—,
—O(CH$_2$)$_3$—,
—OCFHCF$_2$—.

In particular, $X^5$ is more preferably
—$CH_2OCF_2CHFOCF_2CF_2CF_2$—C(O)NH—$CH_2$—,
—$CF_2$—$CH_2OCF_2CHFOCF_2CF_2CF_2$—C(O)NH—$CH_2$—,
—CONH—,
—CONH—$CH_2$—,
—CONH—$(CH_2)_2$—,
—CONH—$(CH_2)_3$—,
—CONH—$(CH_2)_6$—,
—$CF_2$CONH—,
—$CF_2$CONH$CH_2$—,
—$CF_2$CONH$(CH_2)_2$—,
—$CF_2$CONH$(CH_2)_3$—,
—$CF_2$CONH$(CH_2)_6$—,
—CON($CH_3$)—$(CH_2)_3$—,
—CON(Ph)-$(CH_2)_3$—, wherein Ph means phenyl,
—CON($CH_3$)—$(CH_2)_6$—,
—CON(Ph)-$(CH_2)_6$—, wherein Ph means phenyl,
—$CF_2$—CON($CH_3$)—$(CH_2)_3$—,
—$CF_2$—CON(Ph)-$(CH_2)_3$—, wherein Ph means phenyl,
—$CF_2$—CON($CH_3$)—$(CH_2)_6$—,
—$CF_2$—CON(Ph)-$(CH_2)_6$—, wherein Ph means phenyl,
—CONH—$(CH_2)_2$NH$(CH_2)_3$—,
—CONH—$(CH_2)_6$NH$(CH_2)_3$—.

In another preferable embodiment, $X^5$ represents $X^{e'}$. $X^{e'}$ is as defined above.

In one embodiment, $X^{e'}$ is a single bond. In the present embodiment, PFPE and a group having a binding ability to the base material (namely, group in parentheses with γ1 in formula (C)) are directly bonded.

In the formula, $R^a$, at each occurrence, each independently represents —$Z^3$—$SiR^{71}_{p1}R^{72}_{q1}R^{73}_{r1}$.

In the formula, $Z^3$, at each occurrence, each independently represents an oxygen atom or a divalent organic group.

$Z^3$ is preferably a divalent organic group, and does not encompass any group which is taken together with a Si atom at an end of a molecular backbone in formula (C) (Si atom to which $R^a$ is bonded) to form a siloxane bond.

$Z^3$ is preferably a $C_{1-6}$ alkylene group, —$(CH_2)_g$—O—$(CH_2)_h$—, wherein g is an integer of 1 to 6, h is an integer of 1 to 6), or -phenylene-$(CH_2)_i$—, wherein i is an integer of 0 to 6), more preferably a $C_{1-3}$ alkylene group. Such a group is optionally substituted with one or more substituents selected from, for example, a fluorine atom, a $C_{1-6}$ alkyl group, a $C_{2-6}$ alkenyl group and a $C_{2-6}$ alkynyl group. $Z^3$ is more preferably a linear or branched alkylene group, further preferably a linear alkylene group from the viewpoint of particularly favorable ultraviolet durability. The number of carbon atoms constituting the alkylene group of $Z^3$ is preferably in the range from 1 to 6, more preferably in the range from 1 to 3. The alkylene group is as described above.

In the formulae, $R^{71}$, at each occurrence, each independently represents $R^{a'}$. $R^{a'}$ is as defined for $R^a$.

The number of Si linearly linked via a $Z^3$ group is at most 5 in $R^a$. That is, in the case where at least one $R^{71}$ is present in $R^a$, two or more Si atoms linearly linked via a $Z^3$ group are present in $R^a$, and the number of such Si atoms linearly linked via a $Z^3$ group is at most 5. Herein, the "number of Si atoms linearly linked via a $Z^3$ group in $R^{a}$" is equal to the number of repetitions of —$Z^3$—Si— linearly linked in $R^a$.

One example is represented below, where Si atoms are linked via a $Z^3$ group in $R^a$.

[Formula 19]

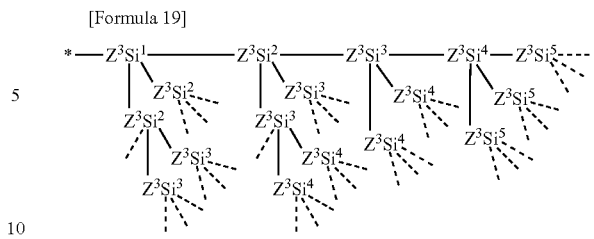

In the formula, "*" means a site bonded to Si of a main chain, and " . . . " means that a predetermined group other than $Z^3$Si is bonded, namely, " . . . " means a position at which repeating of $Z^3$Si is terminated in the case where all three bonds of a Si atom are " . . . ". The superscript number in Si means the number of occurrence of Si linearly linked via a $Z^3$ group when counted from "*". That is, a chain where repeating of $Z^3$Si is terminated at Si† is a chain where the "number of Si atoms linearly linked via a $Z^3$ group in $R^{a}$" is 2, and similarly, chains where repeating of $Z^3$Si is terminated at $Si^3$, $Si^4$ and $Si^5$ mean chains where the "number of Si atoms linearly linked via a $Z^3$ group in $R^{a}$" is 3, 4 and 5, respectively. As clear from the formula, a plurality of $Z^3$Si chains are present in $R^a$, and all the chains do not necessarily have the same length, and, for example, may each have any length.

In a preferable embodiment, the "number of Si atoms linearly linked via a $Z^3$ group in $R^{a}$" is 1 (left formula) or 2 (right formula) in all chains, as represented below.

[Formula 20]

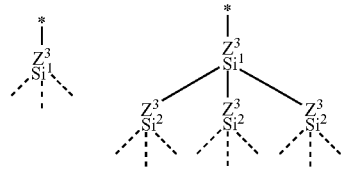

In one embodiment, the number of Si atoms linearly linked via a $Z^3$ group in $R^a$ is 1 or 2, preferably 1.

In the formulae, $R^{72}$, at each occurrence, each independently represents a hydroxyl group or a hydrolyzable group. The "hydrolyzable group" is as defined above.

Preferably, $R^{72}$ is —OR, wherein R represents a substituted or unsubstituted $C_{1-3}$ alkyl group, more preferably a methyl group.

In the formulae, $R^{73}$, at each occurrence, each independently represents a hydrogen atom or a lower alkyl group. The lower alkyl group is preferably an alkyl group having 1 to 20 carbon atoms, more preferably an alkyl group having 1 to 6 carbon atoms, further preferably a methyl group.

In the formulae, p1, at each occurrence, is each independently an integer of 0 to 3; q1, at each occurrence, is each independently an integer of 0 to 3; and r1, at each occurrence, is each independently an integer of 0 to 3, provided that the sum of p1, q1 and r1 with respect to (—$Z^3$—$SiR^{71}_{p1}R^{72}_{q1}R^{73}_{r1}$) is 3.

In a preferable embodiment, q1 in $R^{a'}$ ($R^a$ in the case where no $R^{a'}$ is present) at an end of $R^a$ is preferably 2 or more, for example, 2 or 3, more preferably 3.

In a preferable embodiment, at least one end of $R^a$ may be —Si(—$Z^3$—$SiR^{72}_{q1}R^{73}_{r1}$)$_2R^{72}_{q1}R^{73}_{r1'}$ (provided that at least any one of q1' and r1' is 1 and the other is 0), or —Si(—$Z^3$—$SiR^{72}_{q1}R^{73}_{r1}$)$_3$, preferably —Si(—$Z^3$—$SiR^{72}_{q1}R^{73}_{r1}$)$_3$ (wherein the total of q1 and r1 is 3). In the formula, a (—Z³—SiR⁷²_{q1}R⁷³_{r1}) unit is preferably (—Z³—SiR⁷²_3). In a further preferable embodiment, all ends of R$^a$ may be —Si(—Z³—SiR⁷²_{q1}R⁷³_{r1})_3, preferably —Si(—Z³—SiR⁷²_3)_3.

In a preferable embodiment, an end of a group represented by (SiR$^a_{k1}$R$^b_{l1}$R$^c_{m1}$) may be —Si(—Z³—SiR⁷²_{q1}R⁷³_{r1})_2 R$^b_{l1}$R$^c_{m1}$ (provided that any one of l1 and m1 is 1 and the other is 0), —Si—(—Z³—SiR⁷²_{q1}R⁷³_{r1})_2R⁷²_{q1'}R⁷³_{r1'} (provided that any one of q1' and r1' is 1 and the other is 0), or —Si(—Z³—SiR⁷²_{q1}R⁷³_{r1})_3, preferably —Si(—Z³—SiR⁷²_{q1}R⁷³_{r1})_3 (wherein the total of q1 and r1 is 3).

In the formulae, R$^{a''}$, at each occurrence, each independently represents —Z³—SiR⁷¹_{p1}R⁷²'_{q1}R⁷³_{r1}. Z³, R⁷¹, R⁷³, p1, q1 and r1 are as defined above. R⁷²' is as defined for R⁷².

In a preferable embodiment, at least one end of R$^{a''}$ may be —Si(—Z³—SiR⁷²''_{q1}R⁷³_{r1})_2R⁷²''_{q1'}R⁷³_{r1'} (provided that at least any one of q1' and r1' is 1 and the other is 0), or —Si(—Z³—SiR⁷²''_{q1}R⁷³_{r1})_3, preferably —Si(—Z³—SiR⁷²''_{q1}R⁷³_{r1})_3 (wherein the total of q1 and r1 is 3). In the formula, a (—Z³—SiR⁷²''_{q1}R⁷³_{r1}) unit is preferably (—Z³—SiR⁷²''_3). In a further preferable embodiment, all ends of R$^a$ may be —Si(—Z³—SiR⁷²''_{q1}R⁷³_{r1})_3, preferably —Si(—Z³—SiR⁷²''_3)_3.

In a preferable embodiment, an end of a group represented by (SiR$^{a''}_{k1}$R$^{b''}_{l1}$R$^{c''}_{m1}$) may be —Si(—Z³—SiR⁷²''_{q1}R⁷³_{r1})_2 R$^{b''}_{l1}$R$^{c''}_{m1}$ (provided that any one of l1 and m1 is 1 and the other is 0), —Si(—Z³—SiR⁷²''_{q1}R⁷³_{r1})_2R⁷²''_{q1'}R⁷³_{r1'} (provided that any one of q1' and r1' is 1 and the other is 0), or —Si(—Z³—SiR⁷²''_{q1}R⁷³_{r1})_3, preferably —Si(—Z³—SiR⁷²''_{q1}R⁷³_{r1})_3 (wherein the total of q1 and r1 is 3).

At least two Si atoms each bonded to the hydroxyl group or the hydrolyzable group are present in formula (C). That is, at least two structures selected from the group consisting of SiR⁷², SiR⁷²'', SiR$^b$ and SiR$^{b''}$ are present. R$^b$ and R$^{b''}$ are described below.

At least one Si bonded to the hydroxyl group or the hydrolyzable group is present at each of both ends of a molecular backbone of the PFPE-containing silane compound, in formula (C). That is, at least one SiR⁷² and/or SiR$^b$ structure is present, and at least one SiR⁷²'' and/or SiR$^{b''}$ structure is present.

In the formulae, R$^b$, at each occurrence, each independently represents a hydroxyl group or a hydrolyzable group.

R$^b$ preferably represents a hydroxyl group, —OR, —OCOR, —O—N=C(R)_2, —N(R)_2, —NHR, or halogen, wherein R represents a substituted or unsubstituted alkyl group having 1 to 4 carbon atoms, and R$^b$ more preferably represents —OR. Examples of R include unsubstituted alkyl groups such as a methyl group, an ethyl group, a propyl group, an isopropyl group, a n-butyl group and an isobutyl group; and substituted alkyl groups such as a chloromethyl group. Among them, an alkyl group, in particular, an unsubstituted alkyl group is preferable, and a methyl group or an ethyl group is more preferable. The hydroxyl group is not limited, and, may be generated by hydrolyzing the hydrolyzable group. More preferably, R$^b$ represents —OR, wherein R represents a substituted or unsubstituted $C_{1-3}$ alkyl group, more preferably a methyl group.

In the formulae, R$^{b''}$ is as defined for R$^b$.

In the formulae, R$^c$, at each occurrence, each independently represents a hydrogen atom or a lower alkyl group. The lower alkyl group is preferably an alkyl group having 1 to 20 carbon atoms, more preferably an alkyl group having 1 to 6 carbon atoms, further preferably a methyl group.

In the formulae, R$^{c''}$ is as defined for R$^c$.

In the formulae, k1, at each occurrence, is each independently an integer of 0 to 3; each l1, at each occurrence, is independently an integer of 0 to 3; and each m1, at each occurrence, is independently an integer of 0 to 3, provided that the sum of k1, l1 and m1 with respect to (SiR$^a_{k1}$R$^b_{l1}$R$^c_{m1}$) or with respect to (SiR$^{a''}_{k1}$R$^{b''}_{l1}$R$^{c''}_{m1}$) is 3.

In one embodiment, k1 is preferably 1 to 3, more preferably 3.

Such any compound represented by formula (C) can be synthesized as described in WO 2014/069592.

Formula (D):

[Formula 21]

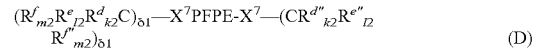

(D)

In formula (D), PFPE is as defined for formula (A).

In the formula, X⁷ each independently represents a single bond or a 2-10 valent organic group. X⁷ is understood to be a linker which links a perfluoropolyether portion (namely, -PFPE- portion) mainly providing water-repellency, surface lubricity, and the like, and a portion (namely, group in parentheses with δ1) providing a binding ability to the base material, in any compound represented by formula (D). Accordingly, X⁷ may be a single bond or any organic group as long as such any compound represented by formula (D) can be stably present. Herein, a left portion and a right portion of the structure designated as X⁷ are bonded to the group represented by PFPE and the group in parentheses with δ1, respectively.

In another embodiment, X⁷ represents X$^e$. X$^e$ is as defined above.

In the formulae, δ1 is an integer of 1 to 9, and δ1 may be varied depending on the valence of X⁷. In formula (D), δ1 corresponds to a value obtained by subtracting 1 from the valence of X⁷. In the case where X⁷ is a single bond, δ1 is 1.

X⁷ is preferably a 2-7 valent, more preferably 2-4 valent, further preferably divalent organic group.

In one embodiment, X⁷ is a 2-4 valent organic group, and δ1 is 1 to 3.

In another embodiment, X⁷ is a divalent organic group, and δ1 is 1. In such a case, formula (D) is represented by the following formula (D'):

[Formula 22]

(D')

Examples of X⁷ are not limited, and include the same as described with respect to X¹.

In particular, preferable specific examples of X⁷ include a single bond,
—CH_2OCH_2—,
—CH_2O(CH_2)_2—,
—CH_2O(CH_2)_3—,
—CH_2O(CH_2)_6—,
—CF_2—CH_2—O—CH_2—,
—CF_2—CH_2—O—(CH_2)_2—,
—CF_2—CH_2—O—(CH_2)_3—,
—CF_2—CH_2—O—(CH_2)_6—,
—CH_2O(CH_2)_3Si(CH_3)_2OSi(CH_3)_2(CH_2)_2—,
—CH_2O(CH_2)_3Si(CH_3)_2OSi(CH_3)_2OSi(CH_3)_2(CH_2)
—CH_2O(CH_2)_3Si(CH_3)_2O(Si(CH_3)_2O)_2Si(CH_3)_2(CH_2)_2 —,
—CH_2O(CH_2)_3Si(CH_3)_2O(Si(CH_3)_2O)_3Si(CH_3)_2(CH_2)_2 —,
—CH_2O(CH_2)_3Si(CH_3)_2O(Si(CH_3)_2O)_{10}Si(CH_3)_2 (CH_2)_2 —,
—CH_2O(CH_2)_3Si(CH_3)_2O(Si(CH_3)_2O)_{20}Si(CH_3)_2(CH_2)
—CH_2OCF_2CHFOCF_2—, —CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CF$_2$CF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
—CH$_2$OCH$_2$CHFCF$_2$OCF$_2$—,
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$)CF$_2$OCF$_2$—,
—CH$_2$OCH$_2$CHFCF$_2$OCF(CF$_3$)CF$_2$OCF$_2$CF$_2$—,
—CH$_2$OCH$_2$CHFCF$_2$OCF(CF$_3$)CF$_2$OCF$_2$CF$_2$CF$_2$—,
—CH$_2$OCF$_2$CHFOCF$_2$CF$_2$CF$_2$—C(O)NH—CH$_2$—,
—CH$_2$OCH$_2$ (CH$_2$)$_7$CH$_2$Si(OCH$_3$)$_2$OSi(OCH$_3$)$_2$(CH$_2$)$_2$ Si(OCH$_3$)$_2$OSi(OCH$_3$)$_2$(CH$_2$)$_2$—,
—CH$_2$OCH$_2$CH$_2$CH$_2$Si(OCH$_3$)$_2$OSi(OCH$_3$)$_2$ (CH$_2$)$_3$—,
—CH$_2$OCH$_2$CH$_2$CH$_2$Si(OCH$_2$CH$_3$)$_2$OSi(OCH$_2$CH$_3$)$_2$ (CH$_2$)$_3$—,
—CH$_2$OCH$_2$CH$_2$CH$_2$Si(OCH$_3$)$_2$OSi(OCH$_3$)$_2$ (CH$_2$)$_2$—,
—CH$_2$OCH$_2$CH$_2$CH$_2$Si(OCH$_2$CH$_3$)$_2$OSi(OCH$_2$CH$_3$)$_2$ (CH$_2$)$_2$—,
—(CH$_2$)$_2$—Si(CH$_3$)$_2$—(CH$_2$)$_2$—,
—CH$_2$—,
—(CH$_2$)$_2$—,
—(CH$_2$)$_3$—,
—(CH$_2$)$_4$—,
—(CH$_2$)$_5$—,
—(CH$_2$)$_6$—,
—CF$_2$—,
—(CF$_2$)$_2$—,
—CF$_2$—CH$_2$—,
—CF$_2$—(CH$_2$)$_2$—,
—CF$_2$—(CH$_2$)$_3$—,
—CF$_2$—(CH$_2$)$_4$—,
—CF$_2$—(CH$_2$)$_5$—,
—CF$_2$—(CH$_2$)$_6$—,
—CO—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—S—(CH$_2$)$_3$—,
—(CH$_2$)$_2$S(CH$_2$)$_3$—,
—CONH—(CH$_2$)$_3$Si(CH$_3$)$_2$OSi(CH$_3$)$_2$(CH$_2$)$_2$—,
—CONH—(CH$_2$)$_3$Si(CH$_3$)$_2$OSi(CH$_3$)$_2$OSi(CH$_3$)$_2$(CH$_2$)$_2$—,
—CONH—(CH$_2$)$_3$Si(CH$_3$)$_2$O(Si(CH$_3$)$_2$O)$_2$Si(CH$_3$)$_2$ (CH$_2$)$_2$—,
—CONH—(CH$_2$)$_3$Si(CH$_3$)$_2$O(Si(CH$_3$)$_2$O)$_3$Si(CH$_3$)$_2$ (CH$_2$)$_2$—,
—CONH—(CH$_2$)$_3$Si(CH$_3$)$_2$O(Si(CH$_3$)$_2$O)$_{10}$Si(CH$_3$)$_2$ (CH$_2$)$_2$—,
—CONH—(CH$_2$)$_3$Si(CH$_3$)$_2$O(Si(CH$_3$)$_2$O)$_2$OSi(CH$_3$)$_2$ (CH$_2$)$_2$—,
—C(O)O—(CH$_2$)$_3$—,
—C(O) O—(CH$_2$)$_6$—,
—CH$_2$—O—(CH$_2$)$_3$—Si(CH$_3$)$_2$—(CH$_2$)$_2$—Si(CH$_3$)$_2$—(CH$_2$)$_2$—,
—CH$_2$—O—(CH$_2$)$_3$—Si(CH$_3$)$_2$—(CH$_2$)$_2$—Si(CH$_3$)$_2$—CH(CH$_3$)—,
—CH$_2$—O—(CH$_2$)$_3$—Si(CH$_3$)$_2$—(CH$_2$)$_2$—Si(CH$_3$)$_2$—(CH$_2$)$_3$—,
—CH$_2$—O—(CH$_2$)$_3$—Si(CH$_3$)$_2$—(CH$_2$)$_2$—Si(CH$_3$)$_2$—CH(CH$_3$)—CH$_2$—,
—OCH$_2$—,
—O(CH$_2$)$_3$—, and
—OCFHCF$_2$—

[Formula 23]

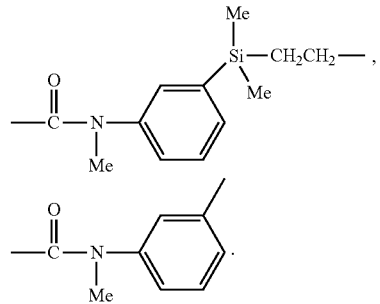

In particular, specific $X^7$ is more preferably
—CH$_2$OCH$_2$—,
—CH$_2$O(CH$_2$)$_2$—,
—CH$_2$O(CH$_2$)$_3$—,
—CH$_2$O(CH$_2$)$_6$—,
—CF$_2$—CH$_2$—O—CH$_2$—,
—CF$_2$—CH$_2$—O—(CH$_2$)$_2$—,
—CF$_2$—CH$_2$—O—(CH$_2$)$_3$—,
—CF$_2$—CH$_2$—O—(CH$_2$)$_6$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CF$_2$CF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
—CH$_2$OCH$_2$CHFCF$_2$OCF$_2$—,
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$)CF$_2$OCF$_2$—,
—CH$_2$OCH$_2$CHFCF$_2$OCF(CF$_3$)CF$_2$OCF$_2$CF$_2$—,
—CH$_2$OCH$_2$CHFCF$_2$OCF(CF$_3$)CF$_2$OCF$_2$CF$_2$CF$_2$—,
—CH$_2$OCF$_2$CHFOCF$_2$CF$_2$CF$_2$—C(O)NH—CH$_2$—,
—CF$_2$—CH$_2$OCF$_2$CHFOCF$_2$CF$_2$CF$_2$—C(O)NH—CH$_2$—,
—CH$_2$—,
—(CH$_2$)$_2$—, —(CH$_2$)$_3$—,
—(CH$_2$)$_4$—,
—(CH$_2$)$_5$—,
—(CH$_2$)$_6$—,
—CF$_2$—,
—(CF$_2$)$_2$—,
—CF$_2$—CH$_2$—,
—CF$_2$—(CH$_2$)$_2$—,
—CF$_2$—(CH$_2$)$_3$—,
—CF$_2$—(CH$_2$)$_4$—,
—CF$_2$—(CH$_2$)$_5$—,
—CF$_2$—(CH$_2$)$_6$—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—OCH$_2$—,
—O(CH$_2$)$_3$—,
—OCFHCF$_2$—.

In particular, X$^7$ is more preferably
—CH$_2$OCF$_2$CHFOCF$_2$CF$_2$CF$_2$—C(O)NH—CH$_2$—,
—CF$_2$—CH$_2$OCF$_2$CHFOCF$_2$CF$_2$CF$_2$—C(O)NH—CH$_2$—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—.

In a more preferable embodiment, X$^7$ represents X$^{e'}$. X$^{e'}$ is as defined above.

In one embodiment, X$^{e'}$ is a single bond. In the present embodiment, PFPE and a group having a binding ability to the base material (namely, group in parentheses with δ1 in formula (D)) are directly bonded. It is considered that such a structure is included to thereby strengthen a bonding force between PFPE and the group in parentheses with δ1. It is also considered that a carbon atom (namely, a carbon atom bonded to R$^d$, R$^e$ and R$^f$ or R$^{d''}$, R$^{e''}$ and R$^{f''}$ in the group in parentheses with δ1) directly bonded to PFPE is less biased in charge and, as a result, a nucleophilic reaction or the like hardly occurs at the carbon atom and the compound is stably bonded to the base material. Such a structure has the advantage of being capable of more enhancing friction durability of a layer formed by the PFPE silane compound.

In the formulae, R$^d$, at each occurrence, each independently represents —Z$^4$—CR$^{81}_{p2}$R$^{82}_{q2}$R$^{83}_{r2}$.

In the formulae, Z$^4$, at each occurrence, each independently represents an oxygen atom or a divalent organic group.

Z$^4$ is preferably a C$_{1-6}$ alkylene group, —(CH$_2$)$_g$—O—(CH$_2$)$_h$—, wherein g is an integer of 0 to 6, for example, an integer of 1 to 6, and h is an integer of 0 to 6, for example, an integer of 1 to 6, or -phenylene-(CH$_2$)$_i$—, wherein i is an integer of 0 to 6, more preferably a C$_{1-3}$ alkylene group. Such a group is optionally substituted with one or more substituents selected from, for example, a fluorine atom, a C$_{1-6}$ alkyl group, a C$_{2-6}$ alkenyl group and a C$_{2-6}$ alkynyl group.

In the formulae, R$^{81}$, at each occurrence, each independently represents R$^{d'}$. R$^{d'}$ is as defined for R$^d$.

The number of C linearly linked via a Z$^4$ group is at most 5 in R$^d$. That is, in the case where at least one R$^{81}$ is present in R$^d$, two or more C atoms linearly linked via a Z$^4$ group are present in R$^d$, and the number of such C atoms linearly linked via a Z$^4$ group is at most 5. Herein, the "number of C atoms linearly linked via a Z$^4$ group in R$^d$" is equal to the number of repeating units of —Z$^4$—C— linearly linked in R$^d$.

In a preferable embodiment, the "number of C atoms linearly linked via a Z$^4$ group in R$^d$" is 1 (left formula) or 2 (right formula) in all chains, as represented below.

[Formula 24]

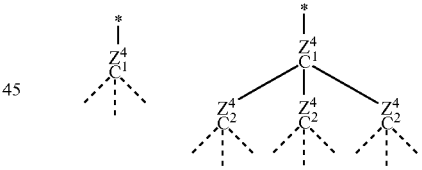

In one embodiment, the number of C atoms linearly linked via a Z$^4$ group in R$^d$ is 1 or 2, preferably 1.

In the formulae, R$^{82}$, at each occurrence, each independently represents —Y—SiR$^{85}_{n2}$R$^{86}_{3-n2}$.

Y, at each occurrence, each independently represents a divalent organic group.

In a preferable embodiment, Y is a C$_{1-6}$ alkylene group, —(CH$_2$)$_{g'}$—O—(CH$_2$)$_{h'}$—, wherein g' is an integer of 0 to 6, for example, an integer of 1 to 6, and h' is an integer of 0 to 6, for example, an integer of 1 to 6, or -phenylene-(CH$_2$)$_{i'}$—, wherein i' is an integer of 0 to 6. Such a group is optionally substituted with one or more substituents selected from, for example, a fluorine atom, a C$_{1-6}$ alkyl group, a C$_{2-6}$ alkenyl group and a C$_{2-6}$ alkynyl group.

In one embodiment, Y may be a C$_{1-6}$ alkylene group or -phenylene-(CH$_2$)$_{i'}$—. In the case where Y is any of the above groups, light resistance, in particular, ultraviolet resistance can be more enhanced.

$R^{85}$, at each occurrence, each independently represents a hydroxyl group or a hydrolyzable group.

Examples of the "hydrolyzable group" include the same as in formula (C).

Preferably, $R^{85}$ is —OR, wherein R represents a substituted or unsubstituted $C_{1-3}$ alkyl group, more preferably an ethyl group or a methyl group, in particular, a methyl group.

$R^{86}$, at each occurrence, each independently represents a hydrogen atom or a lower alkyl group. The lower alkyl group is preferably an alkyl group having 1 to 20 carbon atoms, more preferably an alkyl group having 1 to 6 carbon atoms, further preferably a methyl group.

n2 with respect to a $(-Y-SiR^{85}{}_{n2}R^{86}{}_{3-n2})$ unit or with respect to a $(-Y-SiR^{85'}{}_{n2}R^{86'}{}_{3-n2})$ unit independently represents an integer of 0 to 3, preferably an integer of 1 to 3, more preferably 2 or 3, particularly preferably 3. $R^{85''}$ and $R^{86''}$ are described below.

$R^{83}$, at each occurrence, each independently represents a hydrogen atom, a hydroxyl group or a lower alkyl group, preferably a hydrogen atom or a lower alkyl group. The lower alkyl group is preferably an alkyl group having 1 to 20 carbon atoms, more preferably an alkyl group having 1 to 6 carbon atoms, further preferably a methyl group.

In the formulae, p2, at each occurrence, is each independently an integer of 0 to 3; each q2, at each occurrence, is independently an integer of 0 to 3; and each r2, at each occurrence, is independently an integer of 0 to 3, provided that the sum of p2, q2 and r2 with respect to $(-Z^4-CR^{81}{}_{p2}R^{82}{}_{q2}R^{83}{}_{r2})$ or with respect to $(-Z^4-CR^{81}{}_{p2}R^{82'}{}_{q2}R^{83}{}_{r2})$ is 3. $R^{82''}$ is described below.

In a preferable embodiment, q2 in $R^{d'}$ ($R^d$ in the case where no $R^{d'}$ is present) at an end of $R^d$ is preferably 2 or more, for example, 2 or 3, more preferably 3.

In a preferable embodiment, at least one end of $R^d$ may be —C(—Y—SiR$^{85}{}_{n2}$R$^{86}{}_{3-n2}$)$_2$ (specifically, —C(—Y—SiR$^{85}{}_{n2}$R$^{86}{}_{3-n2}$)$_2$R$^{83}$) or —C(—Y—SiR$^{85}{}_{n2}$R$^{86}{}_{3-n2}$)$_3$, preferably —C(—Y—SiR$^{85}{}_{n2}$R$^{86}{}_{3-n2}$)$_3$. Here, n2 is an integer of 1 to 3. In the formulae, a $(-Y-SiR^{85}{}_{n2}R^{86}{}_{3-n2})$ unit is preferably $(-Y-SiR^{85}{}_3)$. In a further preferable embodiment, all ends of $R^d$ may be each —C(—Y—SiR$^{85}{}_{n2}$R$^{86}{}_{3-n2}$)$_3$, preferably —C(—Y—SiR$^{85}{}_3$)$_3$.

In a preferable embodiment, an end of a group represented by $(CR^d{}_{k2}R^e{}_{l2}R^f{}_{m2})$ is C(—Y—SiR$^{85}{}_{n2}$R$^{86}{}_{3-n2}$)$_2$R$^f$, C(—Y—SiR$^{85}{}_{n2}$R$^{86}{}_{3-n2}$)$_2$R$^{83}$ or C(—Y—SiR$^{85}{}_{n2}$R$^{86}{}_{3-n2}$)$_3$, preferably C(—Y—SiR$^{85}{}_{n2}$R$^{86}{}_{3-n2}$)$_3$. Here, n2 is an integer of 1 to 3. In the formulae, a $(-Y-SiR^{85}{}_{n2}R^{86}{}_{3-n2})$ unit is preferably $(-Y-SiR^{85}{}_3)$. In a further preferable embodiment, all ends of the group may be each C(—Y—SiR$^{85}{}_{n2}$R$^{86}{}_{3-n2}$)$_3$, preferably C(—Y—SiR$^{85}{}_3$)$_3$.

In the formulae, each $R^{e}$, at each occurrence, independently represents —Z$^4$—CR$^{81}{}_{p2}$R$^{82''}{}_{q2}$R$^{83}{}_{r2}$. Z$^4$, R$^{81}$, R$^{83}$, p2, q2 and r2 are as defined above. $R^{82''}$, at each occurrence, each independently represents —Y—SiR$^{85''}{}_{n2}$R$^{86''}{}_{3-n2}$. Here, Y and n2 are as defined above. $R^{83''}$ and $R^{86''}$ are as defined for $R^{85}$ and $R^{86}$, respectively.

In a preferable embodiment, q2 in $R^{d'}$ ($R^{d''}$ in the case where no $R^{d'}$ is present) at an end of $R^{d''}$ is preferably 2 or more, for example, 2 or 3, more preferably 3.

In a preferable embodiment, at least one end of $R^{d''}$ may be —C(—Y—SiR$^{85''}{}_{n2}$R$^{85''}{}_{3-n2}$)$_2$ (specifically, —C(—Y—SiR$^{85''}{}_{n2}$R$^{85''}{}_{3-n2}$)$_2$R$^{83}$) or —C(—Y—SiR$^{85''}{}_{n2}$R$^{86''}{}_{3-n2}$)$_3$, preferably —C(—Y—SiR$^{85''}{}_{n2}$R$^{85''}{}_{3-n2}$)$_3$. Here, n2 is an integer of 1 to 3. In the formulae, a $(-Y-SiR^{85''}{}_{n2}R^{85''}{}_{3-n2})$ unit is preferably $(-Y-SiR^{85''}{}_3)$. In a further preferable embodiment, all ends of $R^d$ may be each —C(—Y—SiR$^{85''}{}_{n2}$R$^{85''}{}_{3-n2}$)$_3$, preferably —C(—Y—SiR$^{85''}{}_3$)$_3$.

In a preferable embodiment, an end of a group represented by $(CR^{d''}{}_{k2}R^{e''}{}_{l2}R^{f''}{}_{m2})$ is C(—Y—SiR$^{85''}{}_{n2}$R$^{86''}{}_{3-n2}$)$_2$R$^f$, C(—Y—SiR$^{85''}{}_{n2}$R$^{86''}{}_{3-n2}$)$_2$R$^{83}$ or C(—Y—SiR$^{85''}{}_{n2}$R$^{85''}{}_{3-n2}$)$_3$, preferably C(—Y—SiR$^{85''}{}_{n2}$R$^{85''}{}_{3-n2}$)$_3$. Here, n2 is an integer of 1 to 3. In the formulae, a $(-Y-SiR^{85''}{}_{n2}R^{85''}{}_{3-n2})$ unit is preferably $(-Y-SiR^{85''}{}_3)$. In a further preferable embodiment, all ends of the group may be each C(—Y—SiR$^{85''}{}_{n2}$R$^{85''}{}_{3-n2}$)$_3$, preferably C(—Y—SiR$^{85''}{}_3$)$_3$.

In the formulae, each $R^e$, at each occurrence, independently represents —Y—SiR$^{85}{}_{n2}$R$^{85}{}_{3-n2}$. Here, Y, R$^{85}$, R$^{86}$ and n2 are as defined for R$^{82}$.

In the formulae, $R^{e''}$, at each occurrence, each independently represents —Y—SiR$^{85'}{}_{n2}$R$^{86''}{}_{3-n2}$. Here, R$^{85''}$, R$^{86''}$, Y, and n2 are as defined above.

In the formulae, $R^f$, at each occurrence, each independently represents a hydrogen atom, a hydroxyl group or a lower alkyl group. Preferably, $R^f$, at each occurrence, each independently represents a hydrogen atom or a lower alkyl group. The lower alkyl group is preferably an alkyl group having 1 to 20 carbon atoms, more preferably an alkyl group having 1 to 6 carbon atoms, further preferably a methyl group.

In the formulae, $R^{f''}$ is as defined for $R^f$.

In the formulae, k2, at each occurrence, is each independently an integer of 0 to 3; l2, at each occurrence, is each independently an integer of 0 to 3; and m2, at each occurrence, is each independently an integer of 0 to 3, provided that the sum of k2, l2 and m2 is 3.

In one embodiment, at least one k2 is 2 or 3, preferably 3.

In one embodiment, k2 is 2 or 3, preferably 3.

In one embodiment, l2 is 2 or 3, preferably 3.

In formula (D), one or more groups represented by —Y—SiR$^{85}$ and one or more groups represented by —Y—SiR$^{85''}$ are present. More preferably, one or more carbon atoms bonded to two or more —Y—SiR$^{85}$ are present, and one or more carbon atoms bonded to two or more —Y—SiR$^{85''}$ are present. That is, one or more groups represented by —C—(Y—SiR$^{85}{}_{n2}$R$^{86}{}_{3-n2}$)$_2$ and one or more groups represented by —C—(Y—SiR$^{85''}{}_{n2}$R$^{86''}{}_{3-n2}$)$_2$, wherein n2 is an integer of 1 to 3, are preferably present in formula (D).

In formula (D), n2 is an integer of 1 to 3 and at least one q2 is 2 or 3, or at least one l2 is 2 or 3.

In formula (D), at least two —Y—SiR$^{85}{}_{n2}$R$^{86}{}_{3-n2}$ groups or —Y—SiR$^{85''}{}_{n2}$R$^{86''}{}_{3-n2}$ groups are preferably present. In formula (D), one or more —Y—SiR$^{85}{}_{n2}$R$^{86}{}_{3-n2}$ groups and one or more —Y—SiR$^{85''}{}_{n2}$R$^{86''}{}_{3-n2}$ groups are more preferably present. That is, a group containing —SiR$^{85}$ and a group containing —SiR$^{85''}$ are preferably present at each of both ends of a molecular backbone of the PFPE-containing silane compound.

The compound represented by formula (D) can be produced by combining known methods.

In one embodiment, the PFPE-containing silane compound is a compound represented by formula (A).

In one embodiment, the PFPE-containing silane compound is a compound represented by formula (B).

In one embodiment, the PFPE-containing silane compound is a compound represented by formula (C).

In one embodiment, the PFPE-containing silane compound is a compound represented by formula (D).

In one embodiment, the PFPE-containing silane compound is represented by formula (A), (C) or (D).

In one embodiment, the PFPE-containing silane compound has two or more, preferably three or more Si atoms each having a hydroxyl group or a hydrolyzable group at at least one end.

The PFPE-containing silane compound may have a number average molecular weight of $5 \times 10^2$ to $1 \times 10^5$, without any limitation. In particular, the compound preferably has a number average molecular weight of 2,000 to 30,000, more preferably 2,500 to 12,000, further preferably 3,000 to 6,000. In the present invention, the number average molecular weight is defined as a value obtained by $^{19}$F-NMR measurement.

The PFPE-containing unsaturated compound is a PFPE group-containing compound having a carbon-carbon double bond at each of both molecular ends.

The PFPE-containing unsaturated compound is preferably a compound represented by the following formula (I).

$$CH_2=CH—R^{k1}\text{-PFPE-}R^{k1}—CH=CH_2 \quad (I)$$

In formula (I), PFPE is as defined above.

In formula (I), each $R^{k1}$, at each occurrence, independently represents a single bond or a divalent organic group.

$R^{k1}$ is understood to be a linker which links a perfluoro (poly)ether portion (namely, -PFPE- portion) mainly providing water-repellency, surface lubricity, and the like, and an alkenyl group. Accordingly, $R^{k1}$ may be a single bond or any organic group as long as the PFPE-containing compound can be stably present. Herein, a left portion and a right portion of $R^{k1}$ are bonded to the group represented by PFPE and the —CH=CH$_2$ portion of formula (I), respectively.

In one embodiment, $R^{k1}$ (provided that such a group is divalent) may be as defined for $X^e$ with respect to the PFPE-containing silane compound.

$R^{k1}$ is understood to be a linker which links a perfluoro (poly)ether portion (namely, -PFPE- portion) mainly providing water-repellency, surface lubricity, and the like, and an alkenyl group. Accordingly, $R^{k1}$ may be a single bond or any organic group as long as the PFPE-containing compound can be stably present.

In another embodiment, $R^{k1}$ may be $X^e$. $X^e$ represents a single bond or a divalent organic group, preferably represents a single bond or a divalent organic group having at least one selected from the group consisting of —C$_6$H$_4$— (namely, -phenylene-, hereinafter, representing a phenylene group), —CO— (carbonyl group), —NR$^4$— and —SO$_2$—. Each R$^4$ independently represents a hydrogen atom, a phenyl group, or a C$_{1-6}$ alkyl group (preferably a methyl group), preferably represents a hydrogen atom or a methyl group. Such —C$_6$H$_4$—, —CO—, —NR$^4$— or —SO$_2$— is preferably contained in a molecular backbone of the PFPE-containing unsaturated compound. The molecular backbone here represents a relatively longest binding chain in a molecule of the PFPE-containing unsaturated compound.

$X^e$ more preferably represents a single bond or a divalent organic group having at least one selected from the group consisting of —C$_6$H$_4$—, —CONR$^4$—, —CONR$^4$—C$_6$H$_4$—, —CO—, —CO—C$_6$H$_4$—, —SO$_2$NR$^4$—, —SO$_2$NR$^4$—C$_6$H$_4$—, —SO$_2$—, and —SO$_2$—C$_6$H$_4$—. Such —C$_6$H$_4$—, —CONR$^4$—, —CONR$^4$—C$_6$H$_4$—, —CO—, —CO—C$_6$H$_4$—, —SO$_2$NR$^4$—, —SO$_2$NR$^4$—C$_6$H$_4$—, —SO$_2$—, or —SO$_2$—C$_6$H$_4$— is preferably contained in a molecular backbone of the PFPE-containing unsaturated compound.

Examples of $R^{k1}$ are not limited, and include a divalent group represented by the following formula:

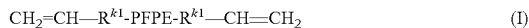
—(R$^{31}$)$_{p'}$—(X$^a$)$_{q'}$— wherein:
R$^{31}$ represents a single bond, —(CH$_2$)$_{s'}$—, or an o-, m- or p-phenylene group, preferably represents —(CH$_2$)$_{s'}$—, s' is an integer of 1 to 20, preferably an integer of 1 to 6, more preferably an integer of 1 to 3, still more preferably 1 or 2, X$^a$ represents, —(X$^{13}$)$_{l'}$—, X$^b$, at each occurrence, each independently represents a group selected from the group consisting of —O—, —S—, o-, m- or p-phenylene group, —C(O)O—, —Si(R$^{33}$)$_2$—, —(Si(R$^{33}$)$_2$O)$_{m'}$—Si(R$^{33}$)$_2$—, —CONR$^{34}$—, —O—CONR$^{34}$—, —NR$^{34}$— and —(CH$_2$)$_{n'}$—, R$^{33}$, at each occurrence, each independently represents a phenyl group, a C$_{1-6}$ alkyl group or a C$_{1-6}$ alkoxy group, preferably represents a phenyl group or a C$_{1-6}$ alkyl group, more preferably represents a methyl group, R$^{34}$, at each occurrence, each independently represents a hydrogen atom, a phenyl group, or a C$_{1-6}$ alkyl group (preferably a methyl group), m', at each occurrence, is each independently an integer of 1 to 100, preferably an integer of 1 to 20, n', at each occurrence, is each independently an integer of 1 to 20, preferably an integer of 1 to 6, more preferably an integer of 1 to 3, l' is an integer of 1 to 10, preferably an integer of 1 to 5, more preferably an integer of 1 to 3, p' is 0 or 1, and q' is 0 or 1, provided that at least one of p' and q' is 1, and the occurrence order of the respective repeating units in parentheses with p' or q' is not limited. Here, R$^{31}$ and X$^a$ (typically, any hydrogen atom in R$^{31}$ and X$^a$) are each optionally substituted with one or more substituents selected from a fluorine atom, a C$_{1-3}$ alkyl group and a C$_{1-3}$ fluoroalkyl group.

In one embodiment, l' is 1.

Preferably, $R^{k1}$ is —(R$^{31}$)$_{p'}$—(X$^a$)$_{q'}$—R$^{32}$—. R$^{32}$ represents a single bond, —(CH$_2$)$_{t'}$—, or an o-, m- or p-phenylene group, preferably —(CH$_2$)$_{t'}$—. Here, t' is an integer of 1 to 20, preferably an integer of 2 to 6, more preferably an integer of 2 to 3. In one embodiment, t' is an integer of 1 to 6, more preferably an integer of 1 to 3, for example, 1 or 2, more specifically 1. Here, R$^{32}$ (typically, any hydrogen atom in R$^{32}$) is optionally substituted with one or more substituents selected from a fluorine atom, a C$_{1-3}$ alkyl group and a C$_{1-3}$ fluoroalkyl group.

Preferably, $R^{k1}$ may be
a single bond,
a C$_{1-20}$ alkylene group,
—R$^{31}$—X$^c$—R$^{32}$—, or
—X$^d$—R$^{32}$—
wherein R$^{31}$ and R$^{32}$ are as defined above. Herein, such an alkylene group is a group having a —(C$_\delta$H$_{2\delta}$)— structure, and is optionally substituted or unsubstituted and is optionally linear or branched.

More preferably, $R^{k1}$ is
a single bond,
a C$_{1-20}$ alkylene group,
—(CH$_2$)$_{s'}$—X$^c$—,
—(CH$_2$)$_{s'}$—X$^c$—(CH$_2$)$_{t'}$—
—X$^d$—, or
—X$^d$—(CH$_2$)$_{t'}$—
wherein s' and t' are as defined above.

Further preferably, $R^{k1}$ is
—X$^f$—,
a —X$^f$—C$_{1-20}$ alkylene group,
—X$^f$—(CH$_2$)$_{s'}$—X$^c$—,
—X$^f$—(CH$_2$)$_{s'}$—X$^c$—(CH$_2$)$_{t'}$—
—X$^f$—X$^d$—, or
—X$^f$—X$^d$—(CH$_2$)$_{t'}$—
wherein s' and t' are as defined above.

In the formulae, $X^f$ is an alkylene group having 1 to 6 carbon atoms, preferably 1 to 4 carbon atoms, more preferably 1 to 2 carbon atoms, for example, a methylene group. Any hydrogen atom in $X^f$ is optionally substituted with one or more substituents selected from a fluorine atom, a $C_{1-3}$ alkyl group and a $C_{1-3}$ fluoroalkyl group, and is preferably substituted. $X^f$ may be linear or branched, and is preferably linear.

In the formulae, $X^c$ represents
—O—,
—S—,
—C(O)O—,
—CONR$^{34}$—,
—O—CONR$^{34}$—,
—Si(R$^{33}$)$_2$—,
(Si(R$^{33}$)$_2$O)$_{m'}$—Si(R$^{33}$)$_2$—,
—O—(CH$_2$)$_{u'}$—(Si(R$^{33}$)$_2$O)$_{m'}$—Si(R$^{33}$)$_2$—,
—O—(CH$_2$)$_{u'}$—Si(R$^{33}$)$_2$—O—Si(R$^{33}$)$_2$—CH$_2$CH$_2$—Si(R$^{33}$)$_2$—O—Si(R$^{33}$)$_2$—,
—O—(CH$_2$)$_{u'}$—Si(OCH$_3$)$_2$OSi(OCH$_3$)$_2$—,
—CONR$^{34}$—(CH$_2$)$_{u'}$—(Si(R$^{33}$)$_2$O)$_{m'}$—Si(R$^{33}$)$_2$—,
—CONR$^{34}$—(CH$_2$)$_{u'}$—N(R$^{34}$)—, or
—CONR$^{34}$-(o-, m- or p-phenylene)-Si(R$^{33}$)$_2$—
wherein R$^{33}$, R$^{34}$ and m' are as defined above, and
u' is an integer of 1 to 20, preferably an integer of 2 to 6, more preferably an integer of 2 to 3. $X^c$ is preferably —O—.

In the formulae, $X^d$ represents
—S—,
—C(O)O—,
—CONR$^{34}$—,
—CONR$^{34}$—(CH$_2$)$_{u'}$—(Si(R$^{33}$)$_2$O)$_{m'}$—Si(R$^{33}$)$_2$—,
—CONR$^{34}$—(CH$_2$)$_{u'}$—N(R$^{34}$)—, or
—CONR$^{34}$-(o-, m- or p-phenylene)-Si(R$^{33}$)$_2$—
wherein each symbol is as defined above.

Particularly preferably, $R^{k1}$ is a group represented by
—X$^f$—,
a —X$^f$-c$_{1-20}$ alkylene group,
—X$^f$—(CH$_2$)$_{s'}$—X$^c$—,
—X$^f$—(CH$_2$)$_{s'}$—X$^c$—(CH$_2$)$_{t'}$—
—X$^f$—X$^d$—, or
—X$^f$—X$^d$—(CH$_2$)$_{t'}$—
wherein X$^f$, s' and t' are as defined above;
$X^c$ represents —O—, or —CONR$^{34}$—,
$X^d$ represents —CONR$^{34}$—, and
R$^{34}$, at each occurrence, each independently represents a hydrogen atom, a phenyl group, or a $C_{1-6}$ alkyl group (preferably a methyl group).

In one embodiment, $R^{k1}$ is a group represented by
—X$^f$—(CH$_2$)$_{s'}$—X$^c$—,
—X$^f$—(CH$_2$)$_{s'}$—X$^c$—(CH$_2$)$_{t'}$—
—X$^f$—X$^d$—, or
—X$^f$—X$^d$—(CH$_2$)$_{t'}$—
wherein X$^f$, s' and t' are as defined above;
$X^c$ represents —O— or —CONR$^{34}$—,
$X^d$ represents —CONR$^{34}$—, and
R$^{34}$, at each occurrence, each independently represents a hydrogen atom, a phenyl group or a $C_{1-6}$ alkyl group (preferably a methyl group).

In one embodiment, $R^{k1}$ may be,
a single bond,
a $C_{1-20}$ alkylene group,
—(CH$_2$)$_{s'}$—X$^c$—(CH$_2$)$_{t'}$—, or
—X$^d$—(CH$_2$)$_{t'}$—
wherein each symbol is as defined above.

Preferably, $R^{k1}$ is
a single bond,
$C_{1-2}$ alkylene group,
—(CH$_2$)$_{s'}$—O—(CH$_2$)$_{t'}$—,
—(CH$_2$)$_{s'}$—(Si(R$^{33}$)$_2$O)$_{m'}$—Si(R$^{33}$)$_2$—(CH$_2$)$_{t'}$—,
—(CH$_2$)$_{s'}$—O—(CH$_2$)$_{u'}$—(Si(R$^{33}$)$_2$O)$_{m'}$—Si(R$^{33}$)$_2$—(CH$_2$)$_{t'}$—, or
—(CH$_2$)$_{s'}$—O—(CH$_2$)$_{t'}$—Si(R$^{33}$)$_2$—(CH$_2$)$_{u'}$—Si(R$^{33}$)$_2$—(C$_v$H$_{2v}$)—
wherein R$^{33}$, m', s', t' and u' are as defined above, and v is an integer of 1 to 20, preferably an integer of 2 to 6, more preferably an integer of 2 to 3.

In the formulae, —(C$_v$H$_{2v}$)— is optionally linear or branched, and may be, for example, —CH$_2$—, —CH$_2$CH$_2$—, —CH$_2$CH$_2$CH$_2$—, —CH(CH$_3$)— or —CH(CH$_3$)CH$_2$—.

The $R^{k1}$ group is optionally substituted with one or more substituents selected from a fluorine atom, a $C_{1-3}$ alkyl group and a $C_{1-3}$ fluoroalkyl group (preferably $C_{1-3}$ perfluoroalkyl group).

In one embodiment, the $R^{k1}$ group may be other than a —O—$C_{1-6}$ alkylene group.

In another embodiment, examples of the $R^{k1}$ group include the following groups:

[Formula 25]

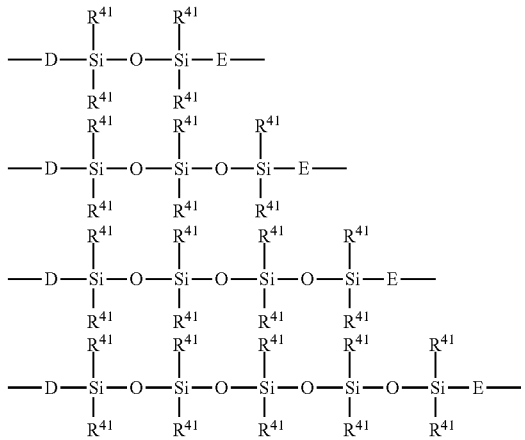

[Formula 26]

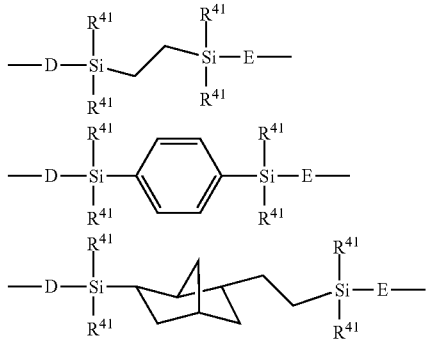

wherein each R$^{41}$ independently represents a hydrogen atom, a phenyl group, an alkyl group having 1 to 6 carbon atoms, or a $C_{1-6}$ alkoxy group, preferably a methyl group;

D is a group selected from
—CH$_2$O(CH$_2$)$_2$—,
—CH$_2$O(CH$_2$)$_3$—,
—CF$_2$O(CH$_2$)$_3$—, —(CH$_2$)$_2$—,
—(CH$_2$)$_3$—,
—(CH$_2$)$_4$—,
—CONH—(CH$_2$)$_3$—,
—CON(CH$_3$)—(CH$_2$)$_3$—,
—CON(Ph)-(CH$_2$)$_3$—, wherein Ph means phenyl, and

[Formula 27]

$$\underset{R^{42}}{\underset{|}{\overset{O}{\overset{\|}{-C}}-\underset{|}{N}}}-\phenyl-\underset{R^{42}}{\underset{|}{Si}}-CH_2CH_2-$$

wherein R$^{42}$ each independently represents a hydrogen atom, a C$_{1-6}$ alkyl group or a C$_{1-6}$ alkoxy group, preferably a methyl group or a methoxy group, more preferably a methyl group;

E is —(CH$_2$)$_{ne}$— (ne is an integer of 2 to 6),

D is bonded to PFPE$^1$ as a molecular backbone, and E is bonded to an opposite group to PFPE$^1$.

Specific examples of R$^{k1}$ include:
a single bond,
—CH$_2$OCH$_2$—,
—CH$_2$O(CH$_2$)
—CH$_2$O(CH$_2$)$_3$—,
CH$_2$O(CH$_2$)
—CF$_2$—CH$_2$—O—CH$_2$—,
—CF$_2$—CH$_2$—O—(CH$_2$)$_2$—,
—CF$_2$—CH$_2$—O—(CH$_2$)$_3$—,
—CF$_2$—CH$_2$—O—(CH$_2$)$_6$—,
—CH$_2$O(CH$_2$)$_3$Si(CH$_3$)$_2$OSi(CH$_3$)$_2$(CH$_2$)$_2$—,
—CH$_2$O(CH$_2$)$_3$Si(CH$_3$)$_2$OSi(CH$_3$)$_2$OSi(CH$_3$)$_2$(CH$_2$)$_2$—,
—CH$_2$O(CH$_2$)$_3$Si(CH$_3$)$_2$O(Si(CH$_3$)$_2$O)$_2$Si(CH$_3$)$_2$(CH$_2$)$_2$—,
—CH$_2$O(CH$_2$)$_3$Si(CH$_3$)$_2$O(Si(CH$_3$)$_2$O)$_3$Si(CH$_3$)$_2$(CH$_2$)$_2$—,
—CH$_2$O(CH$_2$)$_3$Si(CH$_3$)$_2$O(Si(CH$_3$)$_2$O)$_{10}$Si(CH$_3$)$_2$(CH$_2$)$_2$—,
—CH$_2$O(CH$_2$)$_3$Si(CH$_3$)$_2$O(Si(CH$_3$)$_2$O)$_{20}$Si(CH$_3$)$_2$(CH$_2$)$_2$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CF$_2$CF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
CH$_2$OCH$_2$CHFCF$_2$OCF$_2$—,
CH$_2$OCH$_2$CHFCF$_2$OCF$_2$CF$_2$—,
—CH$_2$OCH$_2$CHFCF$_2$OCF$_2$CF$_2$CF$_2$—,
CH$_2$OCH$_2$CHFCF$_2$OCF(CF$_3$)CF$_2$OCF$_2$—,
CH$_2$OCH$_2$CHFCF$_2$OCF(CF$_3$)CF$_2$OCF$_2$CF$_2$—,
CH$_2$OCH$_2$CHFCF$_2$OCF(CF$_3$)CF$_2$OCF$_2$CF$_2$CF$_2$—,
CH$_2$OCF$_2$CHFOCF$_2$CF$_2$CF$_2$—C(O)NH—CH$_2$—,
—CH$_2$OCH$_2$ (CH$_2$)$_7$CH$_2$Si(OCH$_3$)$_2$OSi(OCH$_3$)$_2$(CH$_2$)$_2$Si(OCH$_3$)$_2$OSi(OCH$_3$)$_2$(CH$_2$)$_2$—,
CH$_2$OCH$_2$CH$_2$CH$_2$Si(OCH$_3$)$_2$OSi(OCH$_3$)$_2$(CH$_2$)$_3$—,
—CH$_2$OCH$_2$CH$_2$CH$_2$Si(OCH$_2$CH$_3$)$_2$OSi(OCH$_2$CH$_3$)$_2$(CH$_2$)$_3$—,
—CH$_2$OCH$_2$CH$_2$CH$_2$Si(OCH$_3$)$_2$OSi(OCH$_3$)$_2$(CH$_2$)$_2$—,
—CH$_2$OCH$_2$CH$_2$CH$_2$Si(OCH$_2$CH$_3$)$_2$OSi(OCH$_2$CH$_3$)$_2$(CH$_2$)$_2$—,
—(CH$_2$)$_2$—Si(CH$_3$)$_2$—(CH$_2$)$_2$—,
—CH$_2$—,
—(CH$_2$)$_2$—,
—(CH$_2$)$_3$—,
—(CH$_2$)$_4$—,
—(CH$_2$)$_5$—,
—(CH$_2$)$_6$—,
—CF$_2$—,
—(CF$_2$)$_2$—,
—CF$_2$—CH$_2$—,
—CF$_2$—(CH$_2$)$_2$—,
—CF$_2$—(CH$_2$)$_3$—,
—CF$_2$—(CH$_2$)$_4$—,
—CF$_2$—(CH$_2$)$_5$—,
—CF$_2$—(CH$_2$)$_6$—,
—CO—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—S—(CH$_2$)$_3$—,
—(CH$_2$)$_2$S(CH$_2$)$_3$—,
—CONH—(CH$_2$)$_3$Si(CH$_3$)$_2$OSi(CH$_3$)$_2$(CH$_2$)$_2$—,
—CONH—(CH$_2$)$_3$Si(CH$_3$)$_2$OSi(CH$_3$)$_2$OSi(CH$_3$)$_2$(CH$_2$)$_2$—,
—CONH—(CH$_2$)$_3$Si(CH$_3$)$_2$O(Si(CH$_3$)$_2$O)$_2$Si(CH$_3$)$_2$(CH$_2$)$_2$—,
—CONH—(CH$_2$)$_3$Si(CH$_3$)$_2$O(Si(CH$_3$)$_2$O)$_3$Si(CH$_3$)$_2$(CH$_2$)$_2$—,
—CONH—(CH$_2$)$_3$Si(CH$_3$)$_2$O(Si(CH$_3$)$_2$O)$_{10}$Si(CH$_3$)$_2$(CH$_2$)$_2$—,
—CONH—(CH$_2$)$_3$Si(CH$_3$)$_2$O(Si(CH$_3$)$_2$O) 2$o$Si(CH$_3$)$_2$(CH$_2$)$_2$—,
—C(O) O—(CH$_2$)$_3$—,
—C(O)O—(CH$_2$)$_6$—,
—CH$_2$—O—(CH$_2$)$_3$—Si(CH$_3$)$_2$—(CH$_2$)$_2$—Si(CH$_3$)$_2$—(CH$_2$)$_2$—,
—CH$_2$—O—(CH$_2$)$_3$—Si(CH$_3$)$_2$—(CH$_2$)$_2$—Si(CH$_3$)$_2$—CH(CH$_3$)—,
—CH$_2$—O—(CH$_2$)$_3$—Si(CH$_3$)$_2$—(CH$_2$)$_2$—Si(CH$_3$)$_2$—(CH$_2$)$_3$—,
—CH$_2$—O—(CH$_2$)$_3$—Si(CH$_3$)$_2$—(CH$_2$)$_2$—Si(CH$_3$)$_2$—CH(CH$_3$)—CH$_2$—,
—OCH$_2$—,
—O(CH$_2$)$_3$—, and
—OCFHCF$_2$—

[Formula 28]

In particular, $R^{k1}$ is preferably
—CH$_2$OCH$_2$—,
—CH$_2$O(CH$_2$)$_2$—,
—CH$_2$O(CH$_2$)$_3$—,
—CH$_2$O(CH$_2$)$_6$—,
—CF$_2$—CH$_2$—O—CH$_2$—,
—CF$_2$—CH$_2$—O—(CH$_2$)$_2$—,
—CF$_2$—CH$_2$—O—(CH$_2$)$_3$—,
—CF$_2$—CH$_2$—O—(CH$_2$)$_6$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CF$_2$CF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
—CH$_2$OCH$_2$CHFCF$_2$OCF$_2$—,
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$)CF$_2$OCF$_2$—,
—CH$_2$OCH$_2$CHFCF$_2$OCF(CF$_3$)CF$_2$OCF$_2$CF$_2$—,
—CH$_2$OCH$_2$CHFCF$_2$OCF(CF$_3$)CF$_2$OCF$_2$CF$_2$CF$_2$—,
—CH$_2$OCF$_2$CHFOCF$_2$CF$_2$CF$_2$—C(O)NH—CH$_2$—,
—CH$_2$—,
—(CH$_2$)$_2$—,
—(CH$_2$)$_3$—,
—(CH$_2$)$_4$—,
—(CH$_2$)$_5$—,
—(CH$_2$)$_6$—,
—CF$_2$—,
—(CF$_2$)$_2$—,
—CF$_2$—CH$_2$—,
—CF$_2$—(CH$_2$)$_2$—,
—CF$_2$—(CH$_2$)$_3$—,
—CF$_2$—(CH$_2$)$_4$—,
—CF$_2$—(CH$_2$)$_5$—,
—CF$_2$—(CH$_2$)$_6$—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—OCH$_2$—,
—O(CH$_2$)$_3$—,
—OCFHCF$_2$—.

In the above list, examples of further preferable $R^{k1}$ preferably include
—CH$_2$OCH$_2$—,
—CH$_2$O(CH$_2$)$_2$—,
—CH$_2$O(CH$_2$)$_3$—,
—CH$_2$O(CH$_2$)$_6$—,
—CF$_2$—CH$_2$—O—CH$_2$—,
—CF$_2$—CH$_2$—O—(CH$_2$)$_2$—,
—CF$_2$—CH$_2$—O—(CH$_2$)$_3$—,
—CF$_2$—CH$_2$—O—(CH$_2$)$_6$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CF$_2$CF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
—CH$_2$OCH$_2$CHFCF$_2$OCF$_2$—,
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$)CF$_2$OCF$_2$—,
—CH$_2$OCH$_2$CHFCF$_2$OCF(CF$_3$)CF$_2$OCF$_2$CF$_2$—,
—CH$_2$OCH$_2$CHFCF$_2$OCF(CF$_3$)CF$_2$OCF$_2$CF$_2$CF$_2$—,
—CH$_2$OCF$_2$CHFOCF$_2$CF$_2$CF$_2$—C(O)NH—CH$_2$—,
—CONH—,
—CONH—CH$_2$—,
—CONH—(CH$_2$)$_2$—,
—CONH—(CH$_2$)$_3$—,
—CONH—(CH$_2$)$_6$—,
—CF$_2$CONH—,
—CF$_2$CONHCH$_2$—,
—CF$_2$CONH(CH$_2$)$_2$—,
—CF$_2$CONH(CH$_2$)$_3$—,
—CF$_2$CONH(CH$_2$)$_6$—,
—CON(CH$_3$)—(CH$_2$)$_3$—,
—CON(Ph)-(CH$_2$)$_3$—, wherein Ph means phenyl,
—CON(CH$_3$)—(CH$_2$)$_6$—,
—CON(Ph)-(CH$_2$)$_6$—, wherein Ph means phenyl,
—CF$_2$—CON(CH$_3$)—(CH$_2$)$_3$—,
—CF$_2$—CON(Ph)-(CH$_2$)$_3$—, wherein Ph means phenyl,
—CF$_2$—CON(CH$_3$)—(CH$_2$)$_6$—,
—CF$_2$—CON(Ph)-(CH$_2$)$_6$—, wherein Ph means phenyl,
—CONH—(CH$_2$)$_2$NH(CH$_2$)$_3$—,
—CONH—(CH$_2$)$_6$NH(CH$_2$)$_3$—.

In one embodiment, $R^{k1}$ represents $X^{e'}$. $X^{e'}$ is a single bond, an alkylene group having 1 to 6 carbon atoms, —R$^{51}$—C$_6$H$_4$—R$^{52}$—, —R$^{51}$—CONR$^4$—R$^{52}$—, —R$^{51}$—CONR$^4$—C$_6$H$_4$—R$^{52}$—, —R$^{51}$—CO—R$^{52}$—, —R$^{51}$—CO—C$_6$H$_4$—R$^{52}$—, —R$^{51}$—SO$_2$NR$^4$—R$^{52}$—, —R$^{51}$—SO$_2$NR$^4$—C$_6$H$_4$—R$^{52}$—, —R$^{51}$—SO$_2$—R$^{52}$—, or —R$^{51}$—SO$_2$—C$_6$H$_4$—R$^{52}$—. R$^{51}$ and R$^{52}$ each independently represent a single bond or an alkylene group having 1 to 6 carbon atoms, preferably a single bond or an alkylene group having 1 to 3 carbon atoms. $R^4$ is as defined above. The alkylene group is substituted or unsubstituted, preferably unsubstituted. Examples of the substituent of the alkylene group may include a halogen atom, preferably a fluorine atom. The alkylene group is linear or branched, preferably linear.

In a preferable embodiment, $X^{e'}$ may be
a single bond,
—$X^f$—,
an alkylene group having 1 to 6 carbon atoms, preferably 1 to 3 carbon atoms
a —$X^f$—$C_{1-6}$ alkylene group, preferably a —$X^f$—$C_{1-3}$ alkylene group, more preferably
a —$X^f$—$C_{1-2}$ alkylene group,
—$C_6H_4$—$R^{52'}$—,
—$CONR^{4'}$—$R^{52'}$—,
—$CONR^{4'}$—$C_6H_4$—$R^{52'}$—,
—$X^f$—$CONR^{4'}$—$R^{52'}$—,
—$X^f$—$CONR^{4'}$—$C_6H_4$—$R^{52'}$—,
—CO—$R^{52'}$—,
—CO—$C_6H_4$—$R^{52'}$—,
—$SO_2NR^{4'}$—$R^{52'}$—,
—$SO_2NR^{4'}$—$C_6H_4$—$R^{52'}$—,
—$SO_2$—$R^{52'}$—,
—$SO_2$—$C_6H_4$—$R^{52'}$—,
—$R^{51'}$—$C_6H_4$—,
—$R^{51'}$—$CONR^{4'}$—,
—$R^{51'}$—$CONR^{4'}$—$C_6H_4$—,
—$R^{51'}$—CO—,
—$R^{51'}$—CO—$C_6H_4$—,
—$R^{51'}$—$SO_2NR^{4'}$—,
—$R^{51'}$—$SO_2NR^{4'}$—$C_6H_4$—,
—$R^{31'}$—$SO_2$—,
—$R^{51'}$—$SO_2$—$C_6H_4$—,
—$C_6H_4$—
—$CONR^{4'}$—,
—$CONR^{4'}$—$C_6H_4$—,
—$X^f$—$CONR^{4'}$—,
—$X^f$—$CONR^{4'}$—$C_6H_4$—,
—CO—,
—CO—$C_6H_4$—,
—$SO_2NR^{4'}$—,
—$SO_2NR^{4'}$—$C_6H_4$—,
—$SO_2$—, or
—$SO_2$—$C_6H_4$—
wherein $R^{51'}$ and $R^{52'}$ are each independently a linear alkylene group having 1 to 6 carbon atoms, preferably 1 to 3 carbon atoms, the alkylene group is substituted or unsubstituted, as described above, and examples of the substituent of the alkylene group may include a halogen atom, preferably a fluorine atom, and
$R^{4'}$ is a hydrogen atom or a methyl group.

In particular, $X^{e'}$ may be preferably
—$X^f$—,
an alkylene group having 1 to 6 carbon atoms, preferably 1 to 3 carbon atoms, or
a —$X^f$—$C_{1-6}$ alkylene group, preferably a —$X^f$—$C_{1-3}$ alkylene group, more preferably
a —$X^f$—$C_{1-2}$ alkylene group,
—$CONR^{4'}$—$R^{52'}$—,
—$CONR^{4'}$—$C_6H_4$—$R^{52'}$—,
—$X^f$—$CONR^{4'}$—$R^{52'}$—,
—$X^f$—$CONR^{4'}$—$C_6H_4$—$R^{52'}$—,
—$R^{51'}$—$CONR^{4'}$—,
—$R^{51'}$—$CONR^{4'}$—$C_6H_4$—,
—$CONR^{4'}$—,
—$CONR^{4'}$—$C_6H_4$—,
—$X^f$—$CONR^{4'}$—,
—$X^f$—$CONR^{4'}$—$C_6H_4$—,
—$R^{51'}$—$CONR^{4'}$—, or
—$R^{51'}$—$CONR^{4'}$—$C_6H_4$—. In the formulae, $X^f$, $R^{4'}$, $R^{51'}$ and $R^{52'}$ each are as defined above.

In particular, $X^{e'}$ may be more preferably
—$CONR^{4'}$—$R^{52'}$—,
—$CONR^{4'}$—$C_6H_4$—$R^{52'}$—,
—$X^f$—$CONR^{4'}$—$R^{52'}$—,
—$X^f$—$CONR^{4'}$—$C_6H_4$—$R^{52'}$—,
—$R^{51'}$—$CONR^{4'}$—,
—$R^{51'}$—$CONR^{4'}$—$C_6H_4$—,
—$CONR^{4'}$—,
—$CONR^{4'}$—$C_6H_4$—,
—$X^f$—$CONR^{4'}$—, or
—$X^f$—$CONR^{4'}$—$C_6H_4$—.

Specific examples of $X^{e'}$ in the present embodiment include
a single bond,
a perfluoroalkylene group having 1 to 6 carbon atoms (for example, —$CF_2$— and —$(CF_2)_2$—),
an alkylene group having 1 to 6 carbon atoms,
a —$CF_2$—$C_{1-6}$ alkylene group,
—CONH—,
—CONH—$CH_2$—,
—CONH—$(CH_2)_2$—,
—CONH—$(CH_2)_3$—,
—$CF_2$—CONH—,
—$CF_2CONHCH_2$—,
—$CF_2CONH(CH_2)_2$—,
—$CF_2CONH(CH_2)_3$—,
—$CON(CH_3)$—,
—$CON(CH_3)$—$CH_2$—,
—$CON(CH_3)$—$(CH_2)_2$—,
—$CON(CH_3)$—$(CH_2)_3$—,
—$CF_2$—$CON(CH_3)$—,
—$CF_2$—$CON(CH_3)CH_2$—,
—$CF_2$—$CON(CH_3)$—$(CH_2)_2$—,
—$CF_2$—$CON(CH_3)$—$(CH_2)_3$—,
—$CH_2$—CONH—,
—$CH_2$—CONH—$CH_2$—,
—$CH_2$—CONH—$(CH_2)_2$—,
—$CH_2$—CONH—$(CH_2)_3$—,
—$CF_2$—$CH_2$—CONH—,
—$CF_2$—$CH_2$—CONH—$CH_2$—,
—$CF_2$—$CH_2$—CONH—$(CH_2)_2$—,
—$CF_2$—$CH_2$—CONH—$(CH_2)_3$—,
—CONH—$C_6H_4$—,
—$CON(CH_3)$—$C_6H_4$—,
—$CH_2$—$CON(CH_3)$—$CH_2$—,
—$CH_2$—$CON(CH_3)$—$(CH_2)_2$—,
—$CH_2$—$CON(CH_3)$—$(CH_2)_3$—,
—$CON(CH_3)$—$C_6H_4$—,
—$CF_2$—CONH—$C_6H_4$—,
—$CF_2$—$CON(CH_3)$—$C_6H_4$—,
—$CF_2$—$CH_2$—$CON(CH_3)$—$CH_2$—,
—$CF_2$—$CH_2$—$CON(CH_3)$—$(CH_2)_2$—,
—$CF_2$—$CH_2$—$CON(CH_3)$—$(CH_2)_3$—,
—$CF_2$—$CON(CH_3)$—$C_6H_4$—,
—CO—,
—CO—$C_6H_4$—,
—$C_6H_4$—,
—$SO_2NH$—,
—$SO_2NH$—$CH_2$—,
—$SO_2NH$—$(CH_2)_2$—,
—$SO_2NH$—$(CH_2)_3$—, —SO$_2$NH—C$_6$H$_4$—,
—SO$_2$N(CH$_3$)—,
—SO$_2$N(CH$_3$)—CH$_2$—,
—SO$_2$N(CH$_3$)—(CH$_2$)$_2$—,
—SO$_2$N(CH$_3$)—(CH$_2$)$_3$—,
—SO$_2$N(CH$_3$)—C$_6$H$_4$—,
—SO$_2$—,
—SO$_2$—CH$_2$—,
—SO$_2$—(CH$_2$)$_2$—,
—SO$_2$—(CH$_2$)$_3$—, or
—SO$_2$—C$_6$H$_4$—.

In the above list, examples of preferable $X^{e'}$ include a perfluoroalkylene group having 1 to 6 carbon atoms (for example, —CF$_2$— and —(CF$_2$)$_2$—,
an alkylene group having 1 to 6 carbon atoms,
a —CF$_2$—C$_{1-6}$ alkylene group,
—CONH—,
—CONH—CH$_2$—,
—CONH—(CH$_2$)$_2$—,
—CONH—(CH$_2$)$_3$—,
—CF$_2$CONH—,
—CF$_2$CONHCH$_2$—,
—CF$_2$CONH(CH$_2$)$_2$—,
—CF$_2$CONH(CH$_2$)$_3$—,
—CON(CH$_3$)—,
—CON(CH$_3$)—CH$_2$—,
—CON(CH$_3$)—(CH$_2$)$_2$—,
—CON(CH$_3$)—(CH$_2$)$_3$—,
—CF$_2$—CON(CH$_3$)—,
—CF$_2$—CON(CH$_3$)CH$_2$—,
—CF$_2$—CON(CH$_3$)—(CH$_2$)$_2$—,
—CF$_2$—CON(CH$_3$)—(CH$_2$)$_3$—,
—CH$_2$—CONH—,
—CH$_2$—CONH—CH$_2$—,
—CH$_2$—CONH—(CH$_2$)$_2$—,
—CH$_2$—CONH—(CH$_2$)$_3$—,
—CF$_2$—CH$_2$—CONH—,
—CF$_2$—CH$_2$—CONH—CH$_2$—,
—CF$_2$—CH$_2$—CONH—(CH$_2$)$_2$—,
—CF$_2$—CH$_2$—CONH—(CH$_2$)$_3$—,
—CONH—C$_6$H$_4$—,
—CON(CH$_3$)—C$_6$H$_4$—,
—CH$_2$—CON(CH$_3$)—CH$_2$—,
—CH$_2$—CON(CH$_3$)—(CH$_2$)$_2$—,
—CH$_2$—CON(CH$_3$)—(CH$_2$)$_3$—,
—CON(CH$_3$)—C$_6$H$_4$—,
—CF$_2$—CONH—C$_6$H$_4$—,
—CF$_2$—CON(CH$_3$)—C$_6$H$_4$—,
—CF$_2$—CH$_2$—CON(CH$_3$)—CH$_2$—,
—CF$_2$—CH$_2$—CON(CH$_3$)—(CH$_2$)$_2$—,
—CF$_2$—CH$_2$—CON(CH$_3$)—(CH$_2$)$_3$—, and
—CF$_2$—CON(CH$_3$)—C$_6$H$_4$—.

In the above list, examples of more preferable $X^{e'}$ include
—CONH—,
—CONH—CH$_2$—,
—CONH—(CH$_2$)$_2$—,
—CONH—(CH$_2$)$_3$—,
—CF$_2$CONH—,
—CF$_2$CONHCH$_2$—,
—CF$_2$CONH(CH$_2$)$_2$—,
—CF$_2$CONH(CH$_2$)$_3$—,
—CON(CH$_3$)—,
—CON(CH$_3$)—CH$_2$—,
—CON(CH$_3$)—(CH$_2$)$_2$—,
—CON(CH$_3$)—(CH$_2$)$_3$—,
—CF$_2$—CON(CH$_3$)—,
—CF$_2$—CON(CH$_3$)CH$_2$—,
—CF$_2$—CON(CH$_3$)—(CH$_2$)$_2$—,
—CF$_2$—CON(CH$_3$)—(CH$_2$)$_3$—,
—CH$_2$—CONH—,
—CH$_2$—CONH—CH$_2$—,
—CH$_2$—CONH—(CH$_2$)$_2$—,
—CH$_2$—CONH—(CH$_2$)$_3$—,
—CF$_2$—CH$_2$—CONH—,
—CF$_2$—CH$_2$—CONH—CH$_2$—,
—CF$_2$—CH$_2$—CONH—(CH$_2$)$_2$—,
—CF$_2$—CH$_2$—CONH—(CH$_2$)$_3$—,
—CONH—C$_6$H$_4$—,
—CON(CH$_3$)—C$_6$H$_4$—,
—CH$_2$—CON(CH$_3$)—CH$_2$—,
—CH$_2$—CON(CH$_3$)—(CH$_2$)$_2$—,
—CH$_2$—CON(CH$_3$)—(CH$_2$)$_3$—,
—CON(CH$_3$)—C$_6$H$_4$—
—CF$_2$—CONH—C$_6$H$_4$—,
—CF$_2$—CON(CH$_3$)—C$_6$H$_4$—,
—CF$_2$—CH$_2$—CON(CH$_3$)—CH$_2$—,
—CF$_2$—CH$_2$—CON(CH$_3$)—(CH$_2$)$_2$—,
—CF$_2$—CH$_2$—CON(CH$_3$)—(CH$_2$)$_3$—, or
—CF$_2$—CON(CH$_3$)—C$_6$H$_4$—.

In one embodiment, $X^{e'}$ is a single bond. In the present embodiment, PFPE$^1$ and a group having a binding ability to the base material are directly bonded.

In still another embodiment, $R^{k1}$ is a group represented by formula: —(R$^{16}$)$_x$—(CFR$^{17}$)$_y$—(CH$_2$)$_z$—. In the formula, x, y and z are each independently an integer of 0 to 10, the sum of x, y and z is 1 or more, and the occurrence order of the respective repeating units in parentheses is not limited in the formula.

In the formula, R$^{16}$, at each occurrence, each independently represents an oxygen atom, phenylene, carbazolylene, —NR$^{18}$—, wherein R$^{18}$ represents a hydrogen atom or an organic group, or a divalent organic group. Preferably, R$^{16}$ is an oxygen atom or a divalent polar group.

The "divalent polar group" is not limited, and examples thereof include —C(O)—, —C(=NR$^{19}$)—, and —C(O)NR$^{19}$—, wherein R$^{13}$ represents a hydrogen atom or a lower alkyl group. The "lower alkyl group" is, for example, an alkyl group having 1 to 6 carbon atoms, such as a methyl group, an ethyl group, or a n-propyl group, and such a group is optionally substituted with one or more fluorine atoms.

In the formula, R$^{17}$, at each occurrence, is each independently a hydrogen atom, a fluorine atom or a lower fluoroalkyl group, preferably a fluorine atom. The "lower fluoroalkyl group" is, for example, a fluoroalkyl group having 1 to 6 carbon atoms, preferably 1 to 3 carbon atoms, preferably a perfluoroalkyl group having 1 to 3 carbon atoms, more preferably a trifluoromethyl group or a pentafluoroethyl group, further preferably a trifluoromethyl group.

In this embodiment, $R^{k1}$ is preferably a group represented by formula: —(O)$_x$—(CF$_2$)$_y$—(CH$_2$)$_z$—, wherein x, y and z are as defined above, and the occurrence order of the respective repeating units in parentheses is not limited in the formula.

Examples of the group represented by formula: —(O)$_x$—(CF$_2$)$_y$—(CH$_2$)$_z$— include any group represented by —(O)$_x$—(CH$_2$)$_{z''}$—O—[(CH$_2$)$_{z'''}$—O—]$_{z''''}$, and —(O)$_{x'}$—(CF$_2$)$_{y''}$—(CH$_2$)$_{z''}$—O—[(CH$_2$)$_{z'''}$—O—]$_{z''''}$, wherein x' is 0 or 1, y'', z'' and z''' are each independently an integer of 1 to 10, and z'''' is 0 or 1. Herein, a left end of such a group is bonded to PFPE.

In another preferable embodiment, $R^{k1}$ is —O—CFR$^{20}$—(CF$_2$)$_{e'''}$—.

R$^{20}$ each independently represents a fluorine atom or a lower fluoroalkyl group. The lower fluoroalkyl group is, for example, a fluoroalkyl group having 1 to 3 carbon atoms, preferably a perfluoroalkyl group having 1 to 3 carbon atoms, more preferably a trifluoromethyl group or a pentafluoroethyl group, further preferably a trifluoromethyl group.

e''' is each independently 0 or 1.

In one specific example, $R^{20}$ is a fluorine atom and e''' is 1.

In still another embodiment, examples of the $R^{k1}$ group include the following groups:

[Formula 29]

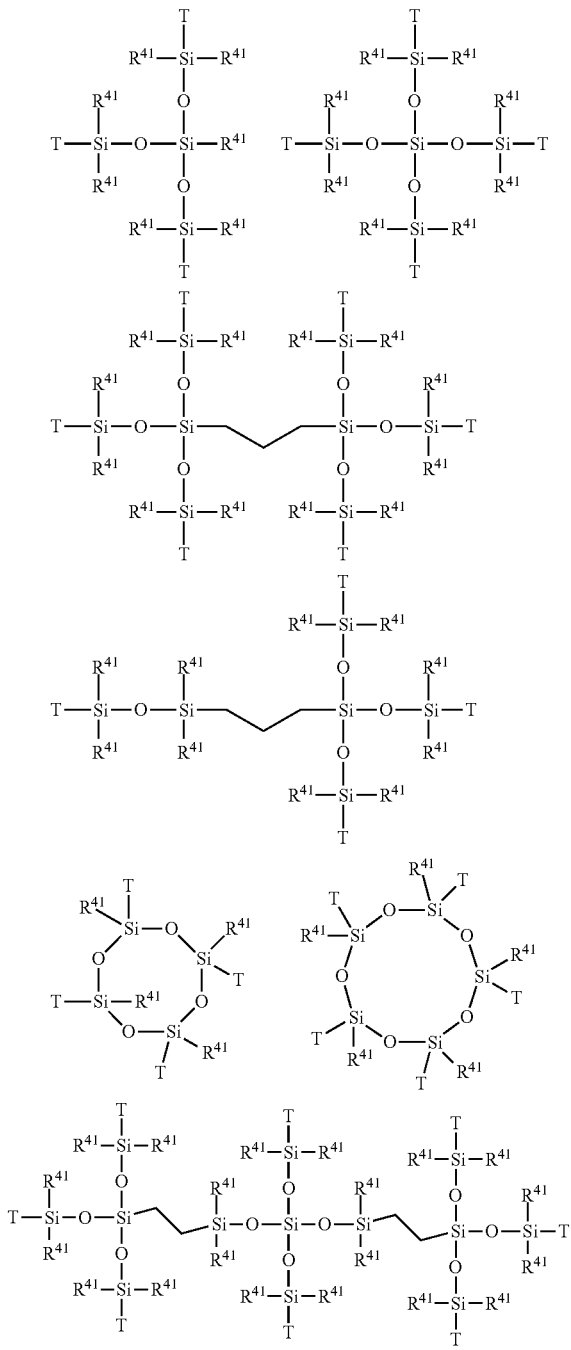

-continued

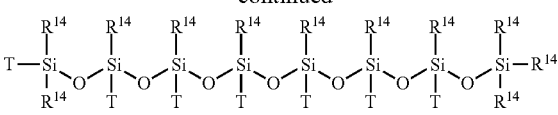

wherein $R^{41}$ each independently represents a hydrogen atom, a phenyl group, an alkyl group having 1 to 6 carbon atoms, or a $C_{1-6}$ alkoxy group, preferably a methyl group;

any number of the T in each $R^{k1}$ group is the following group bonded to PFPE as a molecular backbone:

—$CH_2O(CH_2)_2$—,

—$CH_2O(CH_2)_3$—,

—$CF_2O(CH_2)_3$—,

—$CH_2$—,

—$(CH_2)_2$—,

—$(CH_2)_3$—,

—$(CH_2)_4$—,

—CONH—$(CH_2)_3$—,

—$CON(CH_3)$—$(CH_2)_3$—,

—CON(Ph)-$(CH_2)_3$—, wherein Ph means phenyl, or

[Formula 30]

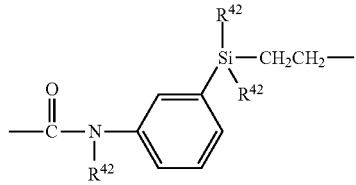

wherein each $R^{42}$ independently represents a hydrogen atom, a $C_{1-6}$ alkyl group or a $C_{1-6}$ alkoxy group, preferably a methyl group or a methoxy group, more preferably a methyl group, another of the T is —$(CH_2)_{n''}$— (n'' is an integer of 2 to 6) bonded to an opposite group to PFPE as a molecular backbone, and the remaining of the T, if present, may be independently a methyl group, a phenyl group, a $C_{1-6}$ alkoxy group, or a radical scavenging group or an UV absorbing group.

The radical scavenging group is not limited as long as it can scavenge a radial generated by light irradiation, and examples thereof include a residue of benzophenones, benzotriazoles, benzoates, phenyl salicylates, crotonic acids, malonates, organoacrylates, hindered amines, hindered phenols, or triazines.

The UV absorbing group is not limited as long as it can absorb ultraviolet light, and examples thereof include a residue of benzotriazoles, hydroxybenzophenones, esters of substituted and unsubstituted benzoic acid or salicylic acid compounds, acrylates or alkoxy cinnamates, oxamides, oxanilides, benzoxazinones, and benzoxazoles.

In a preferable embodiment, examples of a preferable radical scavenging group or an UV absorbing group include

[Formula 31]

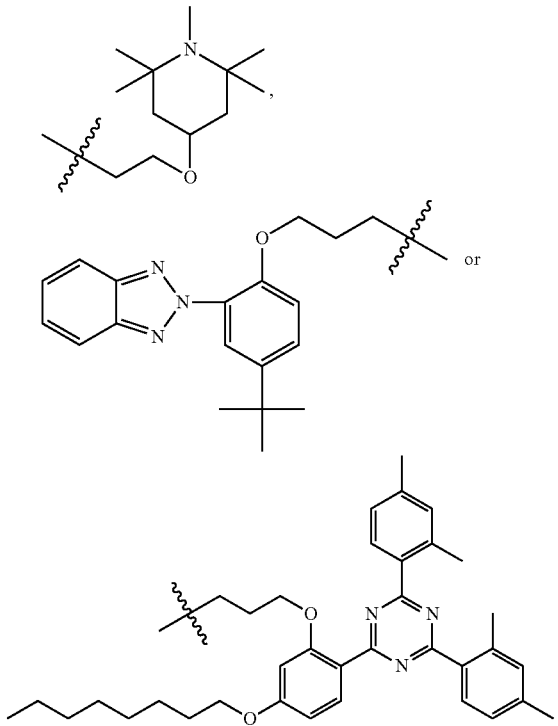

In one embodiment, examples of $R^{k1}$ may include any group represented by $-R^{k2}-CH_2-$, $-R^{k2}-OCH_2-$, $-R^{k2}-CH_2OCH_2-$, or $-R^{k2}-CO-NR^1-Y^{j2}-$. A left portion of the formula of the divalent organic group (namely, $R^{k2}$ portion) is bonded to PFPE.

In the embodiment, $R^{k2}$ is a single bond or a divalent hydrocarbon group having 1 to 15 carbon atoms, and may contain an ether bond. Examples of the hydrocarbon group in $R^{k2}$ may include an alkylene group or an alkylene group optionally containing ether oxygen. The alkylene group is optionally substituted or unsubstituted, as described above.

In one embodiment, $R^{k2}$ is preferably a single bond. In another embodiment, examples of $R^{k2}$ may include a divalent hydrocarbon group, preferably an alkylene group where any hydrogen atom is at least partially substituted with a fluorine atom, such as $-CFH-$, $-CF_2-$, $-(CF_2)_2-$ or $-(CF_2)_3-$, specifically $-CF_2-$.

In the embodiment, $Y^{j2}$ is $-CH_2-$, or an o, m or p-dimethylsilylphenylene group represented by the following formula. In the following formula, a phenylene group and a
Si atom are bonded to a N atom, and a $-CH=CH_2$ group in formula (I), respectively.

[Formula 32]

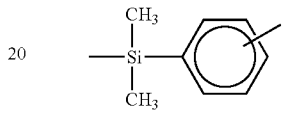

In the embodiment, $R^1$ is a hydrogen atom or a substituted or unsubstituted monovalent hydrocarbon group. The substituted or unsubstituted monovalent hydrocarbon group is preferably a monovalent hydrocarbon group having 1 to 12 carbon atoms, more preferably a monovalent hydrocarbon group having 1 to 10 carbon atoms. Specific examples of such a substituted or unsubstituted monovalent hydrocarbon group include alkyl groups such as a methyl group, an ethyl group, a propyl group, a butyl group, a hexyl group, a cyclohexyl group and an octyl group; aryl groups such as a phenyl group and a tolyl group; aralkyl groups such as a benzyl group and a phenylethyl group, or a monovalent hydrocarbon group where some or all hydrogen atoms are substituted with a halogen atom such as a fluorine atom. $R^1$ is preferably a hydrogen atom, a methyl group or a phenyl group.

In the embodiment, examples of the structure of a specific PFPE-containing unsaturated compound may include the following structures. In the following structures, PFPE and $R^{k2}$ are as defined above.

[Formula 33]

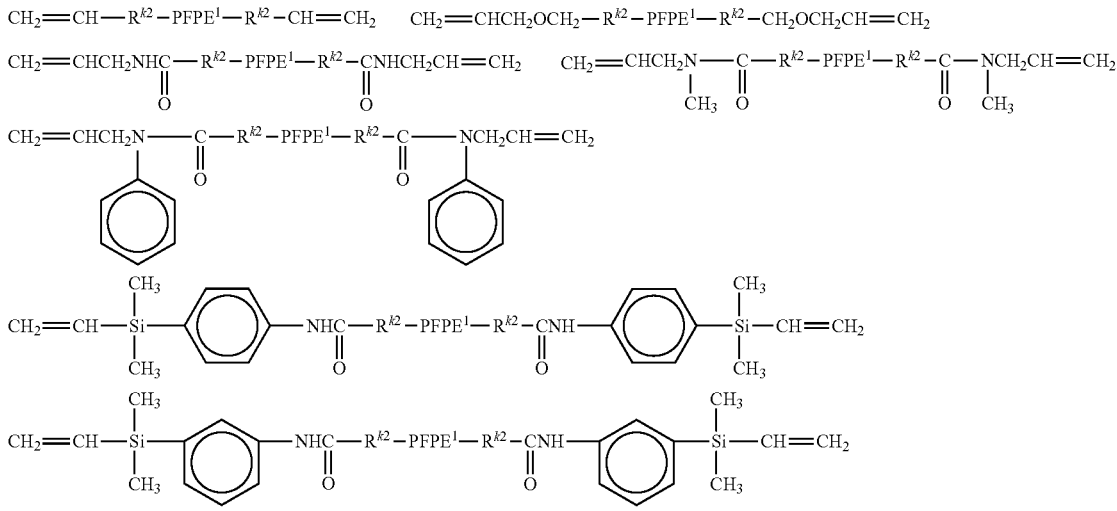

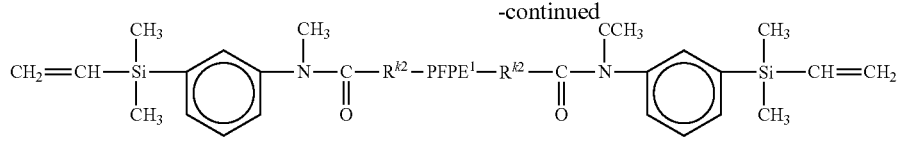

In one embodiment, the PFPE-containing compound is a PFPE-containing silane compound.

In one embodiment, the PFPE-containing compound is a PFPE-containing unsaturated compound.

The curable composition used in the present invention may further include a cross-linking agent.

The cross-linking agent is not limited as long as the agent is a compound having a portion which can undergo a crosslinking reaction (condensation reaction) or an addition reaction with the PFPE-containing compound (for example, PFPE-containing silane compound, specifically, a silane portion having a hydroxyl group or a hydrolyzable group bonded to a Si atom of the PFPE-containing silane compound, or a carbon-carbon double bond portion of the PFPE-containing unsaturated compound). The PFPE-containing compound and the cross-linking agent can be included, thereby improving physical properties (for example, tensile strength and elastic modulus) of a cured product obtained from the curable composition of the present invention.

The cross-linking agent is preferably at least one selected from the group consisting of an organosilicon compound having at least two —O—$R^{g3}$ each bonded to a Si atom and an organosilicon compound having two or more hydrogen atoms each bonded to a silicon atom (Si—H) in one molecule. $R^{g3}$ is described below.

In one embodiment, the cross-linking agent is an organosilicon compound having at least two —O—$R^{g3}$ each bonded to a Si atom (hereinafter, also referred to as "cross-linking agent (1)"). In the formula, $R^{g3}$, at each occurrence, each independently represents a hydrogen atom or a monovalent organic group. The monovalent organic group means a carbon atom-containing group. Such a monovalent organic group is not limited, and examples thereof include a group where one hydrogen atom is further removed from a hydrocarbon group. The hydrocarbon group is as defined above.

The cross-linking agent has a structure different from the structure of the PFPE-containing silane compound.

Examples of the cross-linking agent (1) may include an organic compound where $R^{g3}$ is a hydrogen atom, namely, an organosilicon compound having at least two silanol groups in one molecule, and any organosilicon compound represented by formulae (E3) to (E5) described below.

Organosilicon compound having at least two silanol groups in one molecule:

Such silanol groups are preferably present at both respective ends of a molecular backbone in the organosilicon compound. The molecular backbone here represents a relatively longest binding chain in a molecule of the organosilicon compound.

Examples of the compound having silanol groups at both respective ends of a molecular backbone may include a compound represented by the following formula (E1) or (E2).

[Formula 34]

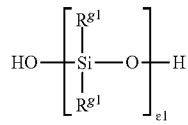 (E1)

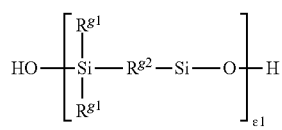 (E2)

In formula (E1) or (E2), $R^{g1}$, at each occurrence, is each independently a substituted or unsubstituted monovalent hydrocarbon group having 1 to 8 carbon atoms. Specific examples of $R^{g1}$ include alkyl groups such as a methyl group, an ethyl group, a propyl group, an isopropyl group, a butyl group, an isobutyl group, a tert-butyl group, a pentyl group, a neopentyl group, a hexyl group, a heptyl group, an octyl group, a nonyl group and a decyl group; cycloalkyl groups such as a cyclopentyl group, a cyclohexyl group and a cycloheptyl group; alkenyl groups such as a vinyl group, an allyl group, a propenyl group, an isopropenyl group, a butenyl group, an isobutenyl group, a hexenyl group and a cyclohexenyl group; aryl groups such as a phenyl group, a tolyl group, a xylyl group and a naphthyl group; aralkyl groups such as a benzyl group, a phenylethyl group and a phenylpropyl group; and groups where some or all hydrogen atoms of such a group are substituted with a halogen atom (for example, a chloromethyl group, a bromoethyl group, a chloropropyl group, a trifluoropropyl group and a nonafluorohexyl group).

In formula (E1) or (E2), $R^{g2}$, at each occurrence, is each independently a substituted or unsubstituted divalent hydrocarbon group having 1 to 20 carbon atoms, preferably 2 to 10 carbon atoms. Specific examples of $R^{g2}$ include alkylene groups such as a methylene group, an ethylene group, a propylene group, a methylethylene group, a butylene group and a hexamethylene group; cycloalkylene groups such as a cyclohexylene group, arylene groups such as a phenylene group, a tolylene group, a xylylene group, a naphthylene group and a biphenylene group; a group where some or all hydrogen atoms of such a group are substituted with a halogen atom; and a combination of such a substituted or unsubstituted alkylene group and an arylene group. Among them, $R^{g2}$ is preferably a methylene group, an ethylene group, a propylene group, a butylene group, a hexamethylene group, a cyclohexylene group or a phenylene group, and is particularly preferably an ethylene group, a propylene group, a butylene group or a phenylene group. Examples of the compound having silanol groups in a molecule include a resin compound including a bond of one unit of $R^{g1}_3SiO_{1/2}$, $R^{g1}_2SiO$, $R^{g1}SiO_{3/2}$, and $SiO_2$, or a combination of two or more kinds thereof, with a silanol group. Constituent units of the resin compound may be directly bonded or may be bonded via a di- or higher valent hydrocarbon group.

In formula (E1) or (E2), ε1, at each occurrence, is each independently an integer of 1 or more, and ε1 is preferably 2 or more, more preferably 5 or more, preferably 50 or less, more preferably 20 or less.

The organosilicon compound having at least two silanol groups in one molecule (specifically, compound represented by formula (E1) or (E2)) preferably has no PFPE structure in a molecular structure.

Any organosilicon compound represented by formula (E3), (E4) or (E5):

[Formula 35]

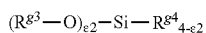  (E3)

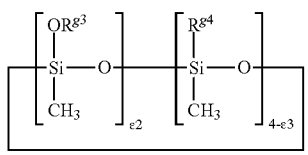  (E4)

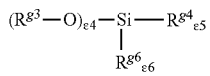  (E5)

In formulae (E3) and (E4), $R^{g3}$ is as defined above. $R^{g3}$ is a portion which can react with a portion having a hydroxyl group or a hydrolyzable group bonded to a Si atom of the PFPE-containing silane compound represented by formula (A), (B), (C) or (D).

$R^{g3}$ is preferably a monovalent organic group.

$R^{g3}$—, at each occurrence, is more preferably each independently $CH_3$—, $C_2H_5$—, $C_3H_7$—, $CF_3CH_2$—, $CH_3CO$—, $CH_2$=$C(CH_3)$—, $CH_3CH_2C(CH_3)$=$N$—, $(CH_3)_2N$—, $(C_2H_5)_2N$—, $CH_2$=$C(OC_2H_5)$—, $(CH_3)_2C$=$C(OC_8H_{17})$—, or

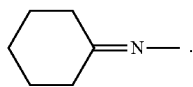

In formulae (E3) and (E4), $R^{g4}$, at each occurrence, is each independently a monovalent organic group. $R^{g4}$ is preferably a substituted or unsubstituted monovalent hydrocarbon group, more preferably a substituted or unsubstituted monovalent hydrocarbon group having 1 to 12 carbon atoms. Specific examples of $R^{g4}$ may include alkyl groups such as a methyl group, an ethyl group, a propyl group, an isopropyl group, a butyl group, an isobutyl group, a tert-butyl group, a pentyl group, a neopentyl group, a hexyl group, a heptyl group, an octyl group, a nonyl group and a decyl group; cycloalkyl groups such as a cyclopentyl group, a cyclohexyl group and a cycloheptyl group; aryl groups such as a phenyl group, a tolyl group, a xylyl group and a naphthyl group; aralkyl groups such as a benzyl group, a phenylethyl group and a phenylpropyl group; alkenyl groups such as a vinyl group, an allyl group, a propenyl group and a butenyl group; and groups where some or all hydrogen atoms of such a group are substituted with a halogen atom such as fluorine, chlorine or bromine (for example, a chloromethyl group, a bromoethyl group, a chloropropyl group, a trifluoropropyl group and a 3,3,4,4,5,5,6,6,6-nonafluorohexyl group).

In one embodiment, $R^{g4}$ can be a group represented by the following general formula.

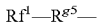

In the formulae, $Rf^1$ is a monovalent fluorinated polyether group. Examples of $Rf^1$ include one having a structure where $CF_3O$—, $CF_3CF_2O$—, $CF_3CF_2CF_2O$—, $(CF_3)_2CFO$—, $CF_3CF_2CF_2CF_2O$— or the like is bonded to a $CF_2$ end of PFPE above.

$R^{g5}$ is a divalent organic group. The divalent organic group is as defined above.

$R^{g5}$ can be a substituted or unsubstituted divalent hydrocarbon group optionally containing one or more of, for example, an oxygen atom, a nitrogen atom, a silicon atom and a sulfur atom, and an amide bond or a sulfonamide bond. The divalent hydrocarbon group preferably has 2 to 20 carbon atoms. Specific examples of a substituted or unsubstituted divalent hydrocarbon group not having any oxygen atom, nitrogen atom, silicon atom or sulfur atom interposed and not containing any amide bond or sulfonamide bond include alkylene groups such as an ethylene group, a propylene group, a methylethylene group, a butylene group and a hexamethylene group; cycloalkylene groups such as a cyclohexylene group; arylene groups such as a phenylene group, a tolylene group, a xylylene group, a naphthylene group and a biphenylene group; a combination of any alkylene group and any arylene group; and a group where some or all hydrogen atoms of such alkylene group and arylene group are substituted with a halogen atom.

The divalent hydrocarbon group may contain an oxygen atom in the form of —O—, a nitrogen atom in the form of —$NR^{g51}$— ($R^{g51}$ is a hydrogen atom or an alkyl group or aryl group having 1 to 10 carbon atoms) or —N=, a silicon atom in the form of —$SiR^{g52}R^{g53}$— ($R^{g52}$ and $R^{g53}$, at each occurrence, are each independently an alkyl group or aryl group having 1 to 10 carbon atoms), and/or a sulfur atom in the form of —S—. The divalent hydrocarbon group may contain an amide bond in the form of —C(=O)$NR^{g51}$— ($R^{g51}$ is the same as described above) and/or a sulfonamide bond in the form of —$SO_2NR^{g51}$— ($R^{g51}$ is the same as described above). Specific examples of such a divalent hydrocarbon group include the following. In the following formulae, Me represents a methyl group and Ph represents a phenyl group, and an $Rf^1$ group is bonded to a left portion of each of the following formulae.

[Formula 36]

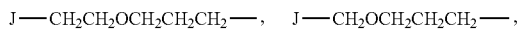
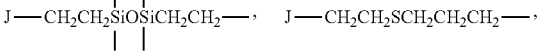
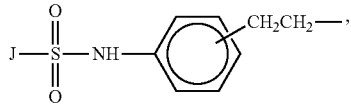

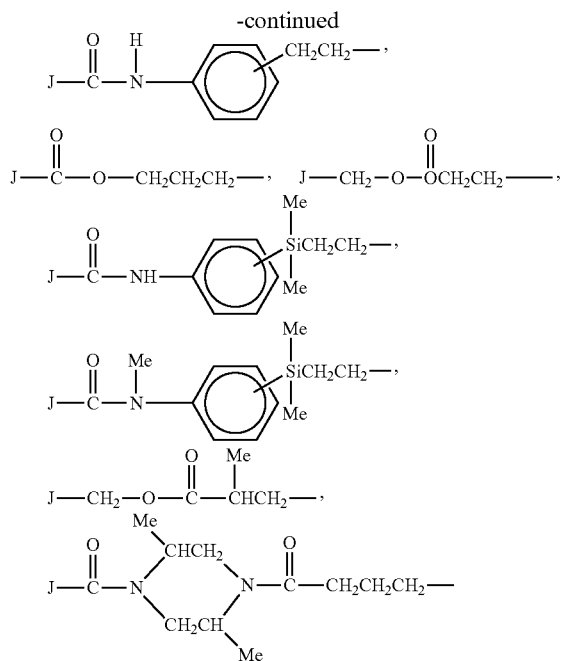

wherein J represents a bonding site.

In formulae (E3) and (E4), each ε2, at each occurrence, is independently 2 or 3, and each ε3, at each occurrence, is independently 2 or 3.

In formula (E5), $R^{g3}$ and $R^{g4}$ are as defined above. In formula (E5), each $R^{g6}$—, at each occurrence, independently represents $R^{g8}$—$R^{g7}$—.

Each $R^{g7}$, at each occurrence, independently represents a single bond an oxygen atom or a divalent organic group. The divalent organic group is as described above.

$R^{g7}$ is preferably an alkylene group having 1 to 10 carbon atoms or a group having 1 to 10 carbon atoms and containing a nitrogen atom or an oxygen atom in a main chain.

$R^{g7}$ is more preferably
an alkylene group having 1 to 3 carbon atoms,
$CH_2CH_2$—NH—$CH_2CH_2CH_2$, or
$CH_2$—O—$CH_2CH_2CH_2$.

$R^{g8}$ is a reactive functional group. $R^{g8}$, at each occurrence, is preferably each independently an amino group, an epoxy group, a methacrylic group, a vinyl group or a mercapto group, more preferably an amino group.

In formula (E5), ε4 is an integer of 2 or more, preferably 2 or 3, more preferably 3. In formula (E5), ε5 is an integer of 0 or more, preferably 0 or 1. In formula (E5), ε6 is 1 or 2, preferably 1, provided that the sum of ε4, ε5 and ε6 is 4.

In formula (E5), preferably ε4 is 2 or 3, ε5 is 0 or 1 and ε6 is 1 or 2, more preferably ε4 is 3, ε5 is 0 and ε6 is 1.

Preferably, the cross-linking agent (1) is any compound represented by formula (E3) or formula (E5), more preferably any compound represented by formula (E3).

In one embodiment, the cross-linking agent does not have any group represented by PFPE in a molecular chain.

In one embodiment, the molecular weight of the cross-linking agent is 1,000 or less, preferably 600 or less, more preferably 250 or less. The lower limit of the molecular weight of the cross-linking agent may be 50 or more or 100 or more.

In a preferable embodiment, the cross-linking agent (1) is at least one selected from the group consisting of tetraethoxysilane, tetratrimethoxysilane, methyltriethoxysilane, methyltrimethoxysilane, dimethyldimethoxysilane, dimethyltrimethoxysilane, aminopropyltriethoxysilane, aminopropyltrimethoxysilane, tridecafluoro-n-octyltriethoxysilane and tridecafluoro-n-octyltrimethoxysilane.

The cross-linking agent (1) is preferably used in combination with the PFPE-containing silane compound. In such a case, a crosslinking reaction (condensation reaction) of —O—$R^{g3}$ bonded to any Si atom of the cross-linking agent (1) and the hydroxyl group or hydrolyzable group bonded to any Si atom of the PFPE-containing silane compound can be made.

The curable composition of the present embodiment may include, for example, 0.1 parts by mass or more, specifically 0.3 parts by mass or more, and 30 parts by mass or less, specifically 10 parts by mass or less of the cross-linking agent (1) based on 100 parts by mass of the PFPE-containing silane compound. The curable composition of the present embodiment may include, for example, 0.1 to 30 parts by mass, specifically 0.3 to 10 parts by mass, more specifically 0.3 to 5.0 parts by mass of the cross-linking agent (1) based on 100 parts by mass of the PFPE-containing silane compound.

The cross-linking agent (1) may contain, for example, 1 mol or more, specifically 2 mol or more of —O—$R^{g3}$ based on 1 mol of the hydroxyl group or hydrolyzable group bonded to any Si atom of the PFPE-containing silane compound, in the curable composition of the present embodiment. The cross-linking agent may contain, for example, 30 mol or less, specifically 20 mol or less, more specifically 10 mol or less of —O—$R^{g3}$ based on 1 mol of the hydroxyl group or hydrolyzable group bonded to any Si atom of the PFPE-containing silane compound. $R^{g3}$ is as defined above. The cross-linking agent (1) may contain, for example, —O—$R^{g3}$, for example, in the range from 1 to 30 mol, specifically in the range from 2 to 20 mol based on 1 mol of the hydroxyl group or hydrolyzable group bonded to any Si atom of the PFPE-containing silane compound.

The cross-linking agent (1) may be included, for example, in the range from 0.1 to 30 parts by mass, specifically in the range from 0.3 to 10 parts by mass based on 100 parts by mass of the curable composition of the present embodiment.

In one embodiment, the cross-linking agent is an organosilicon compound having two or more hydrogen atoms each bonded to a silicon atom (Si—H) in one molecule (hereinafter, also referred to as "cross-linking agent (2)").

In the present embodiment, such Si—H is preferably present at an end of a molecular chain of the cross-linking agent.

In the present embodiment, the cross-linking agent (2) preferably has one or more fluorine-containing groups such as monovalent perfluoroalkyl groups, monovalent perfluorooxyalkyl groups, divalent perfluoroalkylene groups or divalent perfluorooxyalkylene groups in a molecular structure. Such a structure can be contained to thereby improve miscibility and dispersibility of the cross-linking agent and the PFPE-containing compound included in the curable composition of the present embodiment, and also improve uniformity of a cured product of the curable composition of the present embodiment.

The number of carbon atoms in the monovalent perfluoroalkyl group is preferably 1 to 20, more preferably 2 to 10. The perfluoroalkyl group may be linear or branched, and is preferably linear.

The monovalent perfluorooxyalkyl group is preferably a group represented by $R^{fn}$-$PFPE^2$-. $PFPE^2$ is represented by formula:

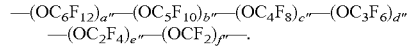

$PFPE^2$ may be linear or branched, and is preferably linear.

In the formula, a", b", c" and d" are each independently an integer of 0 or more and 30 or less, e" and f" are each independently an integer of 1 or more and 200 or less. Preferably, a", b", c", d", e" and f" are each independently an integer of 0 or more and 30 or less. Preferably, the sum of a", b", c", d", e" and f" is 5 or more, more preferably 10 or more, for example, 10 or more and 100 or less. The occurrence order of the respective repeating units in parentheses with the subscript a", b", c", d", e" or f" is not limited in the formula. The ratio of e" to f" is less than 1.0.

Here, a", b", c", d", e" and f" may have the same meanings as a, b, c, d, e and f of PFPE, respectively. Examples of specific structures of the respective repeating units contained in PFPE$^2$ can include those exemplified as the respective repeating units of PFPE.

Preferably, PFPE$^2$ is —(OC$_4$F$_8$)$_{c''}$—(OC$_3$F$_6$)$_{d''}$—(OC$_2$F$_4$)$_{e''}$—(OCF$_2$)$_{f''}$—, wherein c" and d" are each independently an integer of 0 or more and 30 or less, e" and f" are each independently an integer of 1 or more and 200 or less, preferably 5 or more and 200 or less, more preferably 10 or more and 200 or less, and the occurrence order of the respective repeating units in parentheses with the subscript c", d", e" or f" is not limited in the formula. Preferably, PFPE$^2$ is —(OCF$_2$CF$_2$CF$_2$CF$_2$)$_{c''}$—(OCF$_2$CF$_2$CF$_2$)$_{d''}$—(OCF$_2$CF$_2$)$_{e''}$—(OCF$_2$)$_{f''}$—. In one embodiment, PFPE$^2$ may be —(OC$_2$F$_4$)$_{e''}$—(OCF$_2$)$_{f''}$—, wherein e" and f" are each independently an integer of 1 or more and 200 or less, preferably 5 or more and 200 or less, more preferably 10 or more and 200 or less, and the occurrence order of the respective repeating units in parentheses with the subscript e" or f" is not limited in the formula.

In the formulae, each Rf", at each occurrence, independently represents a chlorine atom, a fluorine atom, or an alkyl group having 1 to 16 carbon atoms, the group being optionally substituted with one or more fluorine atoms or chlorine atoms.

The "alkyl group having 1 to 16 carbon atoms" with respect to the alkyl group having 1 to 16 carbon atoms, the group being optionally substituted with one or more fluorine atoms, is optionally linear or branched, is preferably a linear or branched alkyl group having 1 to 6 carbon atoms, particularly 1 to 3 carbon atoms, more preferably a linear alkyl group having 1 to 3 carbon atoms.

Rf" is preferably a fluorine atom, or an alkyl group having 1 to 16 carbon atoms, the group being optionally substituted with one or more fluorine atoms, more preferably a CF$_2$H—C$_{1-15}$ fluoroalkylene group or a C$_{1-16}$ perfluoroalkyl group, further preferably a C$_{1-16}$ perfluoroalkyl group.

The perfluoroalkyl group having 1 to 16 carbon atoms may be linear or branched, and is preferably a linear or branched perfluoroalkyl group having 1 to 6 carbon atoms, in particular, 1 to 3 carbon atoms, more preferably a linear perfluoroalkyl group having 1 to 3 carbon atoms, specifically —CF$_3$, —CF$_2$CF$_3$, or —CF$_2$CF$_2$CF$_3$.

Preferably, the monovalent perfluorooxyalkyl group is Rf"—(OC$_2$F$_4$)$_{e''}$—(OCF$_2$)$_{f''}$—, wherein e" and f" are each independently an integer of 1 or more and 200 or less, preferably 5 or more and 200 or less, more preferably 10 or more and 200 or less, and the occurrence order of the respective repeating units in parentheses with the subscript e" or f" is not limited in the formula.

The ratio of e" to f" in the monovalent perfluorooxyalkyl group is preferably 0.10 or more, more preferably 0.20 or more, further preferably 0.40 or more, and preferably less than 1.00, more preferably 0.85 or less, further preferably 0.80 or less.

The ratio of e" to f" in the monovalent perfluorooxyalkyl group is preferably 0.1 or more and less than 1.0, more preferably 0.20 or more and 0.90 or less, further preferably 0.40 or more and 0.85 or less, particularly preferably 0.40 or more and 0.80 or less.

The number of carbon atoms in the divalent perfluoroalkylene group is preferably 1 to 20, more preferably 2 to 10. The perfluoroalkylene group may be linear or branched, and is preferably linear.

The divalent perfluorooxyalkylene group is preferably represented by -PFPE$^2$-, and is more preferably a group represented by —(OC$_4$F$_8$)$_{c''}$—(OC$_3$F$_6$)$_{d''}$—(OC$_2$F$_4$)$_{e''}$—(OCF$_2$)$_{f''}$—. Here, c", d", e", and f" are as defined above. The perfluorooxyalkyl group may be linear or branched, and is preferably linear. PFPE$^2$ is as defined above.

The fluorine-containing group is preferably the monovalent perfluoroalkyl group or the divalent perfluoroalkylene group.

The fluorine-containing group can be linked to any silicon atom by a divalent organic group. The divalent organic group is as defined above.

For example, the divalent organic group may be any of an alkylene group, an arylene group, and a combination thereof, or may be such a group with an ether bond oxygen atom, an amide bond, a carbonyl bond, or the like interposed. Examples of such a divalent organic group include groups having 2 to 12 carbon atoms, such as

—CH$_2$CH$_2$—,

—CH$_2$CH$_2$CH$_2$—,

—CH$_2$CH$_2$CH$_2$OCH$_2$—,

—CH$_2$CH$_2$CH$_2$—NH—CO—,

—CH$_2$CH$_2$CH$_2$—N(Ph)-CO— (provided that Ph is a phenyl group.),

—CH$_2$CH$_2$CH$_2$—N(CH$_3$)—CO—,

—CH$_2$CH$_2$CH$_2$—O—CO—. A left portion and a right portion of the divalent organic group are bonded to a Si atom and a fluorine-containing group, respectively.

In the present embodiment, examples of any group of the cross-linking agent (2), which is a monovalent substituent bonded to any silicon atom and which is other than the fluorine-containing group, include alkyl groups such as a methyl group, an ethyl group, a propyl group, a butyl group, a hexyl group, a cyclohexyl group, an octyl group and a decyl group; alkenyl groups such as a vinyl group and an allyl group; aryl groups such as a phenyl group, a tolyl group and a naphthyl group; aralkyl groups such as a benzyl group and a phenylethyl group, and any substituted or unsubstituted hydrocarbon groups having 1 to 20 carbon atoms, where at least some hydrogen atoms of such a group is substituted with a chlorine atom, a cyano group or the like, such as a chloromethyl group, a chloropropyl group and a cyanoethyl group.

Preferably, the cross-linking agent (2) does not have any alkoxy group and epoxy group as a substituent bonded to any silicon atom.

In the present embodiment, the cross-linking agent (2) may be a cyclic, linear or three-dimensional network agent, or a combination thereof.

In the present embodiment, the number of silicon atoms contained in the cross-linking agent (2) is not limited, and may be usually 2 to 60, preferably about 3 to 30.

In the present embodiment, examples of the cross-linking agent (2) may include the following compounds. Such a compound may be used singly or in combinations of two or more kinds thereof.

In the following formulae:

PFPE², at each occurrence, each independently is as defined above (in the following formulae, a group represented by PFPE² is bonded to a group represented by $R^f$ on an oxygen atom at an end);

Rf", at each occurrence, each independently is as defined above;

$R^{k3}$, at each occurrence, is each independently an alkyl group having 1 to 10 carbon atoms or an alkoxy group represented by $OR^{k7}$, preferably a methyl group or an alkoxy group represented by $OR^{k7}$, more preferably a methyl group;

$R^{k4}$, at each occurrence, is each independently a hydrogen atom, an alkyl group having 1 to 10 carbon atoms or an alkoxy group represented by $OR^{k7}$, preferably a hydrogen atom or an alkoxy group represented by $OR^{k7}$, more preferably a hydrogen atom;

$R^{k5}$, at each occurrence, is each independently a hydrogen atom, an alkyl group having 1 to 10 carbon atoms or an alkoxy group represented by $OR^{k7}$, preferably a hydrogen atom or an alkoxy group represented by $OR^{k7}$, more preferably a hydrogen atom;

$R^{k6}$, at each occurrence, is each independently a hydrogen atom, a fluorine atom, or an alkylene group where one or more hydrogen atoms are each substituted with a fluorine atom, preferably a hydrogen atom;

$R^{k7}$, at each occurrence, is each independently an alkyl group having 1 to 10 carbon atoms, preferably an alkylene group having 1 to 6 carbon atoms;

the number of carbon atoms contained in the alkylene group where one or more hydrogen atoms are each substituted with a fluorine atom is preferably 1 to 8, more preferably 1 to 6;

$R^{k8}$ is represented by $-(O-(CH_2)_{\alpha 5})_{\alpha 6}-$ (where an oxygen atom is bonded to a group represented by $-(CR^{k6}_2)_{\alpha 1}$);

α1, at each occurrence, is each independently an integer of 1 to 10, preferably 2 or 3;

2, at each occurrence, is each independently an integer of 1 to 50, preferably 10;

α3, at each occurrence, is each independently an integer of 1 to 50, preferably an integer of 3 to 5;

α4, at each occurrence, is each independently an integer of 1 to 50, preferably an integer of 3 to 5;

α5 is an integer of 1 to 6, preferably 1 to 3, more preferably 1; and

α6 is 0 or 1.

[Formula 37]

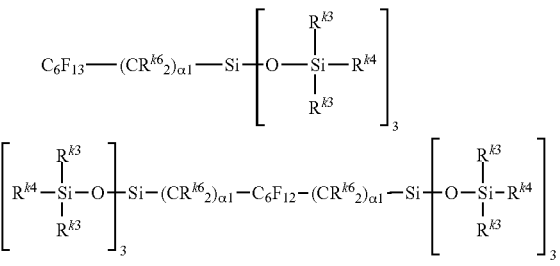

[Formula 38]

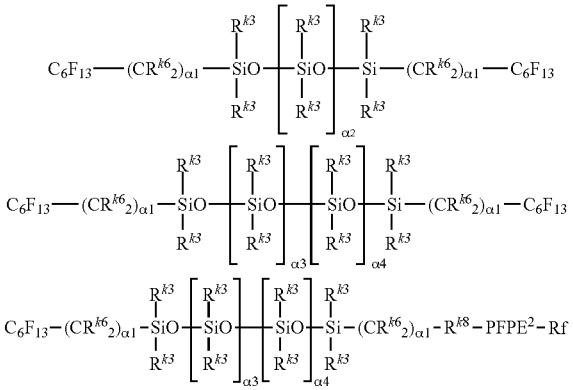

[Formula 39]

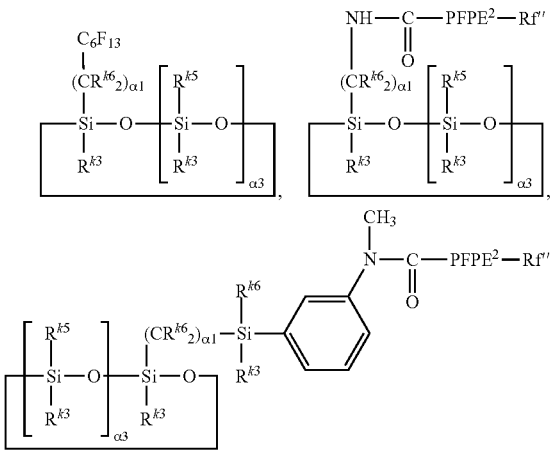

In the present embodiment, the content of the cross-linking agent (2) may be an amount effective for curing the PFPE-containing compound.

The cross-linking agent (2) is preferably used together with the PFPE-containing unsaturated compound. In such a case, an addition reaction may occur by Si—H of the cross-linking agent (2) and a carbon-carbon double bond of the PFPE-containing unsaturated compound.

The content of the cross-linking agent (2) is preferably in the range from 0.5 to 5.0 mol, more preferably in the range from 0.8 to 3.0 mol in terms of a hydrogen atom bonded to a silicon atom contained in the cross-linking agent (hydrosilyl group, namely, SiH group) based on 1 mol of an alkenyl group contained in the PFPE-containing unsaturated compound. The curable composition of the present embodiment may include such a content of the cross-linking agent to thereby contribute to formation of a cured product having an appropriate degree of crosslink, and reduce foaming in curing.

In one embodiment, the cross-linking agent is an organosilicon compound having at least two $-O-R^{g3}$ each bonded to a Si atom (cross-linking agent (1)). $R^{g3}$ is as defined above.

In one embodiment, the cross-linking agent is an organosilicon compound having two or more hydrogen atoms each bonded to a silicon atom (Si—H) in one molecule (cross-linking agent (2)).

The cross-linking agent may be used singly or in combinations of two or more kinds thereof.

The curable composition used in the present invention may further include a catalyst.

The catalyst promotes a condensation reaction of the PFPE-containing compound and the cross-linking agent.

The catalyst may be a metal-based catalyst, an organic acid-based catalyst, an inorganic acid-based catalyst, a base-based catalyst (for example, ammonia, triethylamine or diethylamine), or the like.

Examples of the organic acid-based catalyst may include a compound having carboxylic acid, sulfonic acid or phosphoric acid, and may specifically include acetic acid, trifluoroacetic acid, methanesulfonic acid, toluenesulfonic acid and alkylphosphoric acid.

Examples of the inorganic acid-based catalyst may include hydrochloric acid and sulfuric acid.

The metal-based catalyst preferably contains a transition metal atom.

The catalyst is preferably a metal-based catalyst.

In one embodiment, examples of any metal atom contained in the metal-based catalyst may include titanium, zirconium and tin. In particular, titanium or zirconium is preferably used.

In the present embodiment, the metal-based catalyst preferably has alkoxide (—O—$R^h$) as a ligand. Such a metal-based catalyst is preferably at least one selected from the group consisting of tetra-n-butyl titanate, tetraisopropyl titanate, n-butyl zirconate, n-propyl zirconate, dibutyltin dimethoxide and dibutyltin dilaurate, more preferably at least one selected from the group consisting of tetraisopropyl titanate and n-propyl zirconate. Such a metal-based catalyst is used to thereby promote a condensation reaction of the PFPE-containing compound (for example, PFPE-containing silane compound) and the cross-linking agent. Such a metal-based catalyst can be easily dissolved or dispersed in the curable composition and can contribute to promotion of a uniform reaction. The curable composition of the present embodiment, which includes such a metal-based catalyst, can include less foreign substances and can contribute to formation of a cured product of the curable composition, having high transparency.

In the present embodiment, $R^h$ is preferably an alkyl group having 1 to 4 carbon atoms. A catalyst having such an alkyl group is used to particularly promote a condensation reaction.

In the present embodiment, $R^h$ is further preferably an alkyl group having 1 to 3 carbon atoms. The alkyl group having 1 to 3 carbon atoms is, namely, a methyl group, an ethyl group, a n-propyl group or an i-propyl group. The catalyst, which has such $R^h$, may be easily dissolved in a solvent and can contribute to promotion of a uniform reaction.

The catalyst of the present embodiment is preferably used together with the PFPE-containing silane compound.

The catalyst of the present embodiment is preferably used together with the PFPE-containing silane compound and the cross-linking agent (1).

In the present embodiment, the curable composition preferably includes 0.05 parts by mass or more, more preferably 0.07 parts by mass or more of the catalyst based on 100 parts by mass of the PFPE-containing silane compound. The curable composition of the present embodiment preferably includes 1.0 part by mass or less, more preferably 0.7 parts by mass or less of the catalyst based on 100 parts by mass of the PFPE-containing silane compound. The curable composition includes the concentration of the catalyst, thereby allowing a condensation reaction of the PFPE-containing compound and the cross-linking agent to be particularly promoted.

In the present embodiment, the curable composition preferably includes 0.05 to 1.0 parts by mass, more preferably 0.07 to 0.7 parts by mass of the catalyst based on 100 parts by mass of the PFPE-containing silane compound.

In one embodiment, the catalyst may contain at least one metal atom selected from the group consisting of platinum, rhodium, ruthenium, iridium and palladium.

In the present embodiment, platinum or a platinum compound is preferably used as the catalyst. Such a catalyst has the advantages of a reduction in catalyst cost and catalyst availability.

Examples of the platinum compound may include hydrogen chloroplatinate or a complex of hydrogen chloroplatinate and olefin such as ethylene, a complex thereof with alcohol or vinylsiloxane, and metallic platinum carried on silica, alumina, carbon or the like.

Examples of the catalyst containing rhodium, ruthenium, iridium or palladium may include $RhCl(PPh_3)_3$, $RhCl(CO)(PPh_3)_2$, $Ru_3(CO)_{12}$, $IrCl(CO)(PPh_3)_2$ and $Pd(PPh_3)_4$. In the formulae, Ph is a phenyl group.

In the present embodiment, the catalyst may be used in the form of a solid when the catalyst is a solid, and hydrogen chloroplatinate or a complex, dissolved in a proper solvent, is preferably used with being miscible with the PFPE-containing unsaturated compound in order to provide a more uniform cured product.

In the present embodiment, the catalyst is preferably used together with the PFPE-containing unsaturated compound.

In the present embodiment, the catalyst is preferably used together with the PFPE-containing unsaturated compound and the cross-linking agent (2).

In the present embodiment, the catalyst may be included in the curable composition in an effective amount so as to be able to contribute to a reaction, for example, in an effective amount so as to be able to contribute to a reaction with serving as a hydrosilylation catalyst. The content of the catalyst can be appropriately increased or decreased depending on a desired curing rate. The content of the catalyst is usually preferably 0.1 to 500 ppm (in terms of metal atom) based on 100 parts by mass of the PFPE-containing compound (A).

In the present embodiment, the catalyst can serve as a hydrosilylation catalyst. Such a hydrosilylation catalyst can promote an addition reaction of an alkenyl group in the PFPE-containing unsaturated compound and a hydrogen atom bonded to a silicon atom in the cross-linking agent (hydrosilyl group).

The catalyst may be used singly or in combinations of two or more kinds thereof.

For example, the curable composition used in the present invention may further include a solvent. The composition, which includes a solvent, is thus improved in handleability. In the case where such a curable composition is used to form a layer, the layer formed can be a continuous thin film. Such a curable composition can contribute to formation of a thin film having any thickness.

The composition preferably includes 300 parts by mass or less, more preferably 200 parts by mass or less, further preferably 100 parts by mass or less of the solvent based on 100 parts by mass of the total of the fluorine-containing silane compound, the organosilicon compound and the catalyst. The composition includes 1 part by mass or more, more preferably 20 parts by mass or more, further preferably 50 parts by mass or more of the solvent based on 100 parts by mass of the total of the fluorine-containing silane compound, the organosilicon compound and the catalyst.

The solvent is preferably included in the range from 1 to 300 parts by mass, more preferably in the range from 20 to 200 parts by mass, further preferably in the range from 50 to 100 parts by mass based on 100 parts by mass of the total of the PFPE-containing compound, the cross-linking agent and the catalyst.

Examples of the solvent include:

a fluorine atom-containing solvent selected from the group consisting of perfluorohexane, $CF_3CF_2CHCl_2$, $CF_3CH_2CF_2CH_3$, $CF_3CHFCHFC_2F_5$, 1,1,1,2,2,3,3,4,4,5,5,6,6-tridecafluorooctane, 1,1,2,2,3,3,4-heptafluorocyclopentane ((Zeorora H (trade name) or the like), $C_4F_9OCH_3$, $C_4F_9OC_2H_5$, $CF_3CH_2OCF_2CHF_2$, $C_6F_{13}CH=CH_2$, xylene hexafluoride, perfluorobenzene, methylpentadecafluoroheptylketone, trifluoroethanol, pentafluoropropanol, hexafluoroisopropanol, $HCF_2CF_2CH_2OH$, methyltrifluoromethanesulfonate, trifluoroacetic acid, $CF_3O(CF_2CF_2O)_{m1}(CF_2O)_{n1}CF_2CF_3$, wherein m1 and n1 are each independently an integer of 0 or more and 1000 or less and the occurrence order of the respective repeating units in parentheses with m1 or n1 is not limited in the formula, provided that the sum of m1 and n1 is 1 or more, 1,1-dichloro-2,3,3,3-tetrafluoro-1-propene, 1,2-dichloro-1,3,3,3-tetrafluoro-1-propene, 1,2-dichloro-3,3,3-trifluoro-1-propene, 1,1-dichloro-3,3,3-trifluoro-1-propene, 1,1,2-trichloro-3,3,3-trifluoro-1-propene, 1,1,1,4,4,4-hexafluoro-2-butene, ethyl perfluorobutyl ether and methyl perfluorobutyl ether. Such a solvent may be used singly or as a mixture of two or more kinds thereof.

In particular, a preferable solvent is a fluorine atom-containing solvent. The fluorine atom-containing solvent is preferably at least one selected from the group consisting of ethyl perfluorobutyl ether and methyl perfluorobutyl ether. Such a solvent is used to thereby enhance storage stability of the curable composition of the present invention.

In one embodiment, the curable composition may include the PFPE-containing compound, the cross-linking agent, the catalyst and the solvent to thereby allow for formation of a continuous film (herein, sometimes referred to such a film as "uniformity film"), as described above. The continuous film refers to a film not having any region not coated, like a pinhole. In the case where the curable composition of the present invention is used, a thin film having any thickness (for example, 0.1 to 100 µm, specifically 1 to 50 µm) can be formed.

The curable composition enables a gel-like cured product to be formed. The curable composition can be thus suited for use as, for example, a sealing material.

The content of moisture contained in the solvent is preferably 100 ppm by mass or less, more preferably 50 ppm by mass or less. The lower limit of the content of moisture contained in the solvent is not limited, and is, for example, 1 ppm by mass or more. The content of moisture can be measured with a Karl Fischer method. The content of moisture may be in the range to thereby allow storage stability of the curable composition to be enhanced.

The content of moisture contained in the curable composition of the present invention is preferably 20 ppm by mass or less relative to the composition. The lower limit of the content of moisture contained in the curable composition is not limited, and no moisture may be substantially contained (for example, 0 ppm by mass). The content of moisture can be measured with a Karl Fischer method. The content of moisture can be in the range to thereby allow storage stability of the curable composition to be enhanced. The content of moisture can be in the range to thereby allow stability (for example, storage stability) of the curable composition of the present invention to be enhanced.

The viscosity of the curable composition of the present invention is preferably in the range from 5 to 1000 mPa·s. The viscosity of the curable composition is more preferably 500 mPa·s or less, further preferably 300 mPa·s or less, more preferably 100 mPa·s or less, further preferably 60 mPa·s or less, particularly preferably 50 mPa·s or less. The viscosity of the curable composition is more preferably 3 mPa·s or more, further preferably 5 mPa·s or more.

Preferably, the viscosity of the composition for formation of a cured product is in the range from 3 to 500 mPa·s, more preferably in the range from 5 to 300 mPa·s.

The curable composition of the present invention, which has such a viscosity, can be thus more enhanced in handleability.

The viscosity corresponds to a viscosity at 25° C., as determined by a B-type viscometer, and can be measured according to JIS K7117-1:1999.

In a preferable embodiment, the PFPE-containing compound is a PFPE-containing unsaturated compound, the cross-linking agent is an organosilicon compound having two or more hydrogen atoms each bonded to a silicon atom (Si—H) in one molecule, and the catalyst is a metal-based catalyst containing at least one selected from the group consisting of platinum, rhodium, ruthenium, iridium and palladium, preferably platinum or a platinum compound.

In the embodiment, the curable composition can preferably further include an organosilicon compound having one or more hydrolyzable groups each bonded to a silicon atom in one molecule (hereinafter, also referred to as "organosilicon compound (3)"). The organosilicon compound (3) can serve as an adhesion-imparting agent which can impart self-adhesiveness to the curable composition. The hydrolyzable group is as defined above.

The organosilicon compound (3) may be used singly or in combinations of two or more kinds thereof.

The organosilicon compound (3) may have one or more monovalent perfluoroalkyl groups or monovalent perfluorooxyalkyl groups. Such a structure can be contained to thereby particularly improve miscibility and dispersibility of the organosilicon compound (3) and the PFPE-containing unsaturated compound contained in the curable composition, and improve uniformity of a cured product of the curable composition.

The organosilicon compound (3) may have one or more hydrogen atoms each bonded to a silicon atom in one molecule from the viewpoint of addition reactivity with the PFPE-containing unsaturated compound.

The organosilicon compound (3) is preferably organosiloxane or trialkoxysilane having one or more alkoxysilyl groups each bonded to a silicon atom via a carbon atom or a carbon atom and an oxygen atom.

The siloxane backbone of the organosiloxane in the organosilicon compound (3) may be a cyclic, linear or branched backbone, or a combination thereof. The organosiloxane may be the organosiloxane represented by the following general formula.

[Formula 40]

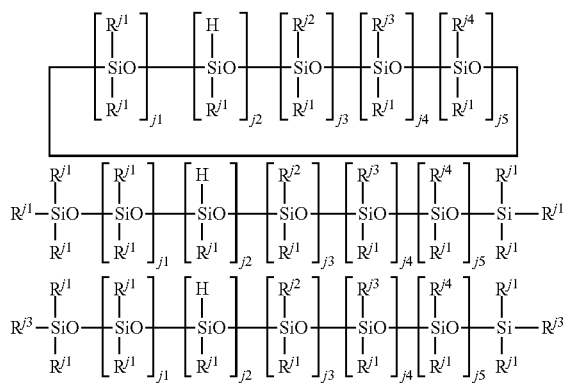

In the general formulae, j1, at each occurrence, is preferably each independently an integer of 0 to 50, more preferably an integer of 0 to 20. In the general formulae, j2, at each occurrence, is preferably each independently an integer of 0 to 50, more preferably an integer of 0 to 20. In the general formulae, j3, at each occurrence, is preferably each independently an integer of 1 to 50, more preferably an integer of 1 to 20. In the general formulae, j4, at each occurrence, is preferably each independently an integer of 0 to 50, more preferably an integer of 0 to 20. In the general formulae, j5, at each occurrence, is preferably each independently an integer of 0 to 50, more preferably an integer of 0 to 20. The sum of j1, j2, j3, j4 and j5 is an integer which allows the weight average molecular weight in terms of polystyrene according to gel permeation chromatography (GPC) to satisfy 500 to 20,000.

In the general formulae, $R^{j1}$, at each occurrence, is each independently a halogen-substituted or unsubstituted monovalent hydrocarbon group. The number of carbon atoms contained in the halogen-substituted or unsubstituted monovalent hydrocarbon group of $R^{j1}$ is preferably in the range from 1 to 10, more preferably in the range from 1 to 8. Specific examples of such a monovalent hydrocarbon group may include alkyl groups such as a methyl group, an ethyl group, a propyl group, a butyl group, a hexyl group, a cyclohexyl group and an octyl group; aryl groups such as a phenyl group and a tolyl group; aralkyl groups such as a benzyl group and a phenylethyl group, or a substituted monovalent hydrocarbon group where some or all hydrogen atoms of such a group are substituted with a halogen atom such as a fluorine atom. In particular, the monovalent hydrocarbon group is more preferably a methyl group.

In the general formulae, $R^{j2}$ represents an alkoxysilyl group bonded to a silicon atom via a carbon atom or a carbon atom and an oxygen atom, and specific examples thereof include —$R^{j5}$—Si(OR$^{j6}$)$_3$, or a group represented by the following formula.

[Formula 41]

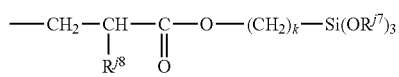

In the formulae, $R^{j5}$ is a divalent hydrocarbon group having 1 to 10 carbon atoms, in particular, 1 to 4 carbon atoms, specifically, an alkylene group such as a methylene group, an ethylene group, a propylene group, a butylene group, a hexylene group, a cyclohexylene group or an octylene group, and $R^{j6}$ is a monovalent hydrocarbon group having 1 to 8 carbon atoms, in particular, 1 to 4 carbon atoms, specifically, for example, an alkyl group such as a methyl group, an ethyl group or a n-propyl group. $R^{j7}$ is a monovalent hydrocarbon group having 1 to 8 carbon atoms, in particular, 1 to 4 carbon atoms, specifically, an alkyl group such as a methyl group, an ethyl group or a n-propyl group, $R^{j8}$ is a hydrogen atom or a methyl group, and k is an integer of 2 to 10.

In the general formulae, $R^{j3}$ is a group represented by the following general formula:

Herein, a right portion of $Z^{j1}$ is bonded to $Rf^{j1}$.

In the formula, $Z^{j1}$ is a group represented by —(CH$_2$)$_{j6}$—, —(CH$_2$)$_{j7}$—$X^{j1}$—, wherein $X^{j1}$ is —OCH$_2$—, or —$Y^{j1}$—NR$^{j9}$—CO—, wherein $Y^{j1}$ is —CH$_2$— or an o, m or p-dimethylsilylphenylene group represented by the following structural formula:

[Formula 42]

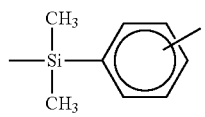

wherein a phenylene group is bonded to a N atom, and $R^{j9}$ is a hydrogen atom, or a substituted or unsubstituted monovalent hydrocarbon group preferably having 1 to 12 carbon atoms, in particular, 1 to 10 carbon atoms, and j6 and j7, at each occurrence, are each independently an integer of 1 to 10, preferably an integer of 1 to 5. In the formulae, $Rf^{j1}$ represents a monovalent perfluoroalkyl group or a monovalent perfluorooxyalkyl group.

The monovalent perfluoroalkyl group or the monovalent perfluorooxyalkyl group is as defined above.

$R^{j4}$ is an epoxy group bonded to a silicon atom via a carbon atom or a carbon atom and an oxygen atom, and specific examples thereof may include the following groups:

[Formula 43]

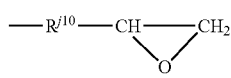

wherein $R^{j10}$ is a divalent hydrocarbon group having 1 to 10 carbon atoms, in particular, 1 to 5 carbon atoms, optionally with an oxygen atom interposed, specifically, an alkylene group such as a methylene group, an ethylene group, a propylene group, a butylene group, a hexylene group, a cyclohexylene group or an octylene group.

Specific examples of the organosiloxane used as the organosilicon compound (3) include any organosiloxane represented by the following structural formula. In the following, a group represented by PFPE$^2$ is bonded to a group represented by Rf, on an oxygen atom at an end.

[Formula 44]

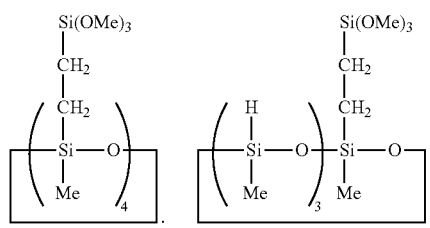

[Formula 45]

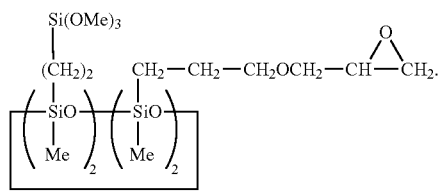

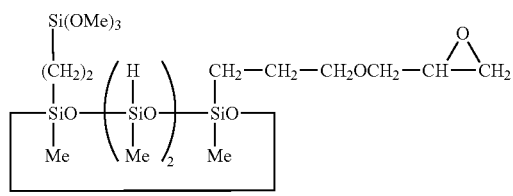

[Formula 46]

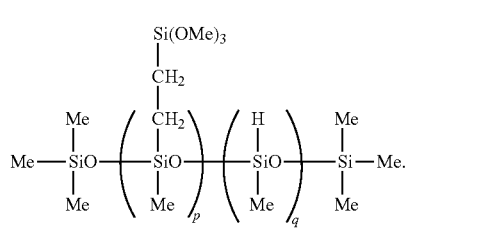

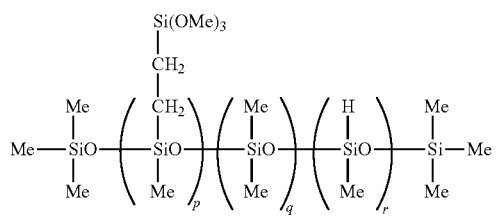

[Formula 47]

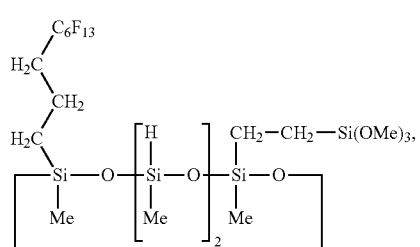

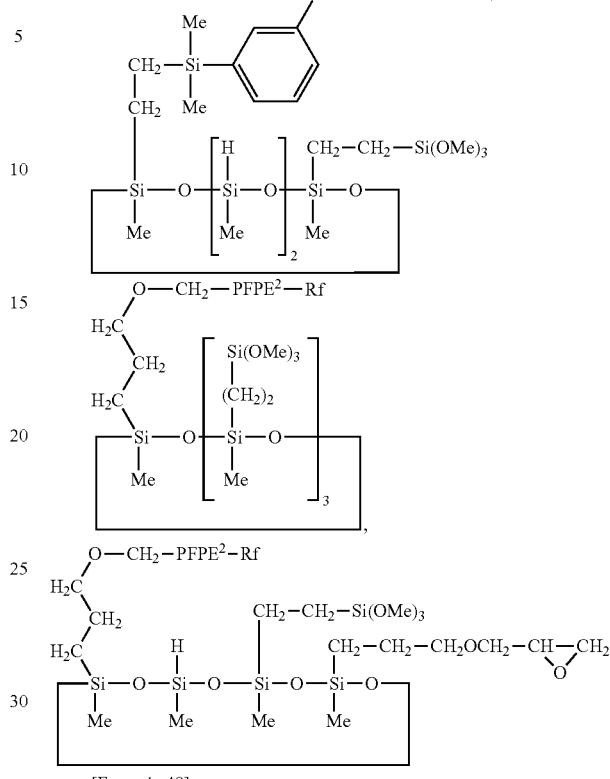

[Formula 48]

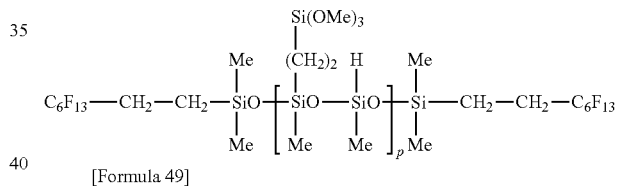

[Formula 49]

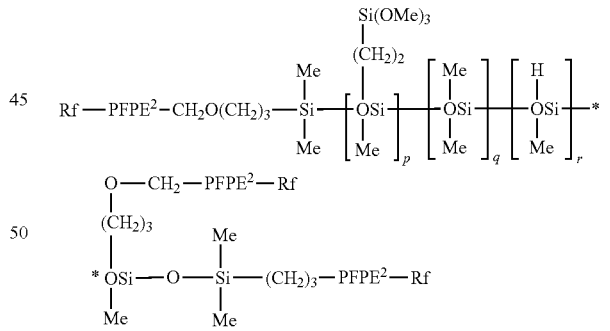

In the formulae, Me represents a methyl group, and p, q and r, at each occurrence, are each independently an integer of 0 or more. $PFPE^2$ and Rf are as defined above.

The trialkoxysilane used as the organosilicon compound (3) is not limited, and is preferably any silane having a reactive organic group other than an alkoxy group in the same molecule, such as vinyltrimethoxysilane, 3-glycidoxypropyltrimethoxysilane, 3-glycidoxypropyltriethoxysilane, 3-aminopropyltrimethoxysilane, 3-(methacryloxypropyl) trimethoxysilane, 2-(3,4-epoxycyclohexyl)ethyltrimethoxysilane, N-2-(aminoethyl)-3-aminopropyltrimethoxysilane, N-phenyl-3-aminopropyltrimethoxysilane, 3-mercaptopropyltrimethoxysilane or 3-isocyanatopropyltriethoxysilane, or fluorine-containing trialkoxysilane such as perfluoropropyltrimethoxysilane.

The amount of the organosilicon compound (3) compounded is preferably in the range from 0.01 to 10 parts by mass, more preferably in the range from 0.05 to 5 parts by mass based on 100 parts by mass of the PFPE-containing unsaturated compound. The organosilicon compound (3) can be included in the range to thereby allow the curable composition to have sufficient adhesiveness and have appropriate fluidity and curability. Such a curable composition can be favorable in physical hardness.

In the case where the curable composition includes the PFPE-containing unsaturated compound, the cross-linking agent (2) and the organosilicon compound (3), the curable composition can further include a hydrolysis catalyst (hereinafter, also referred to as "hydrolysis catalyst (E)"). The hydrolysis catalyst has a catalyst function for enhancing hydrolyzability of the organosilicon compound (3).

The hydrolysis catalyst is not limited as long as the catalyst does not impair addition curability of the composition, and examples thereof include organotitanium compounds such as titanium tetraisopropoxide, titanium tetra-n-butoxide and titanium tetraacetylacetonate; organozirconium compounds such as zirconium tetra-n-propoxide, zirconium tetra-n-butoxide and zirconium tetraacetylacetonate; organotin compounds such as dibutyltin dilaurate, dibutyltin diacetate and dibutyltin acetylacetonate; organoaluminum compounds such as aluminum trisacetylacetonate, aluminum trisethylacetoacetate and diisopropoxy aluminum ethylacetoacetate; and other acidic catalysts and basic catalysts. In particular, at least one selected from the group consisting of such organotitanium compounds, organozirconium compounds, organotin compounds and organoaluminum compounds is preferably used from the viewpoint of storage stability of the curable composition of the present embodiment. The hydrolysis catalyst may be used singly or in combinations of two or more kinds thereof.

The amount of the hydrolysis catalyst compounded is preferably in the range from 0.001 to 5 parts by mass, more preferably in the range from 0.01 to 1 part by mass based on 100 parts by mass of the PFPE-containing unsaturated compound. The hydrolysis catalyst may be included in the range in the curable composition of the present embodiment, thereby exerting a sufficient catalyst effect. The hydrolysis catalyst can be included in the range, thereby allowing the curable composition of the present embodiment to have appropriate fluidity. The hydrolysis catalyst can also be prevented from being cured into a gel.

The curable composition used in the present invention may further include any compound represented by the following formula (A1), (B1), (C1) or (D1).

[Formula 50]

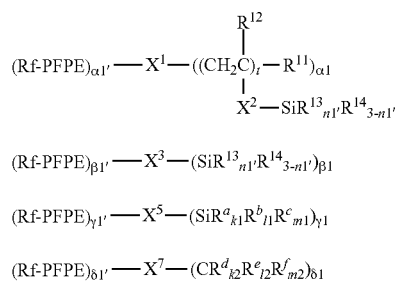

Any portion of the descriptions of formulae (A1), (B1), (C1) and (D1), overlapped with those of (A), (B), (C) and (D), will be omitted.

In the formulae, Rf, at each occurrence, independently represents an alkyl group having 1 to 16 carbon atoms, optionally substituted with one or more fluorine atoms.

The "alkyl group having 1 to 16 carbon atoms" with respect to the alkyl group having 1 to 16 carbon atoms, the group being optionally substituted with one or more fluorine atoms, is optionally linear or branched, is preferably a linear or branched alkyl group having 1 to 6 carbon atoms, particularly 1 to 3 carbon atoms, more preferably a linear alkyl group having 1 to 3 carbon atoms.

Rf is preferably an alkyl group having 1 to 16 carbon atoms, the group being optionally substituted with one or more fluorine atoms, more preferably a $CF_2H$—$C_{1-15}$ fluoroalkylene group or a $C_{1-16}$ perfluoroalkyl group, further preferably a $C_{1-16}$ perfluoroalkyl group.

The perfluoroalkyl group having 1 to 16 carbon atoms may be linear or branched, and is preferably a linear or branched perfluoroalkyl group having 1 to 6 carbon atoms, in particular, 1 to 3 carbon atoms, more preferably a linear perfluoroalkyl group having 1 to 3 carbon atoms, specifically —$CF_3$, —$CF_2CF_3$, or —$CF_2CF_2CF_3$.

In formula (A1), $\alpha 1$ is an integer of 1 to 9 and $\alpha 1'$ is an integer of 1 to 9. Here, $\alpha 1'$ may be varied depending on the valence of X'. In formula (A1), the sum of $\alpha 1$ and $\alpha 1'$ is the same as the valence of $X^1$. For example, in the case where $X^1$ is a decavalent organic group, the sum of $\alpha 1$ and $\alpha 1'$ may be 10, for example, $\alpha 1$ may be 9 and $\alpha 1'$ may be 1, $\alpha 1$ may be 5 and $\alpha 1'$ may be 5, or $\alpha 1$ may be 1 and $\alpha 1'$ may be 9. In the case where $X^1$ is a divalent organic group, $\alpha 1$ and $\alpha 1'$ are 1.

$X^1$ is preferably a 2-7 valent, more preferably 2-4 valent, further preferably divalent organic group.

In one embodiment, $X^1$ is a 2-4 valent organic group, $\alpha 1$ is 1 to 3, and $\alpha 1'$ is 1.

In another embodiment, $X^1$ is a divalent organic group, $\alpha 1$ is 1, and $\alpha 1'$ is 1.

In formula (A1), n1' with respect to a (—$SiR^{13}_{n1'}R^{14}_{3-n1'}$) unit is independently an integer of 0 to 3, preferably 1 to 3, more preferably 3. In the formula, at least one n1' is an integer of 1 to 3, namely, there is not any case where all n1' are simultaneously 0. In other words, at least one $R^{13}$ is present in formula (A1).

In formula (B1), $\beta 1$ is an integer of 1 to 9 and $\beta 1$ is an integer of 1 to 9. Such $\beta 1$ and $\beta 1$ may be varied depending on the valence of $X^3$. In formula (B1), the sum of $\beta 1$ and $\beta 1$ is the same as the valence of, $X^3$. For example, in the case where $X^3$ is a decavalent organic group, the sum of $\beta 1$ and $\beta 1$ may be 10, for example, $\beta 1$ may be 9 and $\beta 1$ may be 1, $\beta 1$ may be 5 and $\beta 1$ may be 5, or $\beta 1$ may be 1 and $\beta 1$ may be 9. In the case where $X^3$ is a divalent organic group, $\beta 1$ and $\beta 1$ are 1. In the case where $X^3$ is a single bond, $\beta 1$ and $\beta' 1$ are 1.

$X^3$ is preferably a 2-7 valent, more preferably 2-4 valent, further preferably divalent organic group.

In one embodiment, $X^3$ is a 2-4 valent organic group, $\beta 1$ is 1 to 3, and $\beta 1$ is 1.

In another embodiment, $X^3$ is a divalent organic group, $\beta 1$ is 1, and $\beta 1$ is 1.

In formula (B1), n1' is as defined for formula (A1).

In formula (C1), $\gamma 1$ is an integer of 1 to 9 and $\gamma 1'$ is an integer of 1 to 9. Such $\gamma 1$ and $\gamma 1'$ may be varied depending on the valence of $X^5$. In formula (C1), the sum of $\gamma 1$ and $\gamma 1'$ is the same as the valence of $X^5$. For example, in the case where $X^5$ is a decavalent organic group, the sum of $\gamma 1$ and γ1' may be 10, for example, γ1 may be 9 and γ1' may be 1, γ1 may be 5 and γ1' may be 5, or γ1 may be 1 and γ1' may be 9. In the case where $X^5$ is a divalent organic group, γ1 and γ1' are 1. In the case where $X^5$ is a single bond, γ1 and γ'1 are 1.

$X^5$ is preferably a 2-7 valent, more preferably 2-4 valent, further preferably divalent organic group.

In one embodiment, $X^5$ is a 2-4 valent organic group, γ1 is 1 to 3, and γ1' is 1.

In another embodiment, $X^5$ is a divalent organic group, γ1 is 1, and γ1' is 1.

In formula (D1), δ1 is an integer of 1 to 9 and δ1' is an integer of 1 to 9. Such δ1 and δ1' may be varied depending on the valence of $X^7$. In formula (D1), the sum of δ1 and δ1' is the same as the valence of $X^7$. For example, in the case where $X^7$ is a decavalent organic group, the sum of δ1 and δ1' may be 10, for example, δ1 may be 9 and δ1' may be 1, δ1 may be 5 and δ1' may be 5, or δ1 may be 1 and δ1' may be 9. In the case where $X^7$ is a divalent organic group, δ1 and δ1' are 1. In the case where $X^7$ is a single bond, δ1 and δ'1 are 1.

$X^7$ is preferably a 2-7 valent, more preferably 2-4 valent, further preferably divalent organic group.

In one embodiment, $X^7$ is a 2-4 valent organic group, δ1 is 1 to 3, and δ1' is 1.

In another embodiment, $X^7$ is a divalent organic group, δ1 is 1, and δ1' is 1.

In one embodiment, the compound represented by formula (A1), (B1), (C1) or (D1) is preferably a compound represented by formula (A1), (C1) or (D1). Such a silane compound can be used to thereby allow adhesion properties to the base material to be enhanced.

In one embodiment, the curable composition of the present invention includes 0.1 mol % or more and 35 mol % or less of any compound represented by formulae (A1), (B1), (C1) and (D1) based on the total of any compound represented by formulae (A), (B), (C) and (D) (hereinafter, also referred to as "component (1)") and any compound represented by formulae (A1), (B1), (C1) and (D1) (hereinafter, also referred to as "component (2)"). The lower limit of the content of any compound represented by formulae (A1), (B1), (C1) and (D1) based on the total of the component (1) and the component (2) may be preferably 0.1 mol %, more preferably 0.2 mol %, further preferably 0.5 mol %, still more preferably 1 mol %, particularly preferably 2 mol %, particularly 5 mol %. The upper limit of the content of any compound represented by formulae (A1), (B1), (C1) and (D1) based on the total of the component (1) and the component (2) may be preferably 35 mol %, more preferably 30 mol %, further preferably 20 mol %, still more preferably 15 mol % or 10 mol %. The content of the compounds represented by formulae (A1), (B1), (C1) and (D1) based on the total of the component (1) and the component (2) is preferably 0.1 mol % or more and 30 mol % or less, more preferably 0.1 mol % or more and 20 mol % or less, further preferably 0.2 mol % or more and 10 mol % or less, still more preferably 0.5 mol % or more and 10 mol % or less, particularly preferably 1 mol % or more and 10 mol % or less, for example, 2 mol % or more and 10 mol % or less or 5 mol % or more and 10 mol % or less. The component (1) and the component (2) can be included in such a range, thereby allowing the curable composition of the present invention to contribute to formation of a cured product favorable in friction durability.

The combination of the component (1) and the component (2) in the curable composition is preferably a combination of a compound represented by formula (A) and a compound represented by formula (A1), a combination of a compound represented by formula (B) and a compound represented by formula (B1), a combination of a compound represented by formula (C) and a compound represented by formula (C1), or a combination of a compound represented by formula (D) and a compound represented by formula (D1).

In such any compound represented by formula (A) and formula (A1), t is preferably 2 or more, more preferably an integer of 2 to 10, further preferably an integer of 2 to 6. Here, t may be 2 or more, thereby allowing a plurality of Si atoms each having $R^{13}$ or $R^{13"}$ to be present and allowing a cured product formed from the curable composition of the present invention to achieve higher durability (for example, friction durability).

In such any compound represented by formula (C) and formula (C1), k1 is preferably 2 or 3, more preferably 3.

In a preferable embodiment, the compound represented by formula (C) has a structure represented by —Si—$(Z^3$—$SiR^{72}_3)_2$, —Si—$(Z^3$—$SiR^{72"}_3)_2$, —Si—$(Z^3$—$SiR^{72}_3)_3$ or —Si—$(Z^3$—$SiR^{72"}_3)_3$, further preferably has a structure represented by —Si—$(Z^3$—$SiR^{72}_3)_3$ or —Si—$(Z^3$—$SiR^{72"}_3)_3$ at an end; the compound represented by formula (C1) has a structure represented by —Si—$(Z^3$—$SiR^{72}_3)_2$ or —Si—$(Z^3$—$SiR^{72}_3)_3$, further preferably has a structure represented by —Si—$(Z^3$—$SiR^{72}_3)_3$ at an end. Such a structure can be at an end, thereby allowing a cured product formed from the curable composition of the present invention to achieve higher durability (for example, friction durability).

Specific examples of the group represented by —Si—$(Z^3$—$SiR^{72}_3)_2$ or —Si—$(Z^3$—$SiR^{72"}_3)_2$ may include —Si—$R^a_2 R^b_{l1} R^c_{m1}$ wherein $R^a$ is a group represented by —$Z^3$—$SiR^{72}_3$ and the sum of l1 and m1 is 1, —Si—$R^{a"}_2 R^{b"}_{l1} R^{c"}_{m1}$ wherein $R^{a"}$ is a group represented by —$Z^3$—$SiR^{72"}_3$ and the sum of l1 and m1 is 1, —Si—$R^{71}_2 R^{72}_{q1} R^{73}_{r1}$ wherein $R^{71}$ is a group represented by —$Z^3$—$SiR^{72}_3$ and the total of q1 and r1 is 1, or —Si—$R^{71}_2 R^{72"}_{q1} R^{73}_{r1}$ wherein $R^{71}$ is a group represented by —$Z^3$—$SiR^{72}_3$ and the total of q1 and r1 is 1.

In such any compound represented by formula (D) and formula (D1), l2 is preferably 2 or 3, more preferably 3.

In a preferable embodiment, the compound represented by formula (D) has a —C—$(Y$—$SiR^{85}_3)_2$, —C—$(Y$—$SiR^{85"}_3)_2$ (specifically, —C—$(Y$—$SiR^{85}_3)_2 R^{83}$, —C—$(Y$—$SiR^{85}_3)_2 R^f$, —C—$(Y$—$SiR^{85"}_3)_2 R^{83}$, or —C—$(Y$—$SiR^{85"}_3)_2 R^f$), —C—$(Y$—$SiR^{85}_3)_3$ or —C—$(Y$—$SiR^{85"}_3)_3$ structure, further preferably a —C—$(Y$—$SiR^{85}_3)_3$ or —C—$(Y$—$SiR^{85"}_3)_3$ structure at an end; and the compound represented by formula (D1) has a —C—$(Y$—$SiR^{85}_3)_2$ (specifically, —C—$(Y$—$SiR^{85}_3)_2 R^{83}$) or —C—$(Y$—$SiR^{85}_3)_3$ structure, further preferably a —C—$(Y$—$SiR^{85}_3)_3$ structure at an end. Such a structure can be at an end, thereby allowing the curable composition of the present invention to contribute to formation of a cured product having higher durability (for example, friction durability).

The curable composition used in the present invention may further include other component. Such other component is not limited, and may include, for example, a (non-reactive) fluoropolyether compound which may be understood as a fluorine-containing oil, preferably a perfluoro(poly)ether compound (hereinafter, referred to as "fluorine-containing oil"), a stabilizing material (dehydrating agent, molecular sieve, magnesium sulfate or methyl o-formate), a viscosity modifier, a filler, a fluorescent agent, a storage stabilizer, a filling agent, a colorant, a heat resistance improver, a cold resistance improver, a rust inhibitor, an adhesiveness improver, a liquid strengthening agent, and/or a polymerization initiator.

The fluorine-containing oil is not limited, and examples thereof include a compound (perfluoro(poly)ether compound) represented by the following general formula (III):

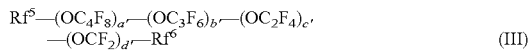

$$Rf^5-(OC_4F_8)_{a'}-(OC_3F_6)_{b'}-(OC_2F_4)_{c'}-(OCF_2)_{d'}-Rf^6 \quad (III)$$

wherein $Rf^5$ represents an alkyl group having 1 to 16 carbon atoms optionally substituted with one or more fluorine atoms (preferably $C_{1-16}$ perfluoroalkyl group), $Rf^6$ represents an alkyl group having 1 to 16 carbon atoms optionally substituted with one or more fluorine atoms (preferably $C_{1-16}$ perfluoroalkyl group), a fluorine atom or a hydrogen atom, and $Rf^5$ and $Rf^6$ are more preferably, each independently, a $C_{1-3}$ perfluoroalkyl group; and a', b', c' and d' represent the respective four numbers of repeating units in perfluoro(poly)ether constituting a main backbone of the polymer and are mutually independently an integer of 0 or more and 300 or less, the sum of a', b', c' and d' is at least 1, preferably 1 to 300, more preferably 20 to 300, the occurrence order of the respective repeating units in parentheses with the subscript a', b', c' or d' is not limited in the formula, and, among such repeating units, $-(OC_4F_8)-$ may be any of $-(OCF_2CF_2CF_2CF_2)-$, $-(OCF(CF_3)CF_2CF_2)-$, $-(OCF_2CF(CF_3)CF_2)-$, $-(OCF_2CF_2CF(CF_3))-$, $-(OC(CF_3)_2CF_2)-$, $-(OCF_2C(CF_3)_2)-$, $-(OCF(CF_3)CF(CF_3))-$, $-(OCF(C_2F_5)CF_2)-$ and $-(OCF_2CF(C_2F_5))-$, and is preferably $-(OCF_2CF_2CF_2CF_2)-$, and $-(OC_3F_6)-$ may be any of $-(OCF_2CF_2CF_2)-$, $-(OCF(CF_3)CF_2)-$ and $-(OCF_2CF(CF_3))-$, and is preferably $-(OCF_2CF_2CF_2)-$, and, for example, $-(OC_2F_4)-$ may be any of $-(OCF_2CF_2)-$ and $-(OCF(CF_3))-$, and is preferably $-(OCF_2CF_2)-$.

Examples of the perfluoro(poly)ether compound represented by general formula (III) include a compound represented by any of the following general formulae (IIIa) and (IIIb) (which may be adopted singly or as a mixture of two or more kinds thereof).

$$Rf^5-(OCF_2CF_2CF_2)_{b''}-Rf^6 \quad (IIIa)$$

$$Rf^5-(OCF_2CF_2CF_2CF_2)_{a''}-(OCF_2CF_2CF_2)_{b''}-(OCF_2CF_2)_{c''}-(OCF_2)_{d''}-Rf^6 \quad (IIIb)$$

In such formulae, $Rf^5$ and $Rf^6$ are as described above; in formula (IIIa), b" is an integer of 1 or more and 100 or less; in formula (IIIb), a" and b" are each independently an integer of 1 or more and 30 or less, and c" and d" are each independently an integer of 1 or more and 300 or less, and the occurrence order of the respective repeating units in parentheses with subscript a", b", c", d" is not limited in the formulae.

The fluorine-containing oil may have a number average molecular weight of 1,000 to 30,000. In particular, the number average molecular weight of the compound represented by formula (IIIa) is preferably 2,000 to 8,000. In one embodiment, the number average molecular weight of the compound represented by formula (IIIb) is 3,000 to 8,000. In another embodiment, the number average molecular weight of the compound represented by formula (IIIb) is 8,000 to 30,000.

The curable composition may contain, for example, 0 to 500 parts by mass, preferably 0 to 100 parts by mass, more preferably 1 to 50 parts by mass, further preferably 1 to 5 parts by mass of the fluorine-containing oil based on 100 parts by mass of the PFPE-containing silane compound.

The fluorine-containing oil may be a compound represented by general formula Rf'—F, wherein Rf' is $C_{5-16}$ perfluoroalkyl group, from another viewpoint. The fluorine-containing oil may be a chlorotrifluoroethylene oligomer.

The compound represented by Rf'—F and the chlorotrifluoroethylene oligomer are preferable in that high affinity with the perfluoro(poly)ether group-containing silane compound where Rf is a $C_{1-16}$ perfluoroalkyl group is obtained.

Examples of the storage stabilizer may include methyltrimethoxysilane, methyltripropenoxysilane, vinyltributanoxysilane and methyltriacetoxysilane.

Examples of the filling agent may include fibrous filling agents such as asbestos, glass fiber and an organic fiber.

Examples of the colorant may include a pigment and a dye.

Examples of the heat resistance improver may include colcothar and cerium oxide.

Examples of the adhesiveness improver may include β-(3,4-epoxycyclohexyl)ethyltrimethoxysilane, γ-glycidoxypropyltriethoxysilane, γ-methacryloxypropyltrimethoxysilane, γ-methacryloxypropylmethyldiethoxysilane, N-β-(aminoethyl)-γ-aminopropyltrimethoxysilane, γ-aminopropyltriethoxysilane, γ-chloropropyltrimethoxysilane, γ-mercaptopropyltrimethoxysilane and γ-isocyanatopropyltriethoxysilane.

Examples of the liquid strengthening agent may include reticular polysiloxane having a triorganosiloxy unit and a $SiO_2$ unit.

The polymerization initiator may be an azo initiator such as azobisisobutyronitrile, methyl azoisobutyrate or azobisdimethylvaleronitrile; or benzoyl peroxide, potassium persulfate, ammonium persulfate, a benzophenone derivative, a phosphine oxide derivative, a benzoketone derivative, a phenylthioether derivative, an azido derivative, a diazo derivative or a disulfide derivative. Such a polymerization initiator may be used singly or in combinations of two or more kinds thereof.

A protecting layer is formed by treating the resin base material or the electronic component with the curable composition.

The treating method is not limited. For example, the treating method is performed by coating the resin base material and/or the electronic component with the curable composition, and, if necessary, performing a heat treatment or light irradiation to thereby cure the curable composition.

The protecting layer formed from the curable composition can be enhanced in adhesiveness by, if necessary, subjecting a portion to be treated, to a primer treatment prior to the treatment with the curable composition.

Hereinafter, an embodiment of the member for a wearable device of the present invention will be described with reference to drawings.

Figure 2:
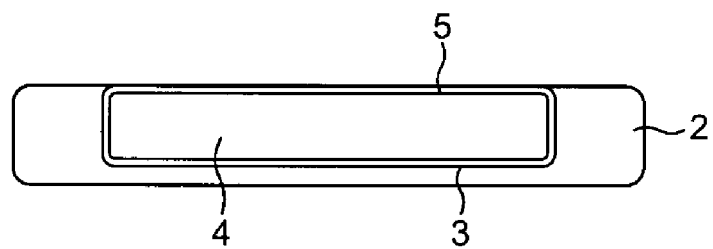
FIG. 2 is an X-X cross-sectional view of the watch band 1 illustrated in FIG. 1.

A watch band member 1 as one embodiment of the present invention is described. As illustrated in FIG. 1 and FIG. 2, the watch band member 1 of the present embodiment includes a band body 2 as a resin base material and an electronic component 4 received in a concave portion 3 formed in the band body 2. The entire surface of the electronic component 4 is covered with a protecting layer 5. That is, the present embodiment provides a member for a wearable device, in which an electronic component is directly covered with a protecting layer. The electronic component 4 is covered with a protecting layer 5 containing a PFPE-containing compound and thus is protected against sweat, a chemical substance, and the like.

Figure 3:
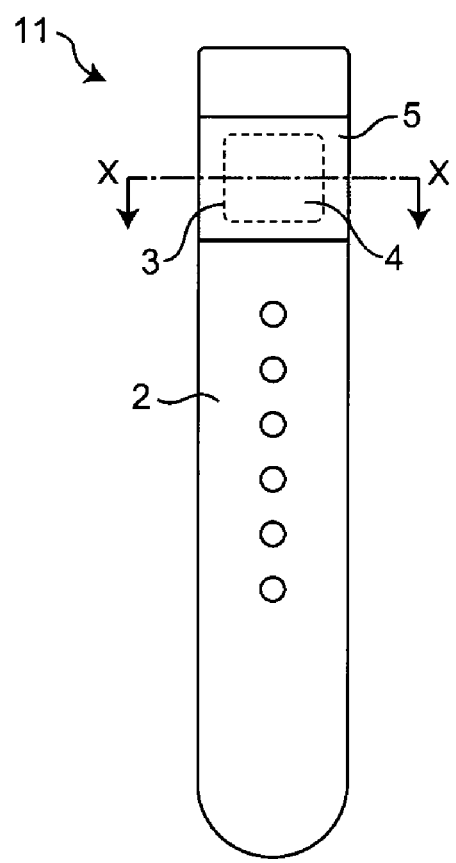
FIG. 3 is a plan view of a watch band member 11 in another embodiment of the present invention.
Figure 4:
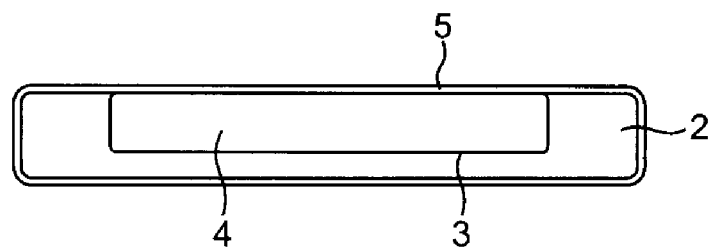
FIG. 4 is an X-X cross-sectional view of the watch band 11 illustrated in FIG. 3.

A watch band member 11 as another embodiment of the present invention is described. As illustrated in FIG. 3 and FIG. 4, the watch band member 11 of the present embodiment includes a band body 2 as a resin base material and an electronic component 4 received in a concave portion 3 formed in the band body 2. The concave portion 3 in which the electronic component 4 is accommodated is sealed by a protecting member 5. That is, the present embodiment provides a member for a wearable device, in which a resin base material has a concave portion, an electronic component is disposed on the concave portion and the concave portion and the electronic component are covered with a protecting layer from above. The concave portion 3 in which the electronic component 4 is received is sealed by a protecting layer 5 containing a PFPE-containing compound and thus the electronic component 4 is protected against sweat, a chemical substance, and the like.

Figure 5:
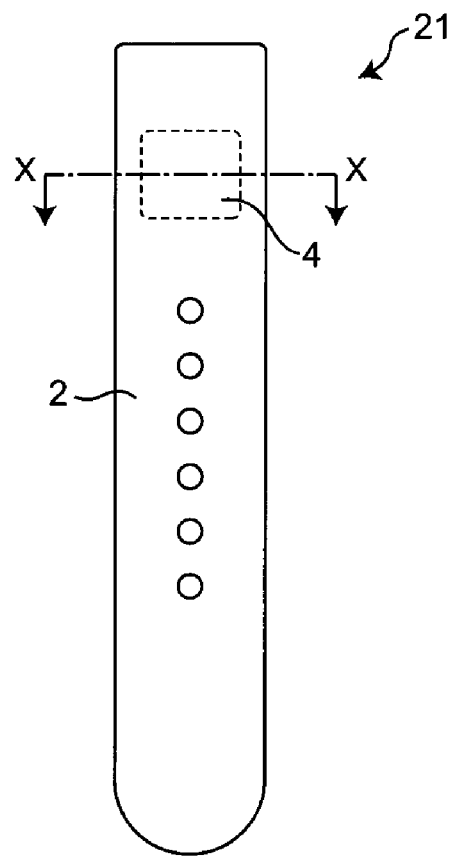
FIG. 5 is a plan view of a watch band member 21 in another embodiment of the present invention.
Figure 6:
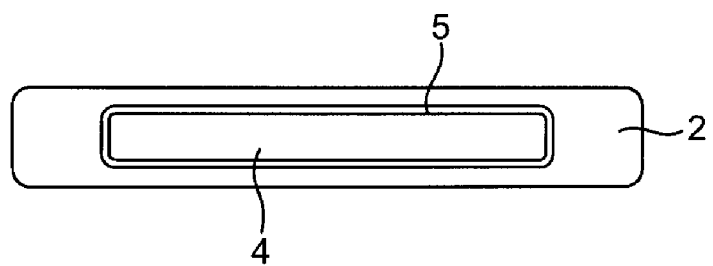
FIG. 6 is an X-X cross-sectional view of the watch band 21 illustrated in FIG. 5.

A watch band member 21 as another embodiment of the present invention is described. As illustrated in FIG. 5 and FIG. 6, the watch band member 21 of the present embodiment includes a band body 2 as a resin base material and an electronic component 4 embedded in the band body 2. The entire surface of the electronic component 4 is covered with a protecting layer 5. That is, the present embodiment provides a member for a wearable device, in which an electronic component is embedded in a resin base material and the electronic component is directly covered with a protecting layer. The electronic component 4 is covered with a protecting layer 5 containing a PFPE-containing compound and thus is protected against sweat, a chemical substance, and the like. Furthermore, the electronic component is embedded in the resin base material and can be more strongly protected.

Figure 7:
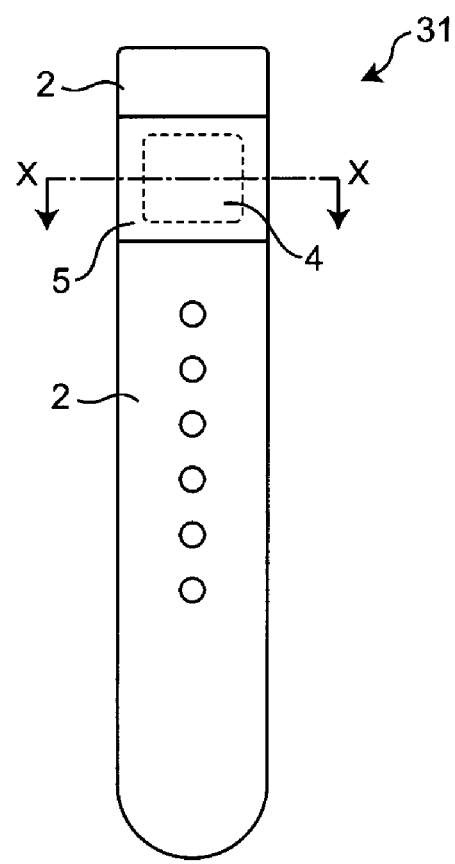
FIG. 7 is a plan view of a watch band member 31 in another embodiment of the present invention.
Figure 8:
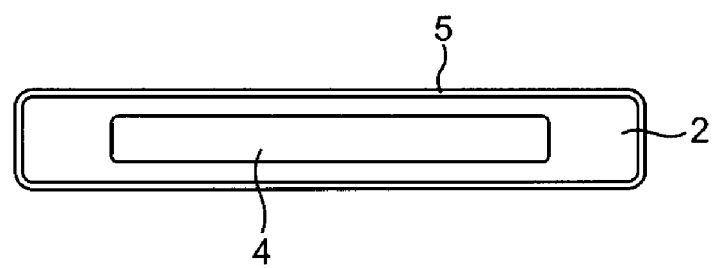
FIG. 8 is an X-X cross-sectional view of the watch band 31 illustrated in FIG. 7.

A watch band member 31 as another embodiment of the present invention is described. As illustrated in FIG. 7 and FIG. 8, the watch band member 31 of the present embodiment includes a band body 2 as a resin base material and an electronic component 4 embedded in the band body 2. At least a section of the resin base material with the electronic component 4 embedded therein, in which the electronic component 4 is embedded, is covered with a member for a wearable device. That is, provided is a member for a wearable device, in which an electronic component is embedded in a resin base material and the resin base material is covered with the protecting layer.

While the protecting layer 5 partially protects the resin base material 2, namely, a portion of the material, in which the electronic component 4 is embedded, in the watch band members 11 and 31, the protecting layer 5 can preferably protect the entire resin base material 2. Such embedding is not limited to an embodiment in which the electronic component 4 is completely embedded in the resin base material 2 and sealed, and also encompasses an embodiment in which the electronic component is fitted into the concave portion, and lidded thereon and sealed.

The watch band members 1, 11, 21 and 31 are assembled with corresponding other watch band members 7 and watch body sections 8, thereby forming respective watch-type wearable devices 9.

Figure 9:
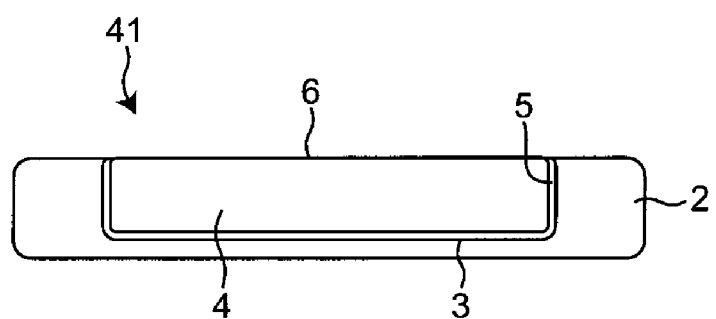
FIG. 9 is a cross-sectional view of a watch band in another embodiment.

A watch band member 41 as another embodiment of the present invention is described. As illustrated in FIG. 9, the watch band member 41 of the present embodiment includes a band body 2 as a resin base material and an electronic component 4 accommodated in a concave portion 3 formed in the band body 2. A portion excluding an upper surface 6, of the electronic component 4, is covered with the protecting layer 5. That is, the present embodiment provides a member for a wearable device, in which an electronic component, one portion of which is excluded, is covered with a protecting layer. The electronic component 4, one portion of which is excluded, is covered with a protecting layer 5 containing a PFPE-containing compound and thus not only can be protected against sweat, a chemical substance, and the like, but also can be connected to other member such as a wiring or a terminal at such a portion not protected.

Figure 10:
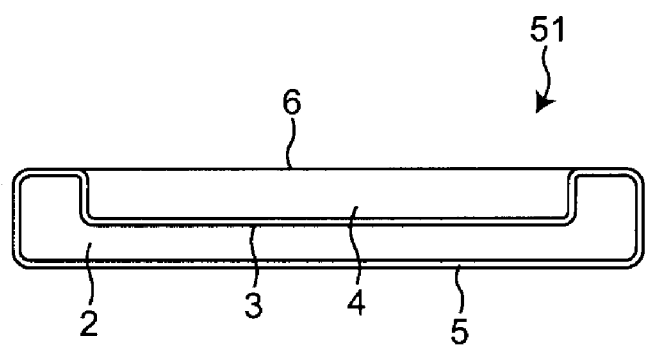
FIG. 10 is a cross-sectional view of a watch band in another embodiment.
Figure 11:
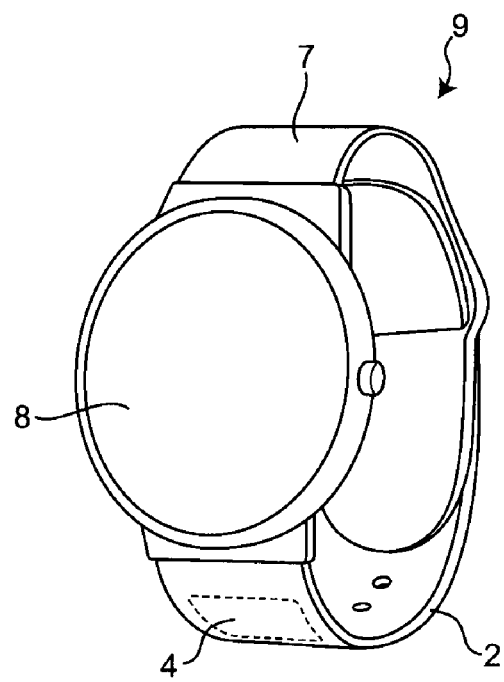
FIG. 11 is a perspective view of a watch-type wearable device 9 in which the watch band 1 of the present invention is used.

A watch band member 51 as another embodiment of the present invention is described. As illustrated in FIG. 10, the watch band member 51 of the present embodiment includes a band body 2 as a resin base material and an electronic component 4 accommodated in a concave portion 3 formed in the band body 2. The band body 2 is covered with a protecting layer 5 and a portion excluding an upper surface 6, of the electronic component 4, is also covered therewith in the concave portion 3. That is, the present embodiment provides a member for a wearable device, in which a protecting layer protects not only an electronic component, but also a resin base material.

Figure 12:
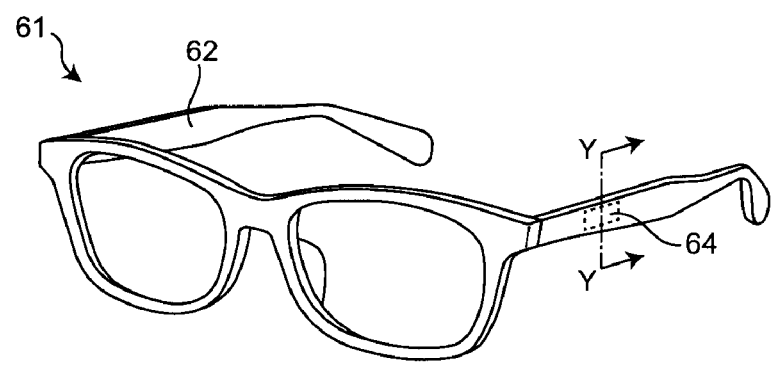
FIG. 12 is a perspective view of an eyeglass frame in one embodiment of the present invention.
Figure 13:
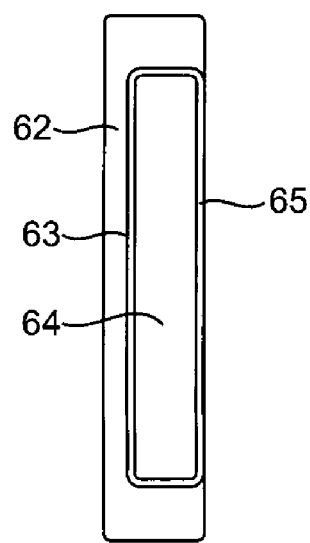
FIG. 13 is a Y-Y cross-sectional view of the eyeglass frame illustrated in FIG. 12.

An eyeglass frame 61 as one embodiment of the present invention is described. As illustrated in FIG. 12 and FIG. 13, the eyeglass frame 61 of the present embodiment includes a frame body 62 as a resin base material and an electronic component 64 accommodated in a concave portion 63 formed in the frame body 62. The entire surface of the electronic component 64 is covered with a protecting layer 65. That is, the present embodiment provides a member for a wearable device, in which an electronic component is directly covered with a protecting layer. The electronic component 64 is covered with a protecting layer 5 containing a PFPE-containing compound and thus is protected against sweat, a chemical substance and the like.

While the embodiments are described above, the present invention is not limited to the embodiments and can be variously modified without departing from the gist and the scope of the claims.

EXAMPLES

The occurrence order of repeating units ($CF_2O$) and ($CF_2CF_2O$) constituting perfluoropolyether is not limited in the present Examples. All chemical formulae shown below are represented in terms of average compositional feature.

Example 1

Production of Test Piece

A thermosetting silicone resin was pressed in a mold to thereby form a sample sheet having a concave of 20 mm length×11 mm width×1.5 mm depth. A button-type battery to which an electrode was installed so that any current flowed was placed in the concave, a PFPE-containing curing composition shown below was poured from above so that the button-type battery was protected, and was left to still stand and cured at 25° C. for 72 hours, to provide a test piece.

Preparation of PFPE-Containing Curing Composition 1

PFPE-containing compound A, tetraethoxysilane as a cross-linking agent, and tetraisopropaxy titanium as a curing catalyst were weighed in a glass vessel for mixing in amounts of 100 parts by weight, 1 part by weight, and 0.5 parts by weight, respectively, and stirred with a magnetic stirrer, to prepare a curable composition.

PFPE-containing compound A

wherein e=48 and f=37

Evaluation

The resulting test piece was immersed in 5% saline, and placed under an environment at 25° C. and observed. When the saline passed through a protecting layer and reached the battery, any air bubble occurred in the saline by electrolysis and corrosion occurred on an electrode. The respective times at which such air bubble and electrode corrosion occurred were observed. The results are shown in Table 1 below.

Example 2

Evaluation was performed by the same procedure as in Example 1 except that PFPE-containing curing composition 2 was used for a protecting layer and curing was performed in conditions of 100° C. and 2 hours.

Preparation of PFPE-Containing Curing Composition 2

Compound D as a cross-linking agent and a xylene solution containing 2% of a Pt complex of 1,3-divinyl-1,1,3,3-tetramethyldisiloxane as a curing catalyst were weighed in a glass vessel for mixing, in amounts of 4 parts by weight and 0.4 parts by weight based on 100 parts by weight of PFPE-containing compound C, and stirred and mixed, to prepare a curable composition.

PFPE-Containing Compound C

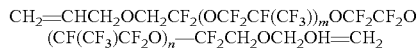

wherein m+n=54

[Formula 51]

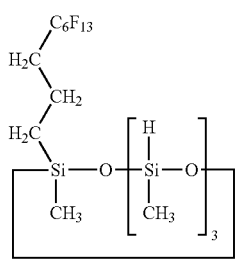

Compound D

Comparative Example 1

The same test as in Example 1 was performed without use of any protecting layer.

Comparative Example 2

Evaluation was performed in the same conditions as in Example 1 by using a silicone elastomer (HC2100 manufactured by Dow Corning Toray Co., Ltd.) for a protecting layer.

TABLE 1

|  | Time taken for occurrence of bubble | Time taken for occurrence of rust |
|---|---|---|
| Example 1 | 304 hours | 312 hours |
| Example 2 | 320 hours | 325 hours |
| Comparative Example 1 | 0 minutes | 2 minutes |
| Comparative Example 2 | 3 hours | 6 hours |

INDUSTRIAL APPLICABILITY

The portion for a wearable device of the present invention can be used for various wearable devices.

REFERENCE SIGNS LIST 1, 11, 21, 31, 41, 51 . . . watch band member
2 . . . band body, 3 . . . concave portion, 4 . . . electronic component, 5 . . . protecting layer
7 . . . other watch band member, 8 . . . watch body section, 3 . . . watch-type wearable device
61 . . . eyeglass frame, 62 . . . eyeglass frame body, 63 . . . concave portion
64 . . . electronic component, 65 . . . protecting layer

The invention claimed is:
1. A member for a wearable device, comprising:
a resin base material;
an electronic component; and
a protecting layer which protects the electronic component, wherein
the protecting layer is a layer formed from a curable composition comprising a perfluoropolyether group-containing compound, and
the perfluoropolyether group-containing compound is a perfluoropolyether group-containing silane compound represented by formula (A), (B), (C) or (D):

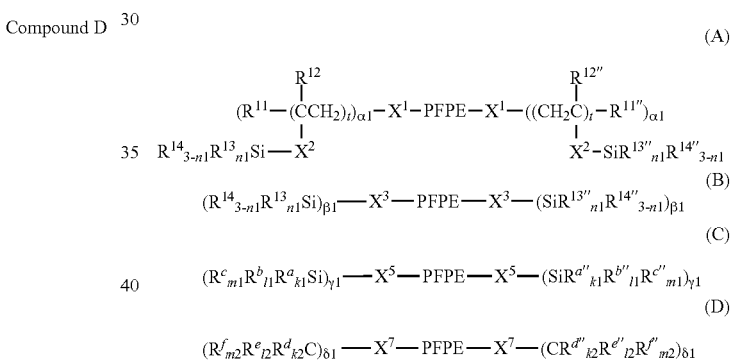

wherein:
PFPE, at each occurrence, is each independently a group represented by formula:
—$(OC_6F_{12})_a$—$(OC_5F_{10})_b$—$(OC_4F_8)_c$—$(OC_3X^{10}_6)_d$—$(OC_2F_4)_e$—$(OCF_2)_f$—
wherein a, b, c, d, e and f are each independently an integer of 0 or more and 200 or less, the sum of a, b, c, d, e and f is at least 1, the occurrence order of the respective repeating units in parentheses with a, b, c, d, e or f is not limited in the formula, and $X^{10}$, at each occurrence, is each independently a hydrogen atom, a fluorine atom or a chlorine atom;
$R^{13}$, at each occurrence, each independently represents a hydroxyl group or a hydrolyzable group;
$R^{14}$, at each occurrence, each independently represents a hydrogen atom or an alkyl group having 1 to 22 carbon atoms;
$R^{11}$, at each occurrence, each independently represents a hydrogen atom or a halogen atom;
$R^{12}$, at each occurrence, each independently represents a hydrogen atom or a lower alkyl group;
$R^{11''}$, $R^{12''}$, $R^{13''}$ and $R^{14''}$ are as defined for $R^{11}$, $R^{12}$, $R^{13}$, and $R^{14}$, respectively;

n1 with respect to each ($-SiR^{13}{}_{n1}R^{14}{}_{3-n1}$) unit or each ($-SiR^{13"}{}_{n1}R^{14"}{}_{3-n1}$) unit is independently an integer of 0 to 3;

provided that at least two groups, at each occurrence, each independently selected from the group consisting of $R^{13}$ and $R^{13"}$ are present in formulae (A) and (B);

$X^1$, at each occurrence, each independently represents a single bond or an organic group having a chemical valence of 2 to 10;

$X^2$, at each occurrence, each independently represents a single bond or an organic group having a chemical valence of two;

t, at each occurrence, is each independently an integer of 1 to 10;

α1, at each occurrence, is each independently an integer of 1 to 9;

$X^3$, at each occurrence, each independently represents a single bond or an organic group having a chemical valence of 2 to 10;

β1 at each occurrence, is each independently an integer of 1 to 9;

$X^5$, at each occurrence, each independently represents a single bond or an organic group having a chemical valence of 2 to 10;

γ1, at each occurrence, is each independently an integer of 1 to 9;

$R^a$, at each occurrence, each independently represents $-Z^3-SiR^{71}{}_{p1}R^{72}{}_{q1}R^{73}{}_{r1}$;

$Z^3$, at each occurrence, each independently represents an oxygen atom or an organic group having a chemical valence of two;

$R^{71}$, at each occurrence, each independently represents $R^{a'}$;

$R^{a'}$ is as defined for $R^a$;

the number of Si linearly linked via a $Z^3$ group in $R^a$ is at most 5;

$R^{72}$, at each occurrence, each independently represents a hydroxyl group or a hydrolyzable group;

$R^{73}$, at each occurrence, each independently represents a hydrogen atom or a lower alkyl group;

p1, at each occurrence, is each independently an integer of 0 to 3;

q1, at each occurrence, is each independently an integer of 0 to 3;

r1, at each occurrence, is each independently an integer of 0 to 3;

$R^{a"}$, at each occurrence, each independently represents $-Z^3-SiR^{71}{}_{p1}R^{72"}{}_{q1}R^{73}{}_{r1}$;

$R^{72"}$ is as defined for $R^{72}$;

provided that the sum of p1, q1 and r1 with respect to each ($-Z^3-SiR^{71}{}_{p1}R^{72}{}_{q1}R^{73}{}_{r1}$) or with respect to each ($-Z^3-SiR^{71}{}_{p1}R^{72"}{}_{q1}R^{73}{}_{r1}$) is 3 and at least one q1 in formula (C) is an integer of 1 to 3;

$R^b$, at each occurrence, each independently represents a hydroxyl group or a hydrolyzable group;

$R^c$, at each occurrence, each independently represents a hydrogen atom or a lower alkyl group;

$R^{b"}$ and $R^{c"}$ are as defined for $R^b$ and $R^c$, respectively;

k1, at each occurrence, is each independently an integer of 0 to 3;

l1, at each occurrence, is each independently an integer of 0 to 3;

m1, at each occurrence, is each independently an integer of 0 to 3;

provided that the sum of k1, l1 and m1 with respect to each ($SiR^a{}_{k1}R^b{}_{l1}R^c{}_{m1}$) or with respect to each ($SiR^{a"}{}_{k1}R^{b"}{}_{l1}R^{c"}{}_{m1}$) is 3;

at least two groups selected from the group consisting of $R^b$, $R^{b"}$, $R^{72}$ and $R^{72"}$ are present in formula (C);

$X^7$ each independently represents a single bond or an organic group having a chemical valence of 2 to 10;

δ1 is each independently an integer of 1 to 9;

$R^d$, at each occurrence, each independently represents $-Z^4-CR^{81}{}_{p2}R^{82}{}_{q2}R^{83}{}_{r2}$;

$Z^4$, at each occurrence, each independently represents an oxygen atom or an organic group having a chemical valence of two;

$R^{81}$, at each occurrence, each independently represents $R^{d'}$;

$R^{d'}$ is as defined for $R^d$;

the number of C linearly bonded via a $Z^4$ group in $R^d$ is at most 5;

$R^{82}$, at each occurrence, each independently represents $-Y-SiR^{85}{}_{n2}R^{86}{}_{3-n2}$;

Y, at each occurrence, each independently represents an organic group having a chemical valence of two;

$R^{85}$, at each occurrence, each independently represents a hydroxyl group or a hydrolyzable group;

$R^{86}$, at each occurrence, each independently represents a hydrogen atom or a lower alkyl group;

$R^{83}$, at each occurrence, each independently represents a hydrogen atom, a hydroxyl group or a lower alkyl group;

p2, at each occurrence, is each independently an integer of 0 to 3;

q2, at each occurrence, is each independently an integer of 0 to 3;

r2, at each occurrence, is each independently an integer of 0 to 3;

$R^{d"}$, at each occurrence, each independently represents $-Z^4-CR^{81}{}_{p2}R^{82"}{}_{q2}R^{83}{}_{r2}$;

$R^{82"}$ represents $-Y-SiR^{85"}{}_{n2}R^{86"}{}_{3-n2}$;

provided that the sum of p2, q2 and r2 with respect to each ($-Z^4-CR^{81}{}_{p2}R^{82}{}_{g2}R^{83}{}_{r2}$) or with respect to each ($-Z^4-CR^{81}{}_{p2}R^{82"}{}_{g2}R^{83}{}_{r2}$) is 3;

n2 with respect to a each ($-Y-SiR^{85}{}_{n2}R^{86}{}_{3-n2}$) unit or with respect to a each ($-Y-SiR^{85"}{}_{n2}R^{86"}{}_{3-n2}$) unit independently represents an integer of 0 to 3;

$R^{85"}$ and $R^{86"}$ are as defined for $R^{85}$ and $R^{86}$, respectively;

$R^e$, at each occurrence, each independently represents $-Y-SiR^{85}{}_{n2}R^{86}{}_{3-n2}$;

$R^{e"}$, at each occurrence, independently represents $-Y-SiR^{85"}{}_{n2}R^{86"}{}_{3-n2}$;

$R^f$, at each occurrence, each independently represents a hydrogen atom, a hydroxyl group or a lower alkyl group;

$R^{f"}$ is as defined for $R^f$;

k2, at each occurrence, i each s independently an integer of 0 to 3;

l2, at each occurrence, is each independently an integer of 0 to 3; and m2, at each occurrence, is each independently an integer of 0 to 3;

provided that the sum of k2, l2 and m2 with respect to ($CR^d{}_{k2}R^e{}_{l2}R^f{}_{m2}$) or with respect to ($CR^{d"}{}_{k2}R^{e"}{}_{l2}R^{f"}{}_{m2}$) is 3, and two or more groups selected from the group consisting of a group represented by $-Y-SiR^{85}{}_{n2}R^{86}{}_{3-n2}$ wherein n2 is 1 or more and a group represented by $-Y-SiR^{85''}_{n2}R^{86''}_{3-n2}$ wherein n2 is 1 or more are present in formula (D).

2. The member for a wearable device according to claim 1, wherein the perfluoropolyether group-containing silane compound has a carbon-carbon double bond at a molecular end.

3. The member for a wearable device according to claim 1, wherein the electronic component is directly covered with the protecting layer.

4. The member for a wearable device according to claim 1, wherein the resin base material has a concave portion, the electronic component is disposed on the concave portion, and the concave portion and the electronic component are covered with the protecting layer from thereabove.

5. The member for a wearable device according to claim 1, wherein the electronic component is embedded in the resin base material, and the resin base material is covered with the protecting layer.

6. The member for a wearable device according to claim 1, which is an eyeglass frame.

7. The member for a wearable device according to claim 1, which is a watch band.

8. A wearable device comprising the member for a wearable device according to claim 1.

* * * * *